(12) United States Patent
Juni

(10) Patent No.: US 7,071,473 B2
(45) Date of Patent: Jul. 4, 2006

(54) SINGLE PHOTON EMISSION COMPUTED TOMOGRAPHY SYSTEM

(76) Inventor: Jack E. Juni, 25595 York St., Royal Oak, MI (US) 48067

( * ) Notice: Subject to any disclaimer, the term of this patent is extended or adjusted under 35 U.S.C. 154(b) by 0 days.

(21) Appl. No.: 11/250,647

(22) Filed: Oct. 14, 2005

(65) Prior Publication Data

US 2006/0033028 A1    Feb. 16, 2006

Related U.S. Application Data

(63) Continuation of application No. 10/933,036, filed on Sep. 2, 2004, which is a continuation of application No. 10/872,253, filed on Jun. 18, 2004, which is a continuation-in-part of application No. 10/358,961, filed on Feb. 5, 2003, which is a continuation-in-part of application No. 09/549,435, filed on Apr. 14, 2000, now Pat. No. 6,525,320.

(60) Provisional application No. 60/480,381, filed on Jun. 20, 2003, provisional application No. 60/151,378, filed on Aug. 30, 1999, provisional application No. 60/129,239, filed on Apr. 14, 1999.

(51) Int. Cl.
*G01T 1/166* (2006.01)
(52) U.S. Cl. .............................. 250/363.04; 250/363.01
(58) Field of Classification Search ........... 250/363.04, 250/363.01; 378/4
See application file for complete search history.

(56) References Cited

U.S. PATENT DOCUMENTS

| | | | |
|---|---|---|---|
| 4,090,080 A | 5/1978 | Tosswill | 250/366 |
| 4,229,651 A | 10/1980 | Danos | 250/272 |
| 4,584,478 A | 4/1986 | Genna et al. | 250/363 |
| 4,821,304 A | 4/1989 | Danos | 378/86 |
| 4,937,453 A | 6/1990 | Nelson | 250/370.09 |
| 5,021,667 A | 6/1991 | Genna et al. | 250/363 |

(Continued)

FOREIGN PATENT DOCUMENTS

EP    0 289 737 A1    11/1988

OTHER PUBLICATIONS

IEEE Transaction on Medical Imaging, vol. 7, No. 4 Dec. 1988 entitled SPRINT II: A Second Generation Single Photon Ring Tomograph by W.L. Rogers, N.H. Clinthorne, L. Shao, P. Chiao, Y. Ding, J. A. Stamos, and K.F. Koral.

(Continued)

*Primary Examiner*—Otilia Gabor
(74) *Attorney, Agent, or Firm*—Gifford, Krass, Groh, Sprinkle, Anderson & Citkowski, PC

(57) ABSTRACT

A single photon emission computed tomography system includes a base for supporting a patient and a detector assembly adjacent the field of view. The detector assembly detects photon strikes from the field of view. A photon-blocking member is disposed between the field of view and the detector and has an aperture slot that allows passage of photons aligned with the slot. A collimating assembly includes a plurality of collimating vanes formed of photon-attenuating material. A support assembly supports the collimating assembly and includes a first support member and a second support member with the collimating assembly being disposed therebetween. An adjustment assembly includes a first adjuster operable to adjust a first distance between the collimating assembly and the first support member and a second adjuster operable to adjust a second distance between the collimating assembly and the second support member.

35 Claims, 58 Drawing Sheets

U.S. PATENT DOCUMENTS

| | | | |
|---|---|---|---|
| 5,032,728 A | 7/1991 | Chang et al. | 250/363 |
| 5,225,980 A | 7/1993 | Hsieh et al. | 364/413.14 |
| 5,600,144 A | 2/1997 | Worstell | |
| 5,600,145 A | 2/1997 | Plummer | |
| 5,608,221 A | 3/1997 | Bertelsen et al. | |
| 5,821,541 A | 10/1998 | Tumer | |
| 5,825,031 A | 10/1998 | Wong | |
| 5,838,009 A | 11/1998 | Plummer et al. | 250/363.05 |
| 5,841,140 A | 11/1998 | McCroskey et al. | |
| 6,040,580 A | 3/2000 | Watson et al. | 250/363.05 |
| 6,147,352 A | 11/2000 | Ashburn | 250/363.05 |
| 6,359,279 B1 | 3/2002 | Gagnon et al. | 250/363.1 |
| 6,504,157 B1 | 1/2003 | Juni | 250/363.04 |
| 6,525,320 B1 | 2/2003 | Juni | 250/363.04 |
| 6,661,865 B1 * | 12/2003 | Popilock | 378/19 |
| 2003/0128813 A1 | 7/2003 | Appleby et al. | 378/147 |

OTHER PUBLICATIONS

IEEE Transactions on Nuclear Science, vol. NS-26, No. 1, Feb. 1979 entitled Introducing Sprint: A Single Photon Ring System For Emission Tomography by J.J. Williams, W.P. Snapp, G.F. Knoll.

Performance Evaluation Of Sprint, A Single Photon Ring Tomograph For Brain Imaging by W. Leslie Rogers, Neal H. Clinthorne, John Stamos, Kenneth F. Koral, Robert Mayans, Glenn F. Knoll, Jack Juni, John W. Keyes, Jr., and Beth A. Harkness.

IEEE Transactions on Medical Imaging, vol. MI-1, No. 1, Jul. 1982, entitled A Stationary Detector Single Photon Ring Tomograph For Brain Imaging, by W.L. Rogers, N.H. Clinthorne, J. Stamos, K.F., Koral, R. Mayans, J.W. Keyes, Jr., J.J. Williams, W.P. Snapp, and G.F. Knoll.

IEEE Transactions on Nuclear Science, vol. 40, No. 4, Aug. 1993, entitled Ultra-High-Resolution Brain Spect Imaging: Simulation Results by M.M. Rogulski, H.B. Barber, H.H. Barrett, R.L. Shoemaker and J.M. Woolfenden, University of Arizona, Tueson, AZ 85724.

* cited by examiner

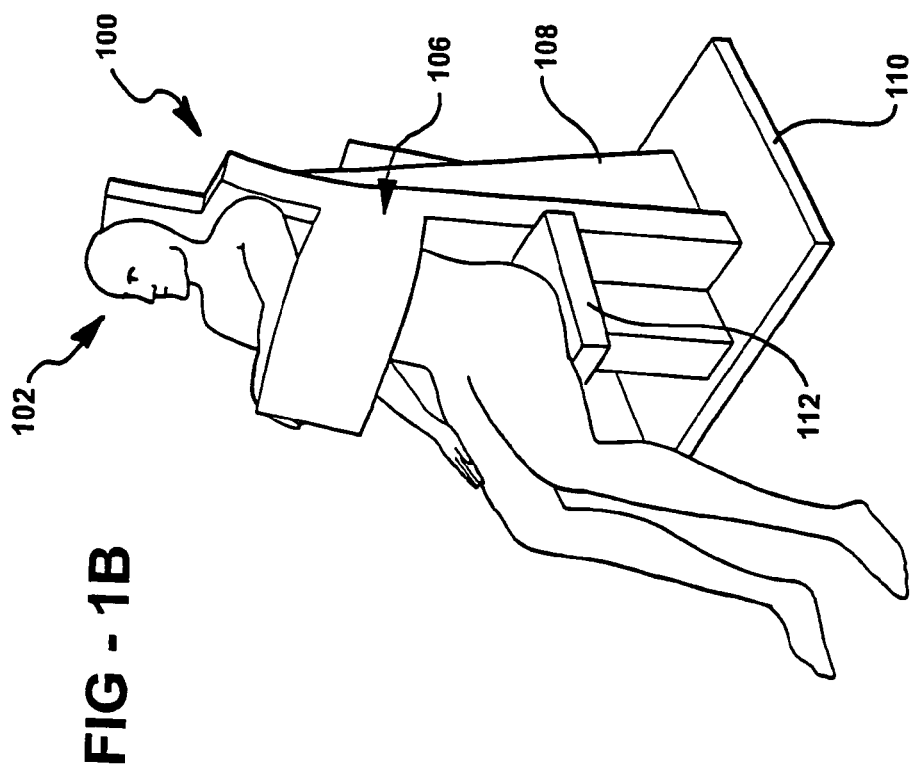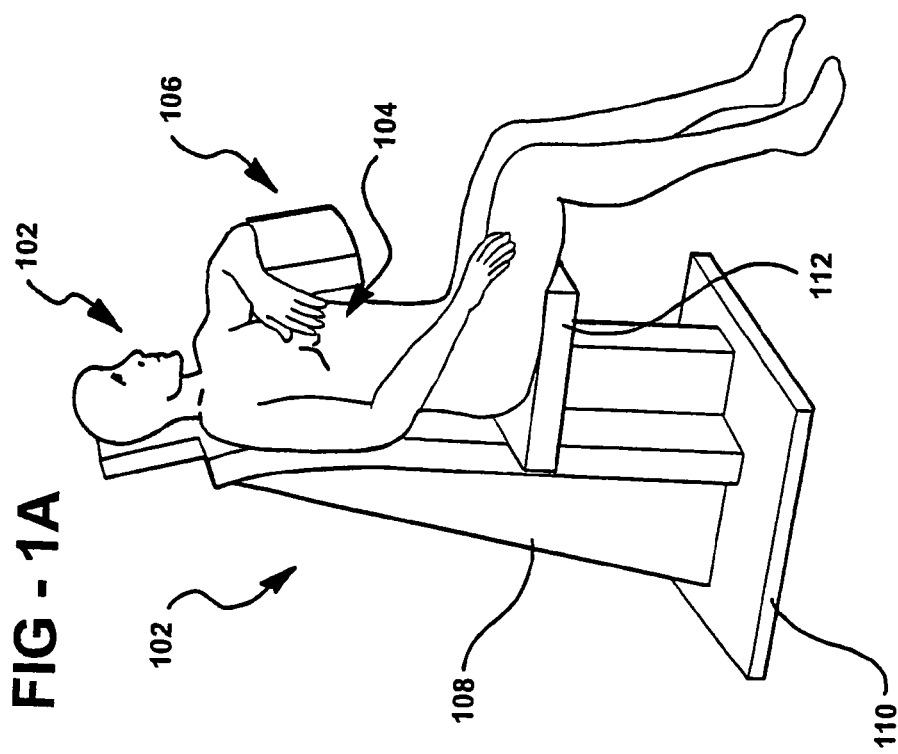

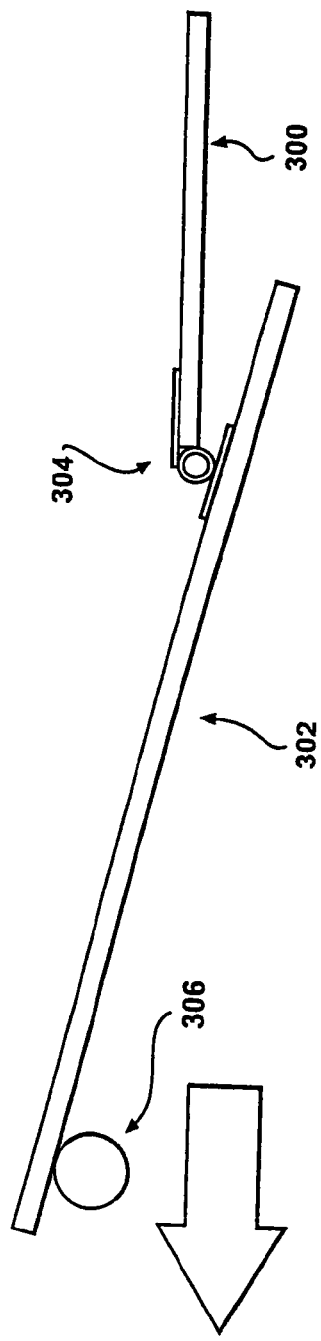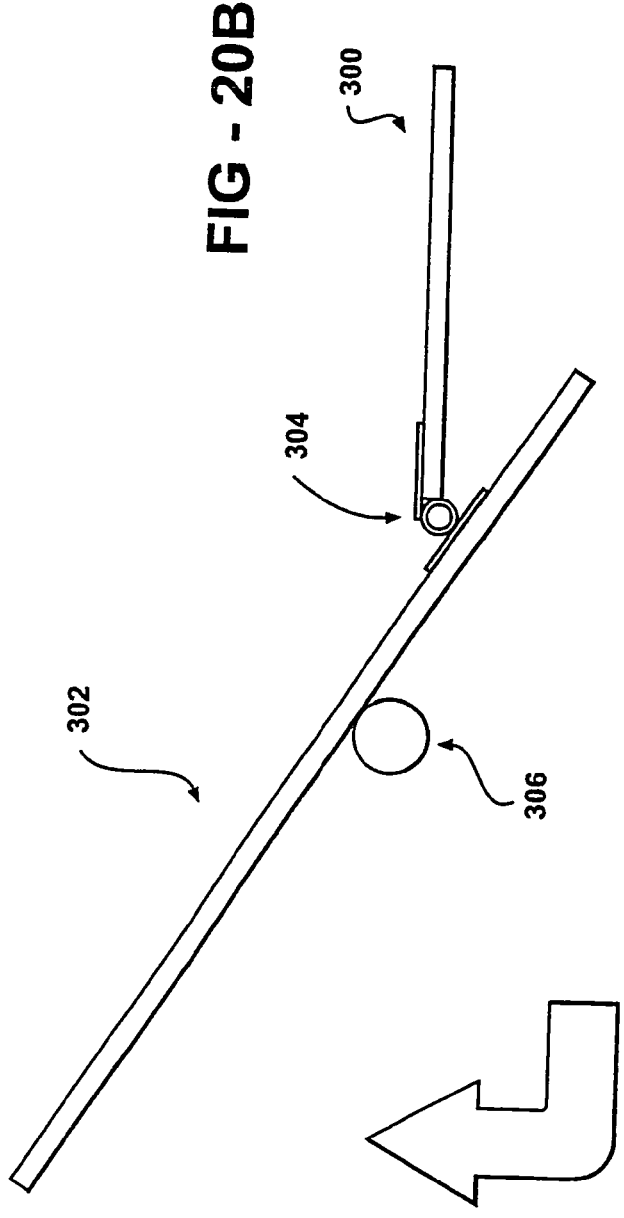
FIG-20A
FIG-20B

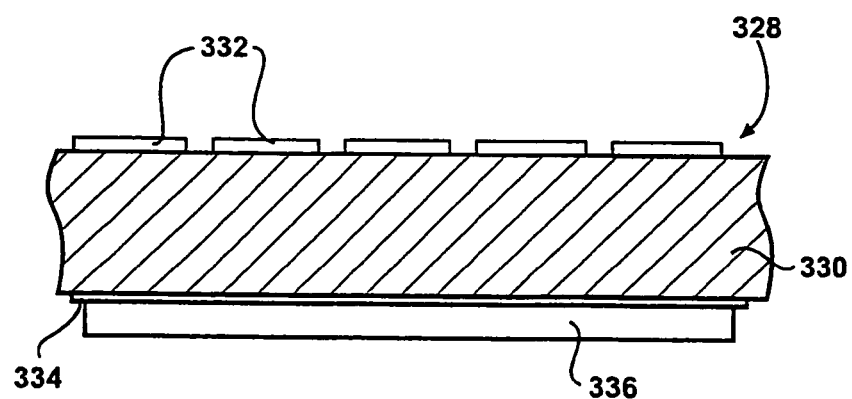
FIG - 25
FIG - 26
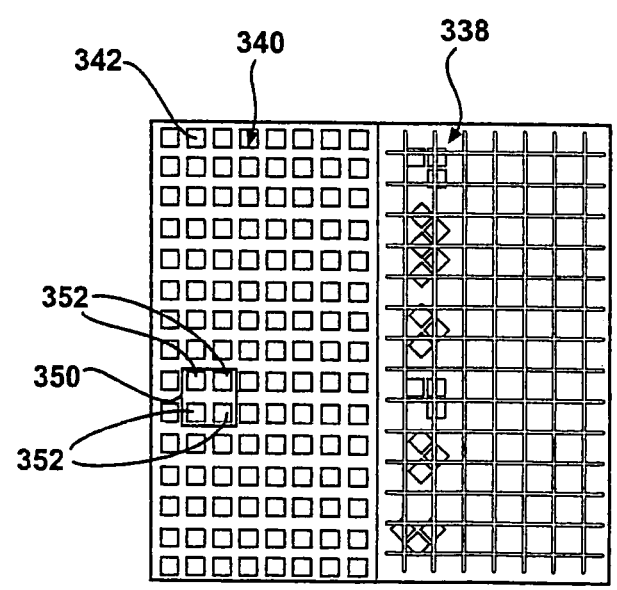

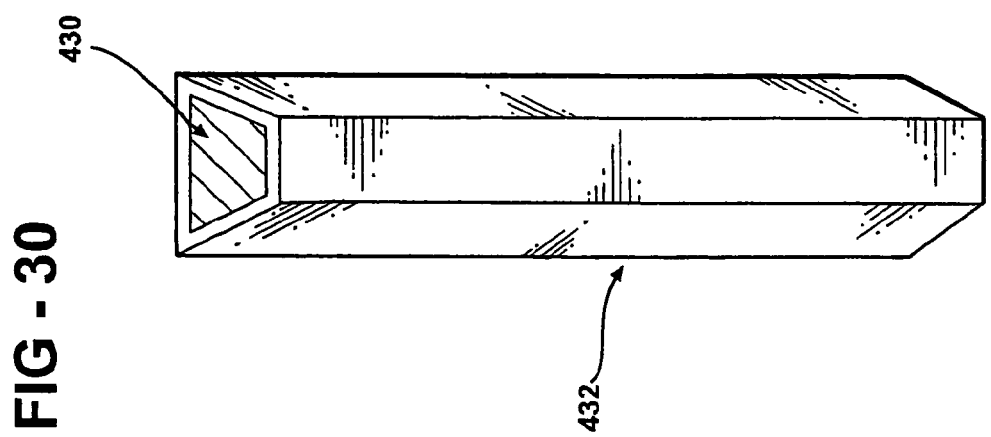
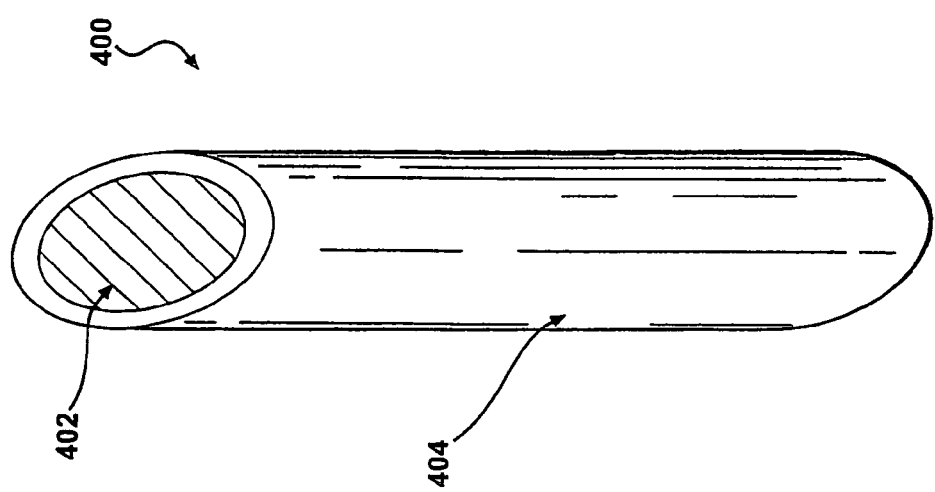

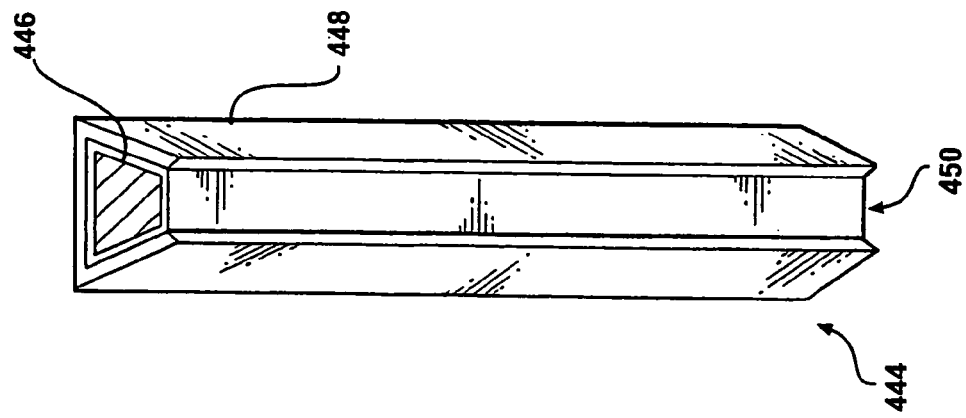
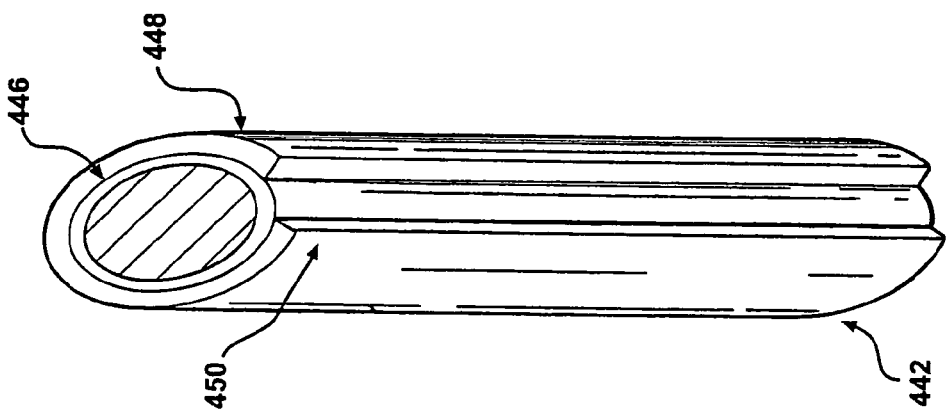

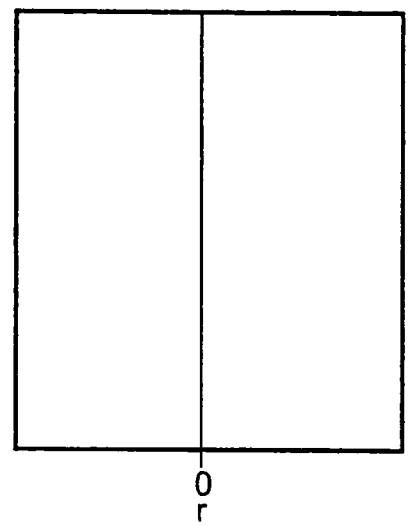
FIG - 42
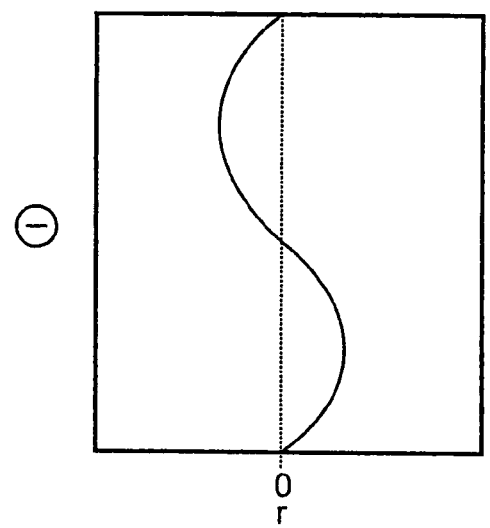
FIG - 43
FIG - 44
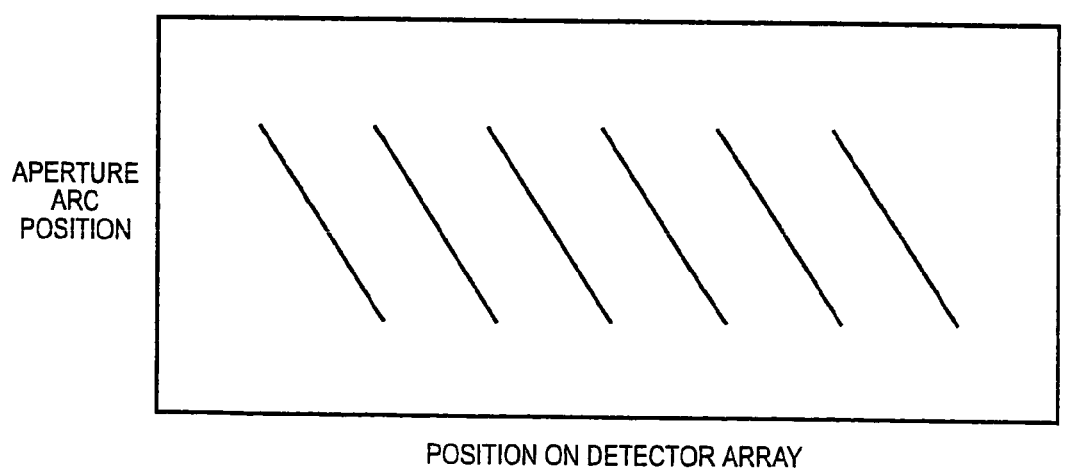
APERTURE ARC POSITION
POSITION ON DETECTOR ARRAY $\emptyset = \arcsin(r/R_{app}) - \theta$ $\psi = \arcsin(r/R_{det}) - \theta$

750

SINGLE PHOTON EMISSION COMPUTED TOMOGRAPHY SYSTEM

CROSS-REFERENCE TO RELATED APPLICATIONS

This application is a continuation of U.S. patent application Ser. No. 10/933,036, filed Sep. 2, 2004; said application being a continuation of U.S. patent application Ser. No. 10/872,253, filed Jun. 18, 2004, which is a continuation-in-pan of U.S. patent application Ser. No. 10/358,961, filed Feb. 5, 2003, which is a continuation-in-part of U.S. patent application Ser. No. 09/549,435, filed Apr. 14, 2000, now U.S. Pat. No. 6,525,320 issued Feb. 25, 2003, which claims priority from U.S. Provisional Patent Application Ser. Nos. 60/129,239, filed Apr. 14, 1999 and 60/151,378, filed Aug. 30, 1999.

U.S. patent application Ser. No. 10/872,253 claims priority from U.S. Provisional Patent Application Ser. No. 60/480,381, filed Jun. 20, 2003. The entire content of each application and patent are incorporated herein by reference.

FIELD OF THE INVENTION

The present invention relates generally to imaging systems and, more specifically, to a single photon emission computed tomography system.

BACKGROUND OF THE INVENTION

Medical radionuclide imaging (Nuclear Medicine) is a key component of modern medical practice. This methodology involves the administration, typically by injection, of tracer amounts of a radioactive substance, which subsequently localizes in the body in a manner dependent on the physiologic function of the organ system being studied. The radiotracer emissions, most commonly gamma photons, are imaged with a detector outside the body, creating a map of the radiotracer distribution within the body. When interpreted by an appropriately trained physician, these images provide information of great value in the clinical diagnosis and treatment of disease. Typical applications of this technology include detection of coronary artery disease (thallium scanning) and detection of cancerous involvement of bones (bone scanning). The overwhelming bulk of clinical radionuclide imaging is performed using gamma emitting radiotracers and detectors known as "gamma cameras".

Gamma cameras typically consist of a large scintillation crystal (e.g. sodium iodide) having the property of emitting light when struck by gamma photons. Affixed to the rear of this crystal are multiple photomultiplier tubes with associated circuitry to detect the light flashes and to locate their position within the scintillation crystal. In front of the crystal is a collimator, typically consisting of several millimeters of lead with multiple holes penetrating it. The collimator serves to absorb all incoming photons except those approaching the crystal generally from the appropriate direction. The crystal, photomultiplier tubes and associated circuitry are typically enclosed in a large lead case that serves to shield the detector from unwanted external radiation. The entire apparatus is mounted on a gantry with a motorized apparatus for positioning the detector near the patient.

A gamma camera provides a two-dimensional image of radiotracer distribution. However, the distribution of radiotracers within the body is typically three-dimensional. The technique of single photon emission tomography (SPECT) is used to create three-dimensional, tomographic images similar to a "radionuclide CT scan" by using computer processing to "reconstruct" the three-dimensional tracer distribution from a series of two-dimensional gamma camera images obtained from multiple angles around the patient. This is almost universally accomplished by mounting one or more gamma cameras to a motorized gantry and orbiting them around the patient. The data thus acquired is then processed to yield the three-dimensional images.

The three-dimensional SPECT images have been demonstrated to provide higher image contrast and to reduce apparent overlap of body structures. SPECT imaging is now considered to be the state-of-the-art in radionuclide imaging of the heart and now accounts for more than half of all cardiac nuclear imaging performed in the United States.

Despite its many advantages, SPECT imaging is not yet available to all patients who might benefit from it. Current SPECT instrumentation has a number of disadvantages which have impeded its wider implementation.

Current SPECT systems are bulky, typically requiring a large, dedicated room to house them. The collimating systems are relatively inefficient, blocking a high percentage of emitted radiation. Thus, most new clinical systems simultaneously utilize two or more gamma camera detectors mounted on a single gantry. Since each detector typically weighs several hundred pounds, the supporting gantry must be large and heavy. Most SPECT installations require specially constructed rooms with added floor reinforcement. Since accurate image reconstruction requires precise detector placement, SPECT systems require heavy positioning systems consisting of motors and gearing capable of moving and positioning hundreds of pounds of apparatus to a precision of approximately a millimeter. These systems are necessarily large, heavy and expensive.

Although there is great medical need to image patients in a variety of settings, including doctors' offices, emergency rooms and intensive care units, the great size and bulk of current SPECT systems has required them to be in a fixed location, typically a hospital Radiology or Nuclear Medicine department. There are significant medical and patient convenience advantages to having cardiac SPECT imaging performed in the immediate presence of the attending Cardiologist. Many studies have shown that the cost of care delivered in an outpatient office setting is less than that of a hospital setting. Despite these compelling factors, the size and cost constraints of current systems have greatly limited their penetration into the community and have particularly limited their availability in physicians' offices. In addition, the large space requirements of current systems have imposed significant costs on hospitals providing SPECT services.

Current SPECT systems have additional limitations. As the gamma cameras orbit around the patient, large multiconductor cables are required to carry power and data to and from each detector. These cables are repeatedly flexed during system operation and are a frequent cause of equipment breakdown.

The large and heavy nature of existing systems has dictated a mechanical gantry design that is highly stable, yet cost effective. This has resulted in systems in which the patient must lie in a supine (flat on the back) position on a narrow platform that extends into a vertically oriented gantry. In order to permit the detectors to be as close as possible to the chest and to enable the large, moving detectors to safely pass around the patient, current systems require the patient to maintain one or both arms in an uncomfortable position held over the head. This is painful for most patients and impossible for some. In addition, the supine position is uncomfortable for many patients, particularly for those with back problems. Many patients feel claustrophobic when inside the equipment. The narrow platform required to permit camera rotation around the patient is uncomfortable for large individuals and is often perceived as insecure or precarious by those undergoing scans. Also, the fact that the patient is partially enclosed by the equipment during imaging may serve to limit physician or nursing access to critically ill patients.

SUMMARY OF THE INVENTION

The present invention provides a plurality of imaging systems and components therefore. According to one embodiment, a single photon emission computed tomography system includes a base with a patient support for supporting a patient such that a portion of the patient is located in a field of view. A longitudinal axis is defined through the field of view. A detector assembly is adjacent the field of view and includes a photon-responsive detector operable to detect if a photon strikes the detector. The detector assembly is operable to detect photons emitted in the portion of the patient located in the field of view. A photon-blocking member is disposed between the field of view and the detector. The blocking member has an aperture slot defined therethrough for passage of photons aligned with the aperture slot. A line of response is defined from the detector through the aperture. A collimating assembly includes a plurality of collimating vanes formed of photon attenuating material. A support assembly supports the collimating assembly. The support assembly includes a first support member and a second support member. The second support member is spaced from the first support member. The collimating assembly is disposed between the support members such that a first distance is defined between the collimating assembly and the first support member and a second distance is defined between the collimating assembly and the second support member. An adjustment assembly includes a first adjuster operable to adjust the first distance and a second adjuster operable to adjust the second distance.

Another aspect of the present invention provides a method for rebinning image data from a radial imaging system, such that the data corresponds to data obtained from a traditional gamma camera of the type obtaining readings while located at a plurality of positions around the field of view. The field of view may be said to have a longitudinal axis defined therethrough. A traditional gamma camera has a sensing face with a central line parallel to the longitudinal axis. The position line is defined perpendicularly between the longitudinal axis and the central line. A sensing plane is defined as containing the position line and being perpendicular to the longitudinal axis. A baseline is defined as perpendicular to the longitudinal axis and contained in the sensing plane. The angular position of the traditional gamma camera is defined as the angle θ between the baseline and the position line. The traditional gamma camera is operable to detect photon strikes in the sensing phase, with each strike in the sensing plane being located at a distance r from the center line. The rebinning method comprises the steps including providing a radial imaging system. The imaging system includes a base with a patient support for supporting a patient such that a portion of the patient is located in the field of view. A generally arcuate detector assembly is adjacent the field of view and includes a photon-responsive detector operable to detect if a photon strikes the detector. The detector assembly being further operable to identify the position of the detector strike along the arcuate detector assembly. A photon-blocking member is disposed between the field of view and the detector. The blocking member has an aperture slot defined therethrough for passage of photons aligned with the aperture slot. A line of response is defined from the detector through the aperture. A collimating assembly includes a plurality of generally parallel collimating vanes formed of photon attenuating material. The vanes are spaced apart so as to define the plurality of gaps. A displacement acuator is operable to move one of the detector and the photon-blocking member relative to the other of the detector and the photon-blocking member such that the aperture is displaced relative to the detector and the line of response is swept across at least a portion of the field of view. Additional steps include obtaining a plurality of detector readings associated with a plurality of photon strikes generally in the sensing plane. Each reading includes an intensity. The position of each reading from the detector assembly is determined, with the position including a radius $R_{det}$ from the center line of the field of view and an angular position, Ψ relative to the baseline. The position of the aperture slot is determined for each reading, with the position including a radius $R_{app}$ from the center line in the field of view and an angular position Ø relative to the baseline. For each combination of r and θ for a traditional gamma camera, the corresponding values of Ψ and Ø are calculated using the following formulas:

$$\phi = \arcsin\left(\frac{r}{R_{app}}\right) - \theta, \text{ and } \Psi = \arcsin\left(\frac{r}{R_{det}}\right) - \theta$$

For each combination of r and θ, the intensity value is stored that is associated with corresponding positions of Ø, Ψ, $R_{app}$ and $R_{det}$. The present invention also provides various approaches to calibrating a single photon emission computed tomography system and apparatus therefore.

According to a further aspect of the present invention, a medical imaging device is provided with a support base and an imaging section for imaging a field of view. The imaging section extends between the fixed end supported by a base and a free end spaced therefrom. The imaging section includes a support assembly having a first support member and a second support member. The support members are spaced apart and each have a fixed end supported by the base and a free end spaced therefrom. A plurality of tension members extend between the first and second support members and are spaced apart between the fixed and free ends of the support members. In some embodiments, the tension members include some that are angled such that one of the ends is closer to the fixed end of the imaging section while others have their other ends closer to the fixed end such that the tension members are angled relative to one another.

BRIEF DESCRIPTION OF THE DRAWINGS

FIG. 1A is a perspective view of a preferred embodiment of the present invention optimized for cardiac SPECT, showing the overall configuration of the system and the positioning of the patient;

FIG. 1B is an additional perspective view of the embodiment of FIG. 1A;

FIG. 20A is a cross sectional top view of one embodiment of a moveable aperture arc extension vane;

FIG. 20B is a view similar to FIG. 20A with the vane shown at a different position;

FIG. 25 is a cross-sectional detailed view of a portion of a sensor module;

FIG. 26 is a front view of an embodiment of a sensor module;

FIG. 28 is a perspective view of a portion of one embodiment of a scintillator-based cylindrical detector module;

FIG. 30 is a perspective view of a detector module with a block of scintillation material with a trapezoidal cross section;

FIG. 31A is a perspective view of a masked detector configuration based on a rectangular shaped piece of scintillation material;

FIG. 31B is a perspective view of a masked detector configuration based on a cylindrical shaped piece of scintillation material;

FIG. 31C is a perspective view of a masked detector configuration based on a piece of scintillation material with a trapezoidal cross section;

FIG. 42 is a sinogram representing data received by a traditional gamma camera;

FIG. 43 is another sinogram representing data for a traditional gamma camera under a different set of conditions;

FIG. 44 is a sinogram representing data from an imaging system according to the present invention;

DETAILED DESCRIPTION OF THE INVENTION

Figure 3:
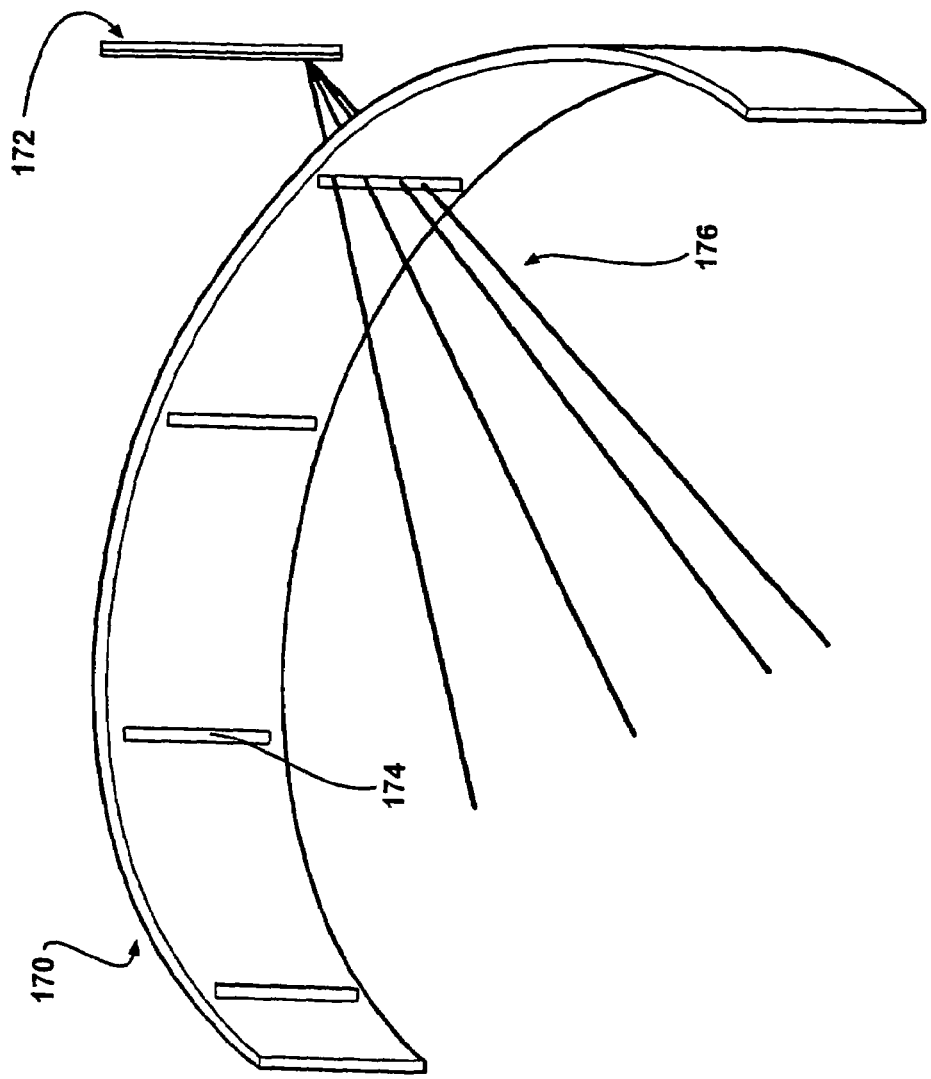
FIG. 3 is a perspective view of an aperture arc for an embodiment of the present invention that is optimized for cardiac SPECT, with a single radiation detection module shown behind the arc to demonstrate relative positioning.

Throughout this description, the preferred embodiment and examples shown should be considered as exemplars rather than as limitations on the present invention.

I. General Overview

One aspect of the present invention comprises a system for performing single photon emission computed tomography (SPECT). This system includes a radiation detector assembly consisting of a multiplicity of radiation detector modules preferably positioned around an arc, typically over 180 to 360 degrees. In-plane (axial) collimation is provided by a movable arc or ring extending over an angular range similar to that of the radiation detector assembly (typically 180–360 degrees). Cross-plane (longitudinal) collimation is provided by a plurality of vanes or sheets of photon-attenuating material held in a stationary position and oriented parallel to the transaxial plane (perpendicular to the longitudinal axis). Optionally, these vanes may be separated by sheets of a radiolucent spacer material such as Styrofoam® or other plastic. Some embodiments of the present invention also include a patient chair or support structure.

II. Discussion of Chair, Arc Configuration, and Patient Positioning

FIGS. 1A and 1B illustrate a preferred embodiment of the present invention optimized for cardiac SPECT, showing the overall configuration of the system 100 and the positioning of the patient 102. The opening 104 for patient entry and egress is shown. The imaging section 106 of the system extends as an arc over the right side of the patient's chest. The imaging section consists of a lead shielded housing with internal components as described below. The imaging section is supported by a stand 108 affixed to a base 110. Together, the rear portion of the imaging section and the stand form the "back" of the patient support. The patient is seated upon an adjustable seat 112. The vertical height of this seat may be adjusted so as to position the patient's heart within the appropriate portion of the imaging device. Such adjustment may be performed by means of electrical motors, hydraulic devices or other means. The seat is optionally adjustable so as to swivel horizontally, thus easing patient entry and egress from the seated position. The stand and base may also include or support the electronics necessary for processing scans, as well as any necessary controls or displays.

As shown, unlike in the prior art systems, the patient is seated generally upright so that their torso is generally vertical. The lighter weight, simpler design, and reduced bulk of the present system cooperate to allow this positioning. For definitional purposes, the area surrounded by the imaging section 106 will be referred to as a field of view. Also for definitional purposes, it may be said that a longitudinal axis, generally aligned with the longitudinal axis of the patient's torso, extends through the field of view. It may be said that the longitudinal axis is generally vertical to distinguish the positioning of the present system from the typical systems where the patient is forced into a horizontal position. In actuality, the generally vertical longitudinal axis may be reclined somewhat, as shown, to increase patient comfort.

As will be clear to those of skill in the art, it is very important to image the appropriate portion of the human patient, in order to acquire data about the portion of the patient that is of particular interest. For example, the preferred embodiment of the present invention is designed to image the patient's heart. Therefore, it is important that the portion or slice being imaged includes the patient's heart. However, the exact position of the patient's heart within their chest is not always easily determined from an external exam. In prior art systems, the patient is positioned in front of the detector(s) while the operator views a low-resolution, two-dimensional display known as a persistence-scope (p-scope). The persistence scope image is necessarily of low quality due to its need to be continually updated as the patient is repositioned and due to the two-dimensional nature of its images. Operator error in patient positioning is not uncommon and, when it occurs, results in a useless scan. According to another aspect of the present invention, a cardiac scan may be preceded by a "quick scan" of the patient's chest so as to properly locate the heart so as to adjust the position of the chair so that the heart is properly positioned for imaging by the imaging section 106.

The "quick scan" is possible with the present invention for several reasons, which will become clear after reviewing the entirety of this specification. Systems of the present art must partially orbit the patient in order to acquire three-dimensional imaging. Movement of the large, heavy (typically 450–500 pound) detectors must be started and stopped within seconds if rapid three-dimensional positioning images are to be obtained. This is both mechanically difficult and may present a hazard to the patient from the rapid movement of large and heavy detectors. The present invention requires the movement of only an aperture arc to image the portion of the patient in the field of view of the imaging section 106. The aperture arc is preferably hidden from the patient inside a housing, and can be moved much more quickly and safely than can prior art gamma camera. Also, a full scan requires the arc to move only a short distance, unlike a gamma camera where the camera has to move a long distance. In addition, the present invention acquires image data more quickly than prior art devices. Therefore, a fast, low count, three-dimensional image may be acquired by quickly moving the aperture arc within the housing. This low count image may be reconstructed almost instantly with state-of-the-art computers and displayed immediately as slices, or preferably, as rotating surface rendered or maximum-intensity-projection images. Such volume-rendered images clearly reveal the underlying patient anatomy and may be used to reliably determine the position of the heart prior to the start of routine, high count imaging.

In embodiments of the present invention wherein the seat 112 is adjustable upwardly and downwardly, the chair position may be optionally adjusted between two image acquisitions so as to adjust the positions of the slices being imaged. In some embodiments, the movement may be very slight, so as to compensate for effects of the collimators, which are discussed in more detail hereinbelow. The chair position may also be adjusted upwardly or downwardly during an image acquisition.

As known to those of skill in the art, patient movement during imaging is a significant problem for most imaging systems. Most systems require the patient to lie on a narrow horizontal surface, in a rather uncomfortable supine or prone position. This position is often uncomfortable for patients with back problems or for the many cardiac patients that have difficulty breathing when lying flat. Often, this results in patient movement during the scan. In order to accommodate the moving detectors of current art systems, the patient must hold their arms over their head for the duration of the imaging procedure. This is quite uncomfortable for many patients, particularly those with arthritic shoulders. Many patients experience fear or claustrophobia when lying under the large, metal detectors of current devices. Patients who are uncomfortable or fearful typically adjust their position in an attempt to become more comfortable. Such movement, when it occurs during an image acquisition, causes image artifacts, which may cause incorrect findings and subsequent treatment. The problem is exacerbated by long scan times. The vertical positioning of a patient enabled by the present invention, as illustrated in FIGS. 1a and 1b, significantly improves patient comfort and stability. It is much more comfortable for back and cardiac patients. The arms do not need to be held over the head. The open design of the present invention eliminates claustrophobia. Consequently, patient comfort and security is increased and movement is reduced. Also, some embodiments of the present invention allow significantly reduced scan times, thereby reducing the effects of patient motion.

III. General Discussion of 1-Dimensional Solid State Detector Modules (Strips)

Figure 2:
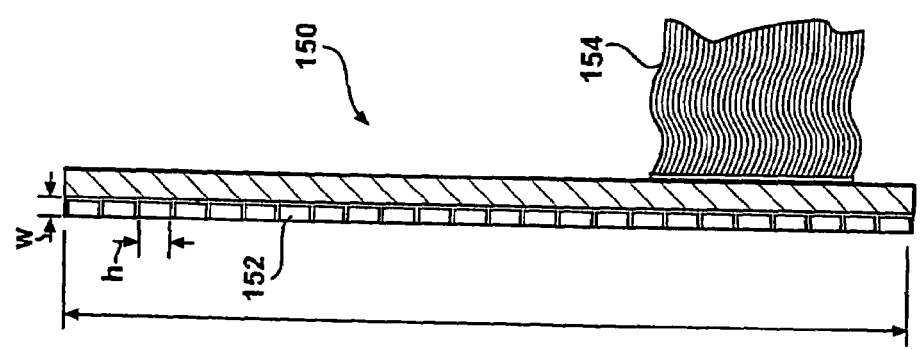
FIG. 2 is a perspective view of one embodiment of an individual detector module for detecting photons during SPECT imaging.

FIG. 2 shows one embodiment of an individual detector module 150. Multiple (typically 64) individual modules are arranged in an arc surrounding the patient. The arc may extend over a range of approximately 180 to 360 degrees. For cardiac SPECT, a preferred embodiment is approximately 180 degrees. The embodiment shown is a solid-state detector module sized for cardiac imaging. Other detector module embodiments are discussed below. As shown, the detector module 150 is an elongated strip. Rectangular regions on the face of detector indicate an array of individual solid-state detector elements 152, each comprising one pixel for data acquisition. In this embodiment, the array of detector elements is one-dimensional, i.e. 1×N, although two-dimensional arrays may also be employed. Multiconductor ribbon cable 154 carries electrical signals from the detector elements to the electronics that process the signals. Alternatively, some of the processing circuitry may be integral with or packaged by the detector elements.

Each detector element 152 is operable to detect if a photon strikes it. Therefore, the overall detector 150 is operable to detect if a photon strikes and is also operable to determine where along its length the photon struck. Each detector element includes some semiconductor material, such as cadmium-zinc-telluride, with an electrode applied to opposing surfaces. An electrical potential is applied across the electrodes. As will be clear to those of skill in the art, when a photon passes through the front electrode and interacts with the semiconductor material, a small current travels between the electrodes. This current is measured to sense the impact of photons.

While the present invention is initially described as using the above-described detector elements, other embodiments of the present invention make use of other detector designs, as will be described in more detail herein below.

IV. Aperture Arc—General Discussion

FIG. 3 shows the aperture arc 170 for an embodiment of the present invention optimized for cardiac SPECT. A single radiation detector module 172 is shown behind the arc to demonstrate relative positioning. As shown, the detector module is generally parallel to the longitudinal axis. The arc 170 serves as a photon-blocking member and may be made of lead or a similar high attenuation material. The arc 170 is of sufficient height to cover the radiation detection modules 172 situated behind it. The arc is of sufficient thickness (typically approximately 3 mm) so as to effect essentially complete absorption of photons emitted by the patient. The arc is penetrated by a series of vertical aperture slots 174 which permit photons 176 aligned with the aperture slot to pass from the patient through the slot to reach the detector modules. The slots are preferably generally parallel to the longitudinal axis of the patient.

Figure 4:
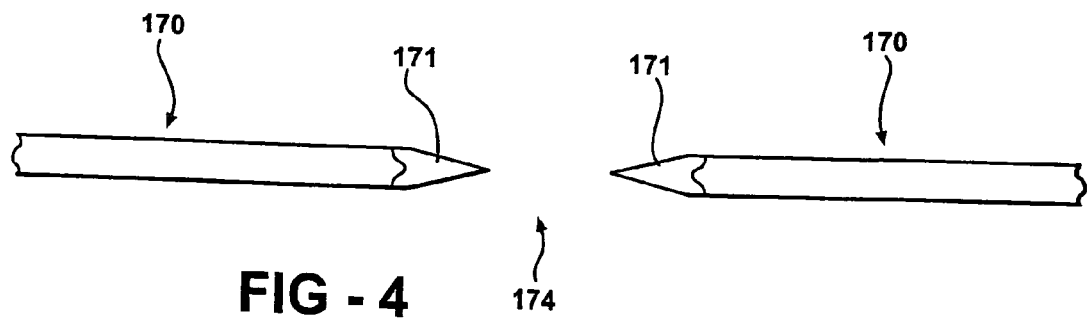
FIG. 4 is a cross-sectional detailed view of a small portion of an aperture arc, showing details of one embodiment of an aperture edge treatment.
Figure 5:
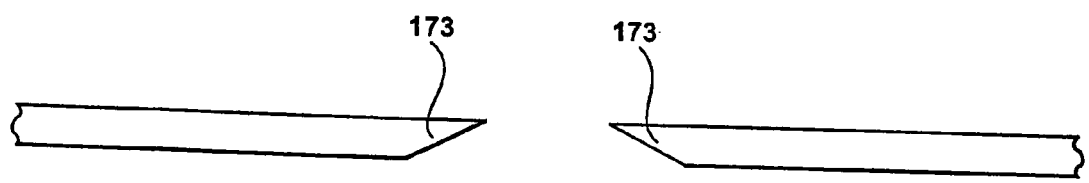
FIG. 5 is a cross-section detailed view similar to FIG. 4, showing an alternative embodiment of an edge detail.
Figure 6:
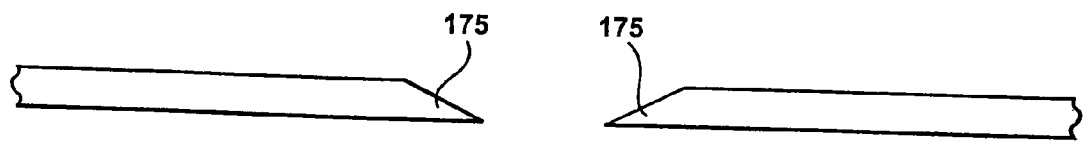
FIG. 6 is a detailed view similar to FIGS. 4 and 5, showing yet another alternative embodiment of an edge detail.

In FIG. 3, the arc 170 is shown as a continuous member with generally rectangularly shaped slots cut therethrough. In some embodiments, the slots are cut straight through, and have sides that are parallel to one another. Alternatively, the slots may be cut with angled sides such as shown in FIGS. 4–6. Each of these Figures illustrates a cross-section of the slot taken generally perpendicular to the slot. FIG. 4 illustrates an embodiment wherein the arc 170 has tapered ends 171. The arc 170 may be said to have a pair of opposing surfaces. The tapered points 171 taper from each of these opposing surfaces to a point at approximately the center plane of the arc. For simplicity, FIGS. 4–6 illustrate a portion of the arc as being generally linear. However, as previously discussed, it is actually arcuate.

Preferably, the arc 170 blocks substantially all of the photons except those that pass through the slot 174. A certain thickness of photon blocking material, such as lead, is required to adequately block these photons. The tapered points 171 are thinner than the remainder of the arc. Therefore, it is preferred that they are formed out of a material that has even higher photon blocking ability, such as tungsten or gold, but could be lead. These tapered points 171 are joined to the material that typically forms the remainder of the arc 170. Alternatively, the arc, including the edges, could be all one material, such as lead. FIGS. 5 and 6 illustrate alternative embodiments of tapered points 173 and 175. In these embodiment, the edges of the slots taper either from the front to the back or from the back to the front. As with the embodiment of FIG. 4, the points are preferably formed out of a material with a higher photon blocking ability than the remainder of the arc. The pointed edges of the slot are preferred, as they provide a more consistent apparent edge of the slot, independent of the angle from which it is viewed. That is, a slot with squared-off edges may appear substantially narrower when viewed from an angle. By tapering the edges of the slot, the slot has a more consistent effective width when viewed at a shallow or deeper angle. This is especially important in the design of the present invention since radiation may enter the aperture at a significant angle. Alternatively, the "points" may be rounded.

Figure 7:
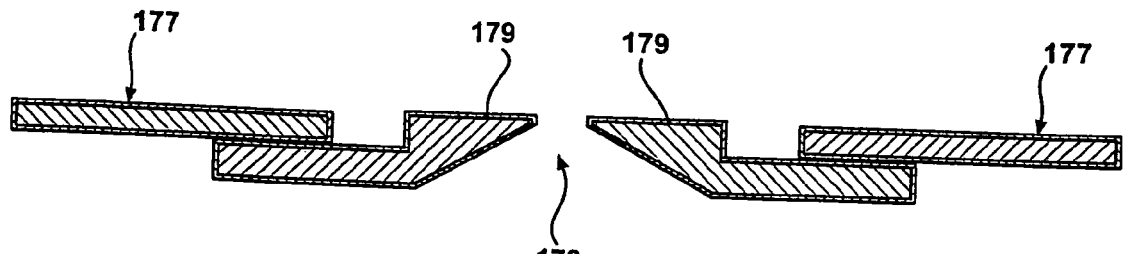
FIG. 7 is a cross-section detail of a portion of an aperture arc, including adjustable end pieces for providing an aperture with an adjustable width.
Figure 8:
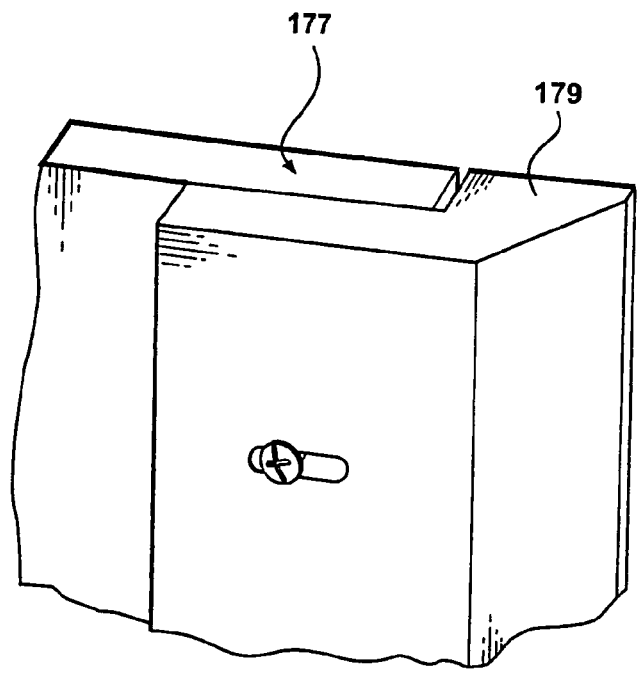
FIG. 8 is a perspective view of a portion of an aperture arc and one adjustable end piece.

In some embodiments of the present invention, it is preferred to have slots with adjustable widths. This allows adjustment in the sensitivity and resolution of the imaging system. It may also assist in calibration. FIGS. 7 and 8 illustrate one approach to providing slots with adjustable widths. FIG. 7 illustrates a cross-section of a portion of an arc 177 with adjustable slot defining pieces 179 attached thereto. FIG. 8 shows a perspective view of one portion of an arc 177 with one adjustable piece 179. By adjusting the positions of the pieces 179 relative to the remainder of the arc 177, the relative position and width of the slot 178 may be adjusted. As with the embodiments of FIGS. 4–6, the thinner portions of the end pieces 179 are preferably formed from a material with a higher photon blocking capability than the remainder of the arc 177. The end pieces 179 are illustrated as having a front-to-back taper, but may have any of the shapes illustrated in FIGS. 4–6, or may provide a more squared-off or rounded-off edge to the slot. Also, the end pieces 179 are not required to be symmetrical. Additionally, a single adjustable piece may be provided for each slot, with the other side of the slot being defined by a non-moveable edge. As will be clear to those of skill in the art, the interconnection between the end pieces 179 and the arc 177 may be provided in a variety of ways, other than the approach illustrates. Adjustment of the slot width may also be achieved in other ways, as will be clear to those of skill in the art.

V. Field of View

Figure 9B:
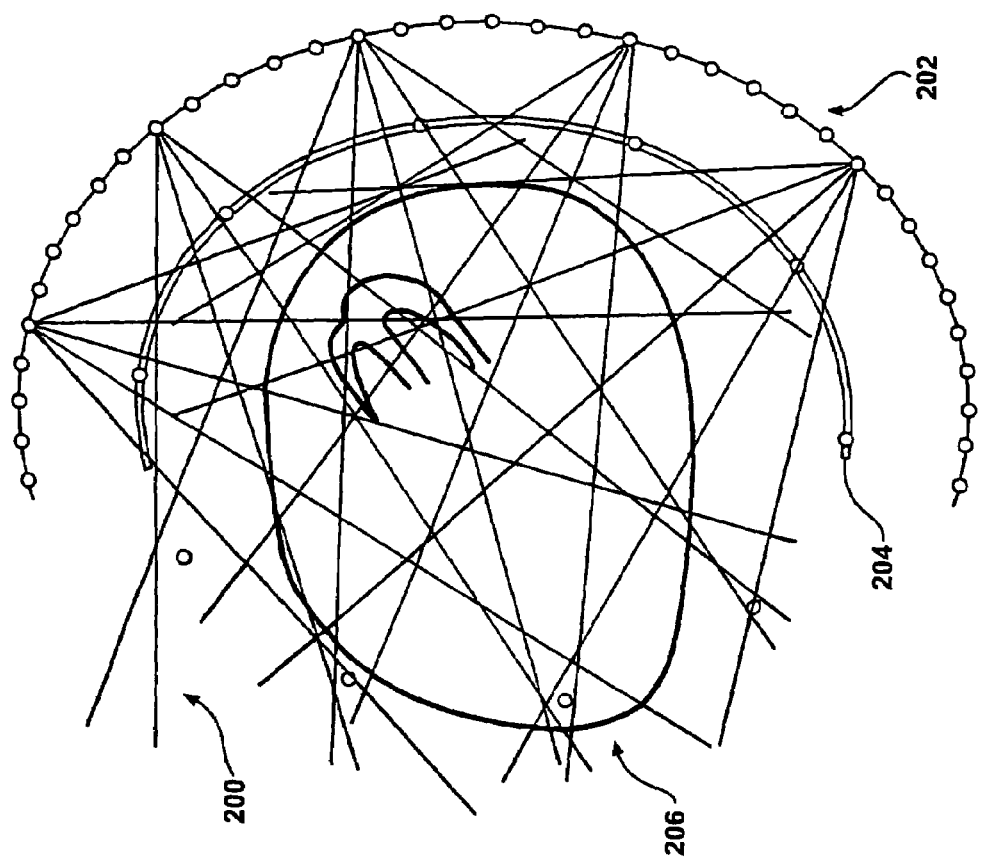
FIG. 9B is a diagrammatic top view showing how lines of response of the individual detectors provide multiple angular projections through the body.
Figure 9A:
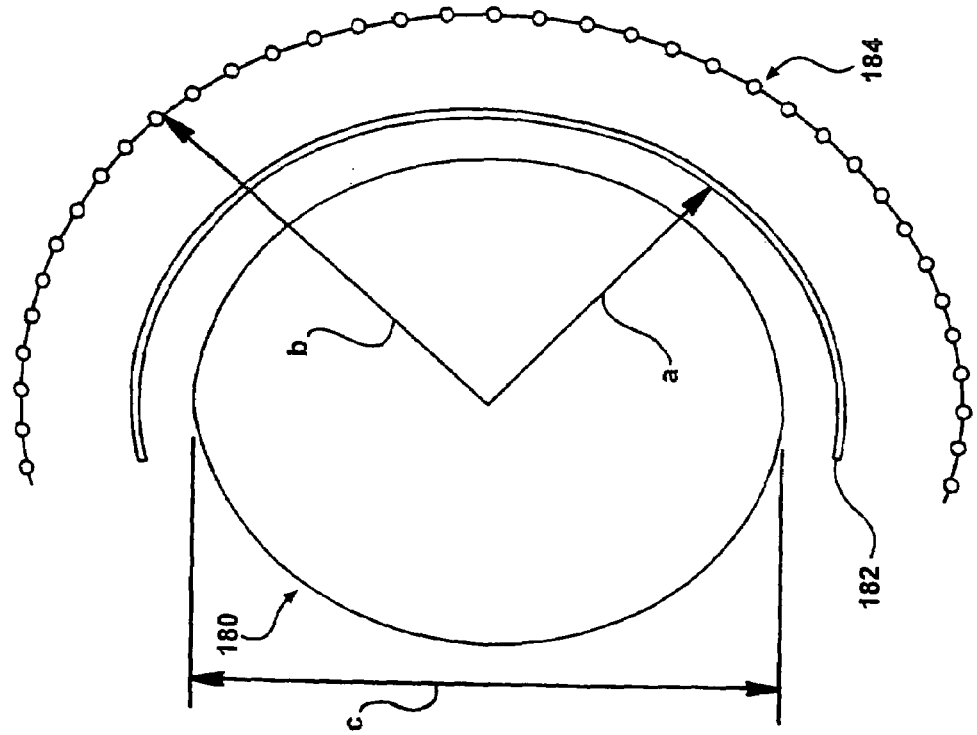
FIG. 9A is a diagrammatic top view showing the relative positions of the slotted aperture arc, the arc of detectors and the patient field-of-view.

FIG. 9A diagrams (from above) the relative positions of the patient field-of-view area 180, the aperture arc 182 and the detector modules 184. It may be seen that the set of detector modules and the aperture arc are situated concentrically around the patient. One embodiment for cardiac imaging includes approximately 64 radiation detector modules 184, each consisting of an array of individual elements or pixels. In this embodiment, the aperture arc 182 is positioned at a radius, a, of approximately 30 cm and the detector modules 184 are positioned at a radius, b, of approximately 40 cm. A patient field-of-view area with a diameter, c, of approximately 50 cm fits easily within the arc 182. The aperture arc 182 and/or the set of detector modules 184 may be arranged in a true geometric arc with common arc centers at the longitudinal axis. Alternatively, either or both may be more ovalized or be arcuate with non-shared arc centers. For example, the arc centers may be positioned away from the longitudinal axis so as to increase the arc radii. It is also possible for the arc 182 and/or the set of modules 184 to be non-arcuate. For example, either could be arranged as a series of short straight segments, or be partially arcuate and partially non-arcuate. Another example would be if either had different arc radii at different radial positions so that the radius of curvature changes along the "arc".

Displacement means is provided for moving the aperture arc 182 relative to the detectors 184. As will be clear to those of skill in the art, many different approaches may be used to move the aperture arc. For example, the aperture arc 182 may be connected by a worm gear or other arrangement to a motor such that it can be rotated through a limited angle about the longitudinal patient axis. As will be clear to those of skill in the art, the arc may remain stationary with only the detectors moving. However, this approach is generally more complicated and costly. For purposes of processing the information from the scan, means are also provided for accurately determining the position of the arc. As will be clear to those of skill in the art, many approaches to providing this means are available, including optical encoders and mechanical sensors. The sensing means may also be used for feedback control of the displacement means. A more detailed discussion of one approach to moving an aperture arc will be provided hereinbelow.

VI. Discussion of Sweep due to Aperture Arc movement

Figure 10A:
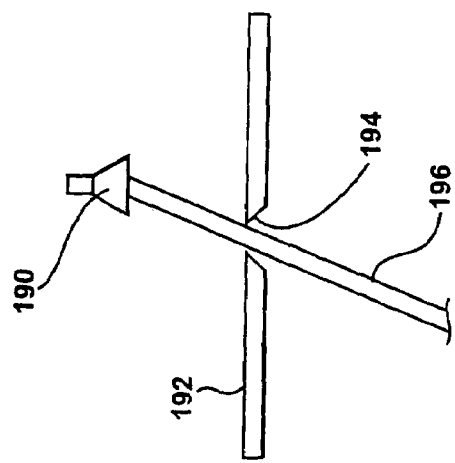
FIG. 10A is a top schematic view of a single detector module and a small section of the aperture arc at a first rotational position of the aperture arc.
Figure 10B:
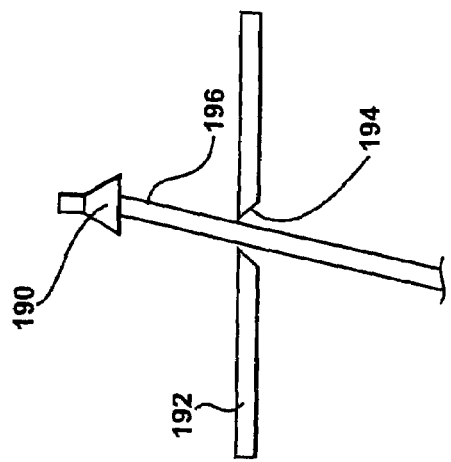
FIG. 10B is a view similar to FIG. 10A but with the aperture arc at a second position.
Figure 10C:
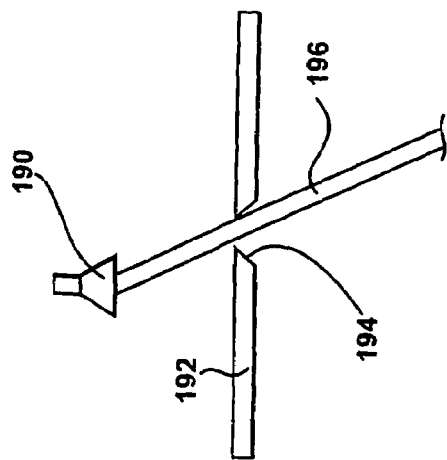
FIG. 10C is a view similar to FIGS. 10A and 10B but with the aperture arc at a third position.

FIGS. 10a–c show overhead views of a single detector 190 and a small section 192 of the aperture arc. The Figures illustrate the relative position of the arc 192 and the detector 190 at three different rotational positions of the aperture arc 192. At each position, the position of the aperture slot 194 restricts the line of response of the detector to a particular path 196, as shown. It can be seen that, as the aperture slot 194 moves in front of the detector 190, the line of sight of the detector fans across the patient, generating a multiplicity of lines of response or projections.

Since, as diagrammed in FIG. 9A, there are a multiplicity of detector modules 184 and, as shown in FIG. 3, a multiplicity of aperture slots 174, a multiplicity of detector lines of response are formed at each rotational position of the aperture arc. FIG. 9B illustrates a small subset of the lines of response 200 obtained from a few of the detectors 202 as the aperture arc 204 is rotated. The aperture slots themselves are not shown in this Figure, for simplicity. A diagrammatic "slice" 206 through the patient's chest is shown, indicating that a full set of projections of the heart, sufficient for tomographic reconstruction, is obtained in this manner.

The aperture arc preferably moves continuously, such that the lines of response "sweep" over the field of view. Alternatively, the aperture arc may move in discrete steps, with imaging occurring with the arc stopped at each of the steps.

VII. Each Detector Illuminated by only a Single Aperture Slot

All detectors preferably "look through" only one slot at all times. Slot spacing is determined such that each detector is illuminated by only one slot at a time. Overall photon detection efficiency is proportional to the number of slots in the aperture arcs. The maximum number of slots permissible, $n_{slots}$, is a function of the angle $\phi_{arc}$, representing the maximum angel of incidence of a usable ray at an aperture slot, the radius of the detector arc and the minimum length of arc on the aperture arc such that a given length of arc $\theta_A$ on the aperture arc such that a given detector will only see the patient field-of-view through one slot at a time ($\theta_A$)):

$$n_{slots} = \frac{\pi \cdot \frac{\phi_{arc}}{2\pi}}{\frac{\theta_A}{2}} = \frac{\pi \cdot \frac{\phi_{arc}}{2\pi}}{\sin^{-1}\left(\frac{R_O}{R_A}\right) - \sin^{-1}\left(\frac{R_O}{R_D}\right)}$$

where $R_O$ is the radius of the patient, $R_A$ is the radius of the aperture arc and $R_D$ is the radius of the detector arc. The aperture arc need only be rotated by the interval between slots, $\phi_{arc}/n_{slots}$, to provide a full set of angular projections.

For one embodiment of the present invention, the radius of the patient $R_O$, is assumed to be a maximum of 22 cm, the radius of the aperture arc $R_A$, is 30 cm and the radius of the detector arc, $R_D$, is 45 cm. The detector arc and aperture arc span an angle, $\phi_{arc}$, of 180 degrees and the minimum length of the arc, $\theta_A$, is 36 degrees. For these values, the equation provides that five slots are the maximum number of slots to avoid any detector looking through more than one slot at a time. Consequently, the aperture arc need only rotate through an angle of 36 degrees to provide a full set of angular projections.

The above equation and solution assumes that the slots are equally spaced along the arc, and separated by an angle of 36 degrees. As will be clear to those of skill in the art, the critical issue is actually the angular separation between the slots, which determines the number of slots. Referring again to FIG. 3, the arc is shown with five slots, one which is hidden in the bend, due to the angle of view in the Figure.

Figure 11A:
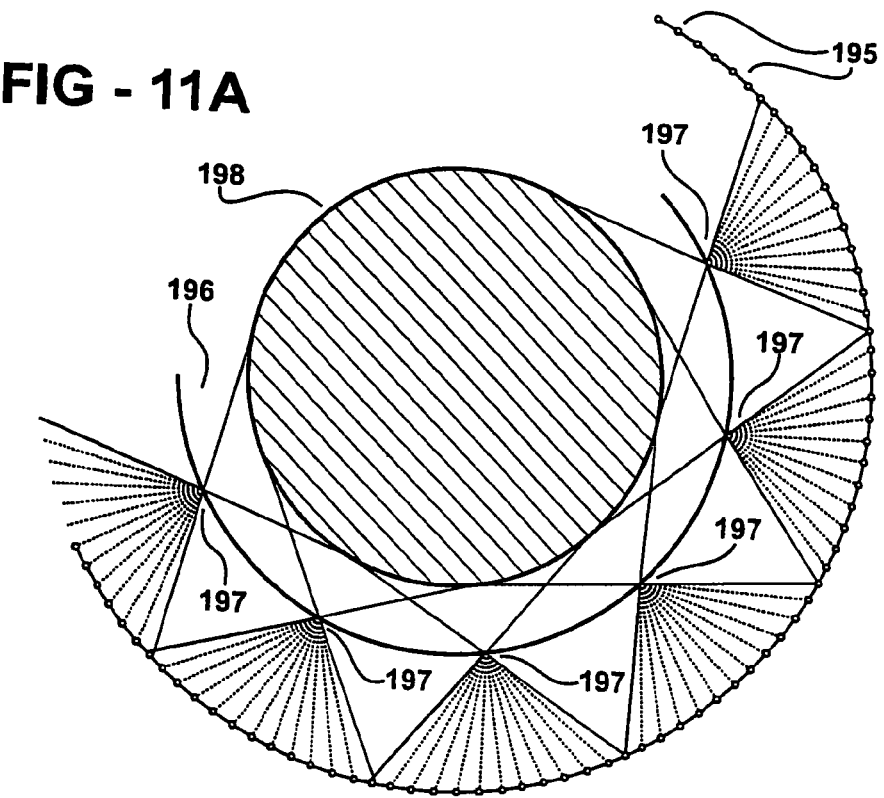
FIGS. 11A–F are a series of diagrammatic top views of the present invention.
Figure 11B:
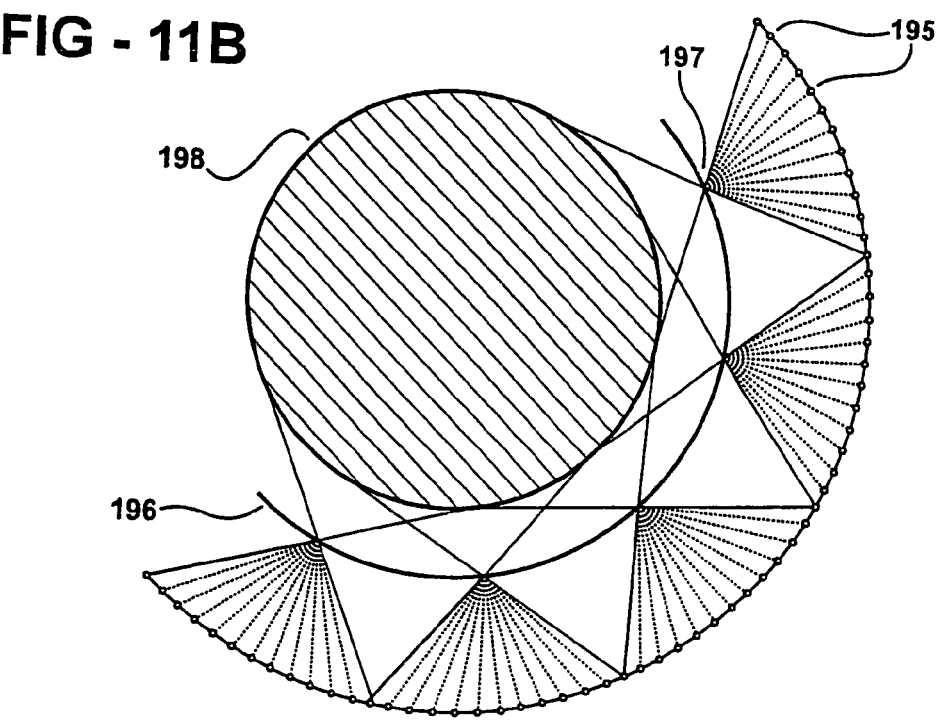

While the above equation and discussion leads to the conclusion that 5 slots are needed, with a separation of 36 degrees between the slots, the addition of a 6$^{th}$ slot is beneficial. FIG. 11A diagrammatically illustrates the present invention with a plurality of detectors 195 disposed in an arc, an aperture arc 196 with five apertures 197, and a field of view 198. The arc 196 is shown at the extreme clockwise position. Assuming photons of interest may originate from anywhere in the field of view, projection rays are drawn to show how the field of view is "projected" onto the arc of detectors 196. As shown, some photons are projected to a position clockwise of the last detector, and therefore do not contribute to the image. Likewise, a number of the detectors at the counterclockwise end are "out of view" of the aperture at the counterclockwise end of the aperture arc 196, and are therefore unexposed with the arc in this position. Unexposed detectors represent a less-than-optimal system efficiency FIG. 11B illustrates the aperture arc at the midpoint of its travel. As shown, at this position, the projections through all apertures 197 coincide with the positions of the detectors 195, so that no photons are wasted and no detectors are unexposed.

Figure 11C:
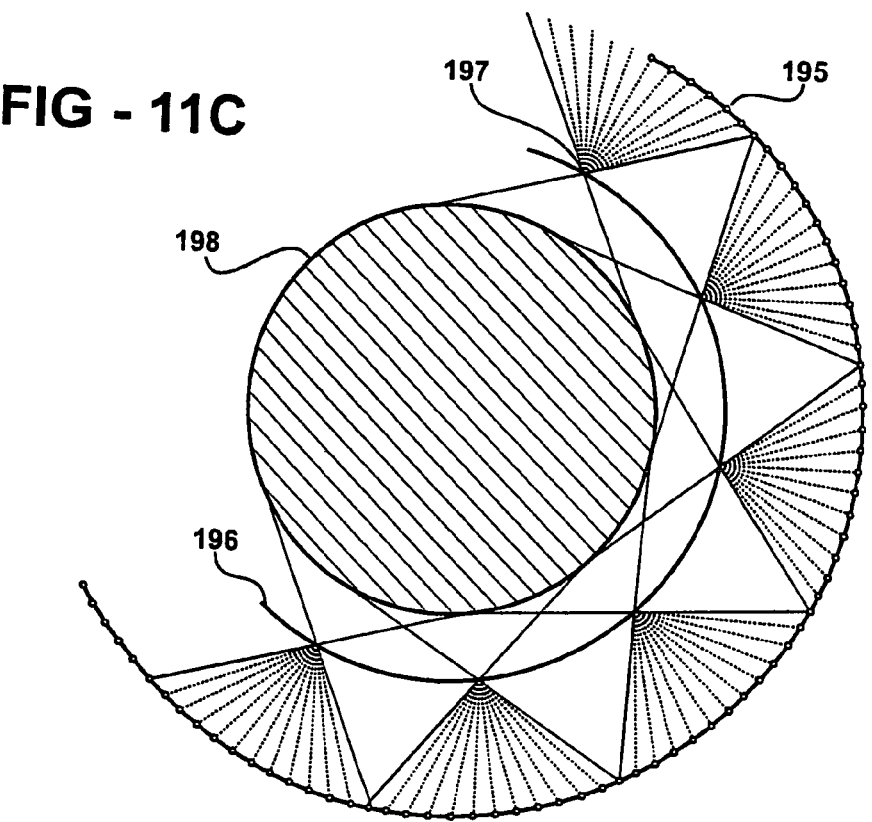

FIG. 11C illustrates the aperture arc 196 at the extreme counterclockwise position. In this position, detectors at the clockwise end of the detector assembly are unexposed, and some photons passing through the apertures at the counterclockwise end go undetected.

Figure 11D:
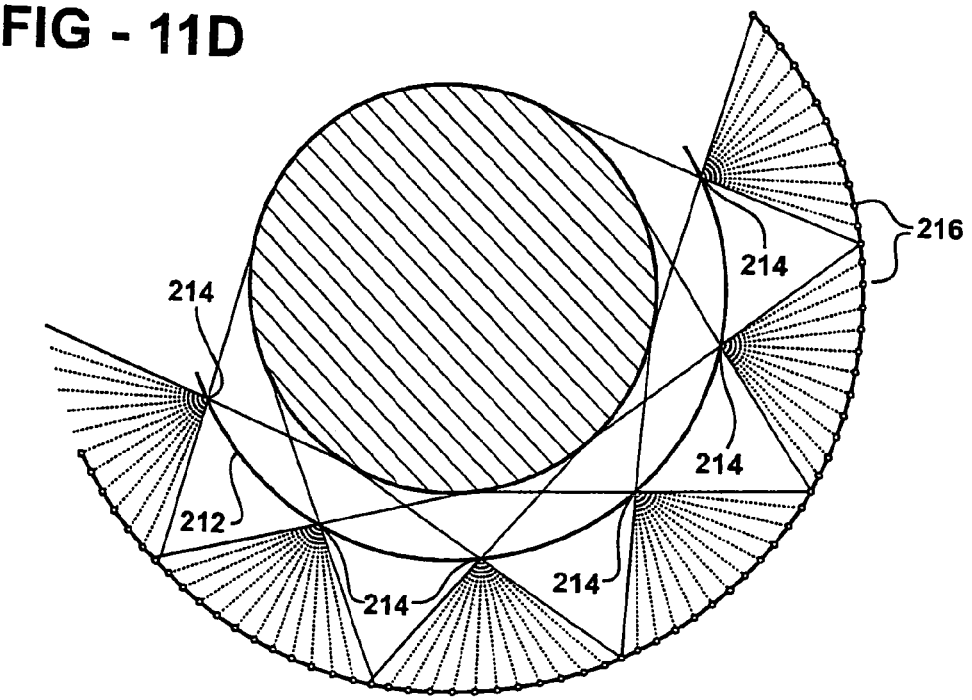
Figure 11E:
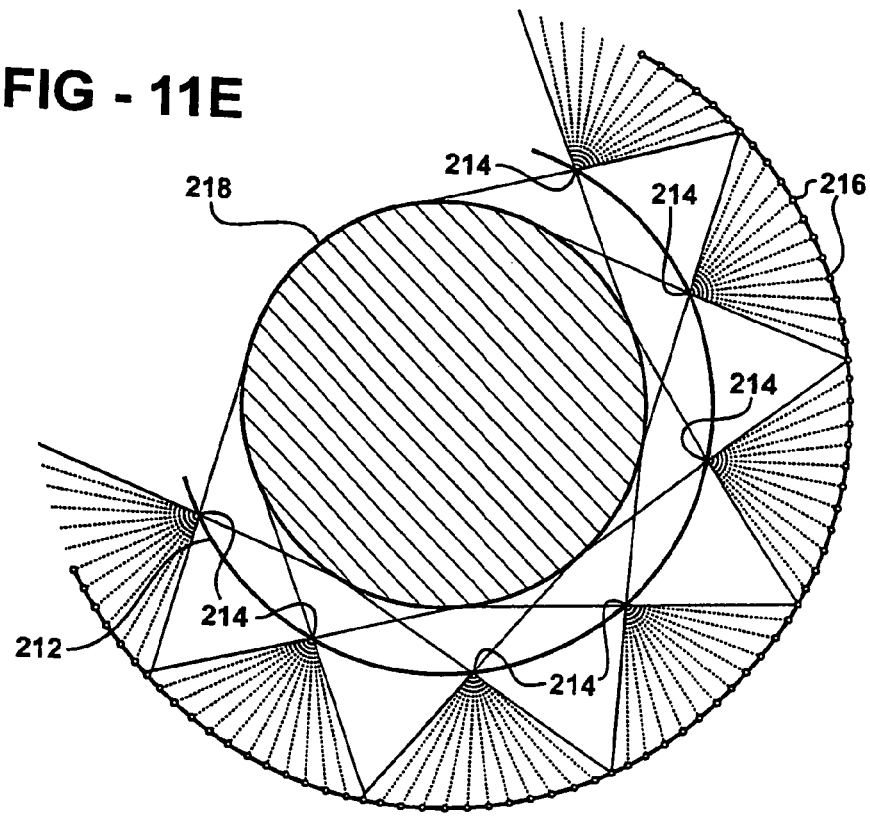
Figure 11F:
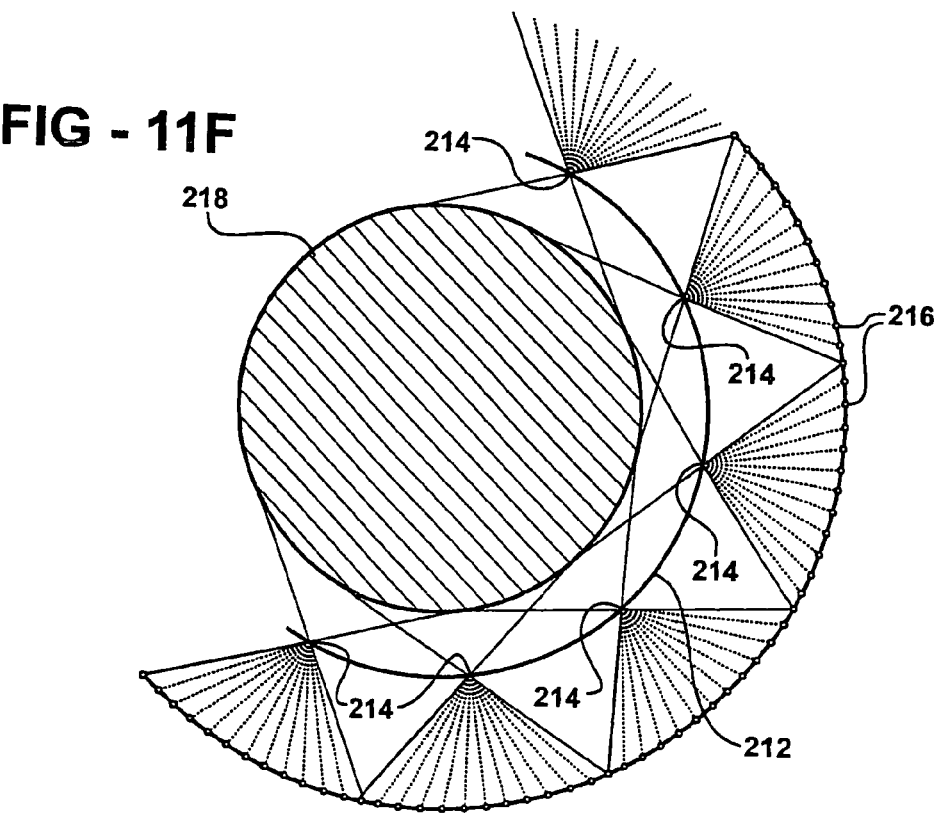

One solution to this problem is to provide a larger number of detectors. However, the increases the size of the imaging section, and dramatically increases the cost of the device. A preferred solution is illustrated in FIG. 11D. The aperture arc 212 now has 6 slots 214 projecting photons onto the detectors 216, from the field of view 218. The spacing between these slots is unchanged, however, from that determined by the equation above (36 degrees in this example). FIG. 11D illustrates the arc 212 at the extreme clockwise position. As shown, all detectors are illuminated due to the addition of the sixth slot. FIG. 11E illustrates the arc 212 at the midrange of travel, and FIG. 11F illustrates the arc at the extreme counterclockwise position. Again, all detectors 216 are illuminated at all positions, thereby increasing photon collection efficiency. The addition of the "extra" slot, results in a perfect match of incoming photons to the length of the arc of detectors. In this arrangement, all detectors are illuminated via the aperture slots at all times, thereby optimizing photon detection efficiency.

VIII. Diagonal Apertures

Figure 12:
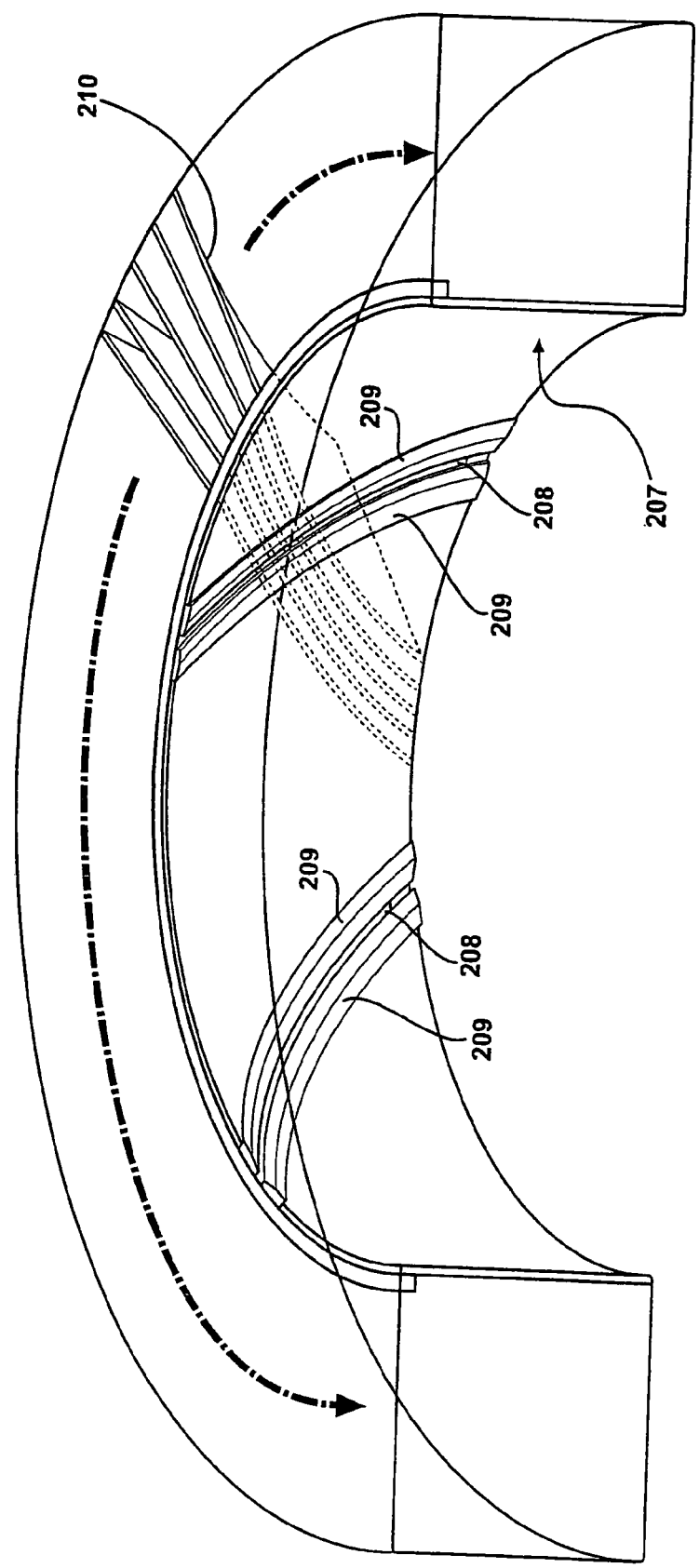
FIG. 12 is a partially transparent perspective view of an alternative embodiment of an imaging section for the present invention, including aperture arcs and collimator vanes that are angled.

Referring again to FIG. 3, the slots 174 are shown as generally vertical slots. That is, they are parallel to the longitudinal axis of the field of the view. According to further aspects of the present invention, the slots may be diagonal as shown in FIG. 12. FIG. 12 illustrates an assembly including an aperture arc 207 with diagonal apertures 208 defined therethrough. The diagonal apertures are illustrated as being defined by adjustable side pieces 209, but may alternatively be provided by slots cut into the arc 207. Also, as with the earlier embodiments of slots, the slot edges may be tapered in a variety of ways, including any of the previously disclosed shapes. As will be clear to those of skill in the art, multiple apertures are preferred, arranged in intervals along the arc 207. Only two apertures 208 are illustrated in FIG. 12, for simplicity. However, additional apertures are preferred. FIG. 12 illustrates additional aspects of the present invention, which will be discussed hereinbelow with respect to collimator design. The angled slots or apertures 208 may be provided at a variety of angles ranging from slightly angled from "vertical," to nearly horizontal. As a further alternative, the slots may be completely "horizontal" with respect to the patient axis. The apertures may also be angled in the opposite direction to the angle illustrated in FIG. 12.

In embodiments of the present invention where the apertures are "vertical" and the collimators are horizontal, or vice versa, the resolution is different in the vertical and horizontal directions. According to one preferred embodiment of the present inventions, the apertures are angled at approximately 45 degrees one direction, and the collimators are angled at approximately 45 degrees the other direction. By angling the apertures and the collimators relative to the transaxial imaging plane, the overall resolution experienced at the imaging plane is made essentially isotropic, i.e. similar in all directions. This is desirable in some applications, particularly if the reconstructed date is to be reformatted along obliquely angled planes.

IX. Collimators

Figure 13:
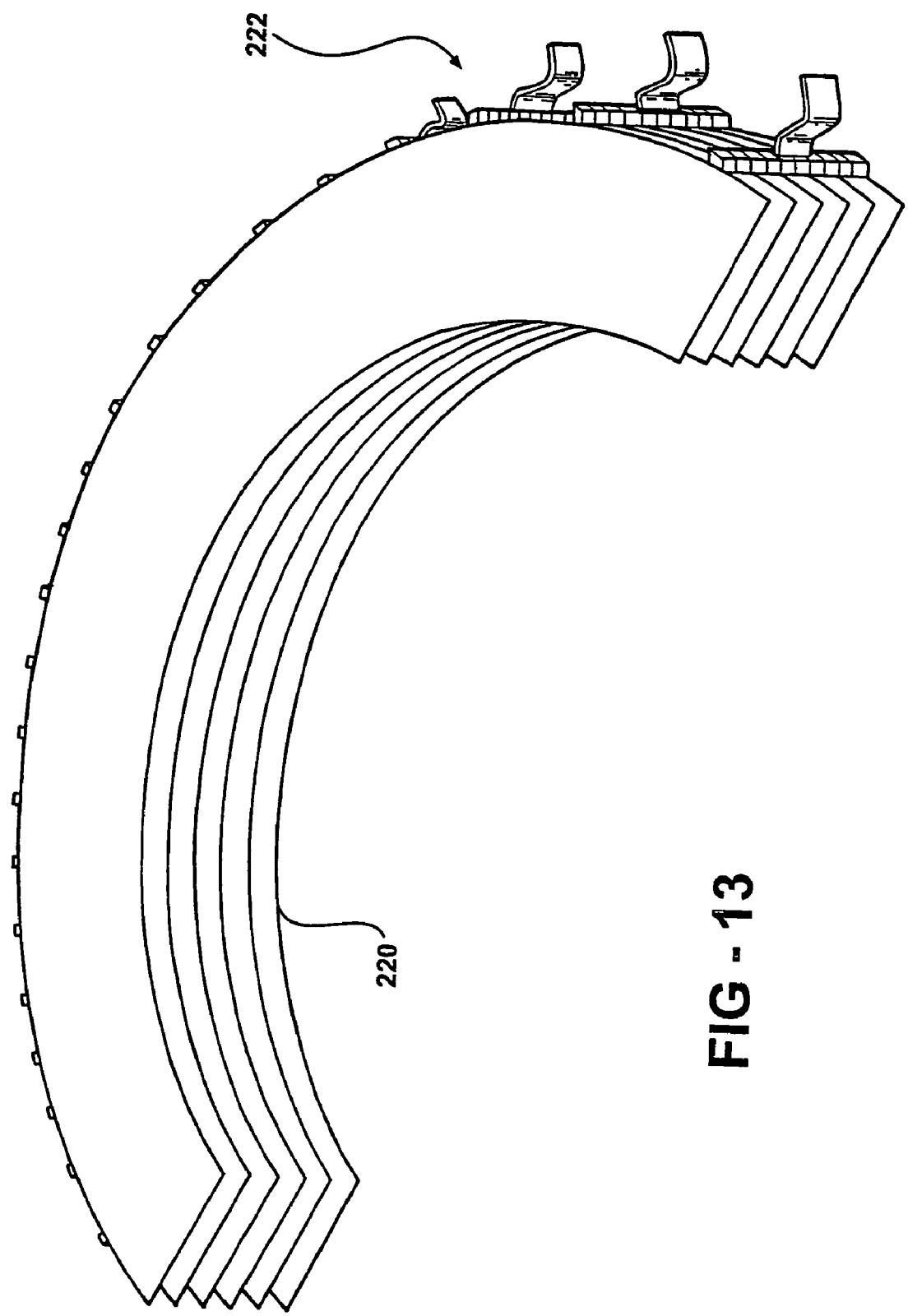
FIG. 13 is a perspective view of a cross-plane (longitudinal) collimation assembly showing its relationship to the detector modules.

Referring again to FIGS. 3 and 11A–F, the aperture arc and the set of detectors provide projection data collimated within the transaxial plane, but not collimated longitudinally. For this reason, the invention preferably provides a set of longitudinal or cross-plane collimators, as shown in FIG. 13. As will be clear to those of skill in the art, the collimator design illustrated in FIG. 13 is designed for use with the "vertical" aperture arc, such as shown in FIG. 3. The longitudinal collimators consist of a stack-like series of arc-shaped vanes 220 arranged as shown and located concentrically to the arc arrangement of detectors 222 as shown. The aperture arc is omitted from this figure, but is located concentrically to the longitudinal collimator vanes. The vanes are preferably mutually parallel and generally perpendicular to the longitudinal axis of the patient. The vanes are sheets or panels of lead or similar attenuating material and may be separated by spacers of radiolucent plastic foam or similar material (not shown). The number, size, and thickness of the vanes may be varied depending on the application.

Figure 14:
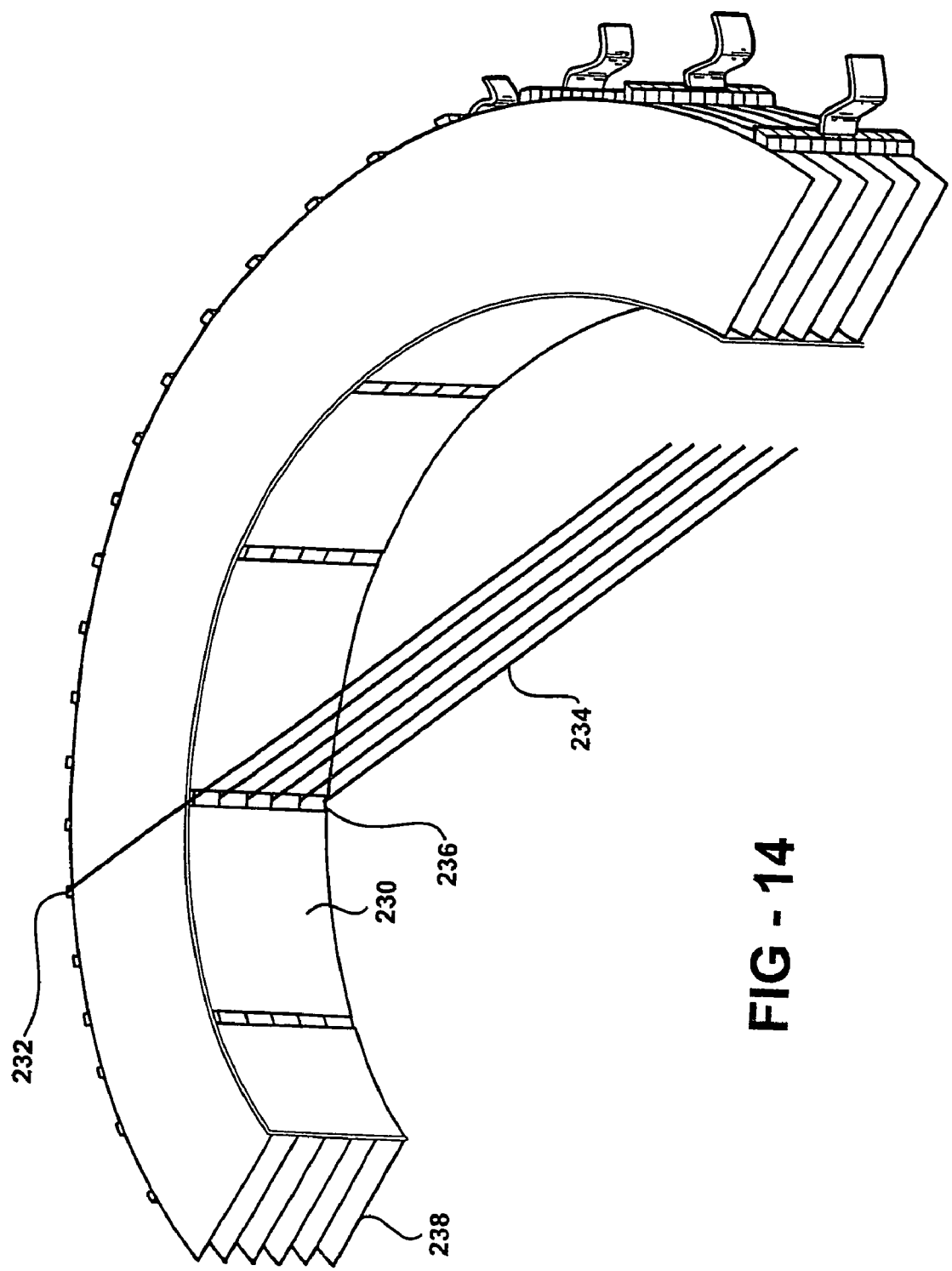
FIG. 14 is a view similar to FIG. 13 but including the aperture arc and showing the lines of response from one detector module.

FIG. 14 is similar to FIG. 13 but with the addition of the aperture arc 230. It may be seen that each individual detector element (pixel) of each detector 232 has a unique line-of-response 234 directed into the patient field-of-view by the combined collimating effects of the aperture arc slots 236 and the longitudinal collimating vanes 238.

As will be appreciated by those of skill in the art, it is preferred that the vanes 220 be provided in a plane that is generally perpendicular to the apertures in the aperture arc. In the embodiment of FIGS. 13 and 14, collimators vanes may be considered to be "horizontal," since they are perpendicular to the "vertical" patient axis. Referring again to FIG. 12, it can be seen that the collimators 210 are angled so as to be generally perpendicular to the angled aperture. Only five collimating vanes 210 are illustrated in FIG. 12, in order to avoid cluttering the drawing. However, it will be appreciated that the vanes are provided along the entire assembly, as indicated by the arrows. If the apertures are angled at other angles, the vanes 210 may also be angled so as to remain perpendicular thereto. Alternatively, the collimator vanes 210 and apertures 208 may be at angles to one another other than perpendicular.

X. Resolution and Efficiency

The in-plane resolution of a system according to the present invention is determined by the radii of the detector and aperture arcs, $R_D$ and $R_A$, the distance, Dist, of the object from the aperture arc, and the widths of the slots and the detector elements, $W_{slot}$ and $W_{det}$ respectively:

$$\text{resolution} \approx W_{slot} + \frac{Dist \times (W_{slot} + W_{det})}{(R_D - R_A)}$$

Figure 15:
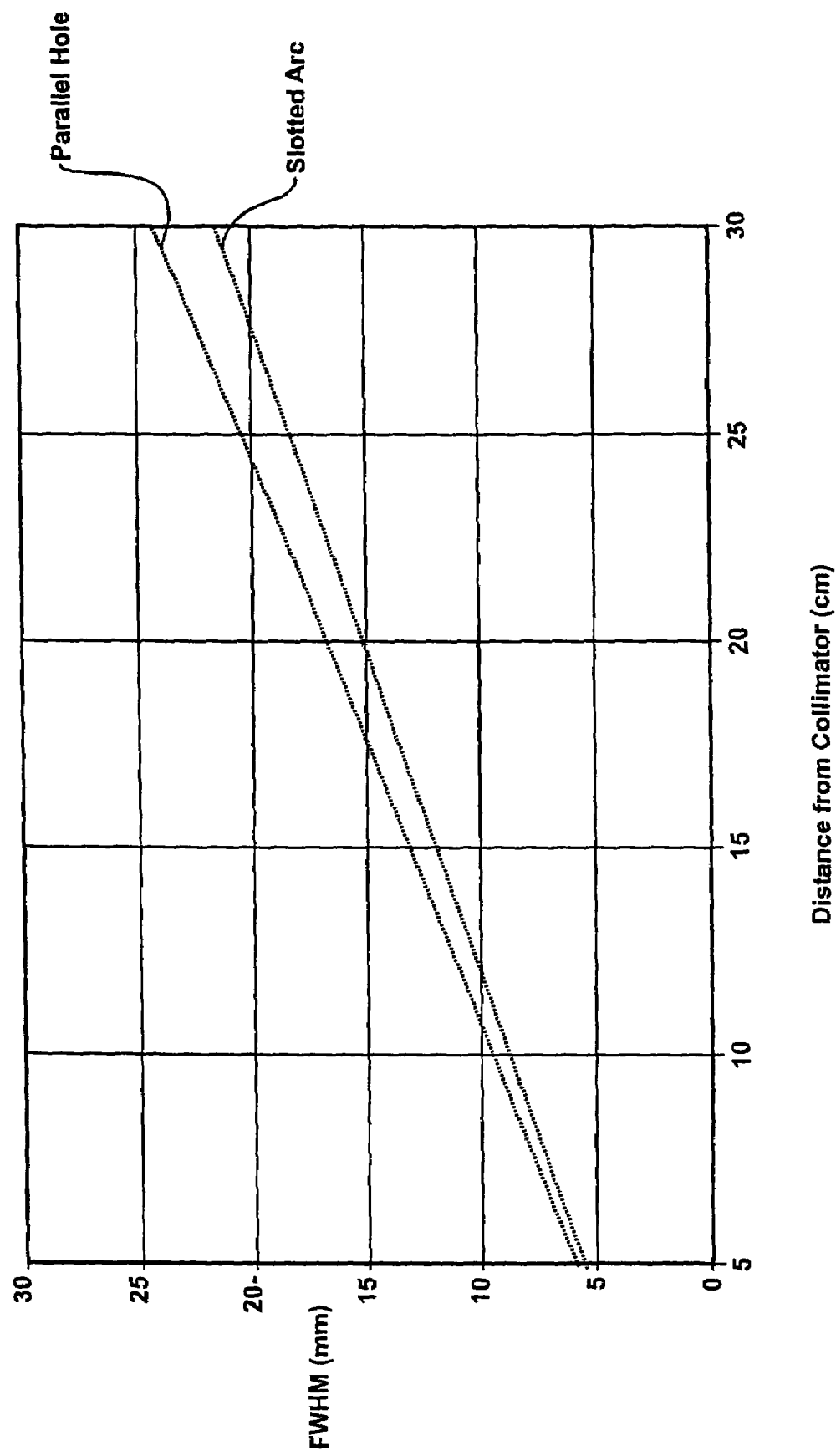
FIG. 15 is a plot showing the in-plane spatial resolution at different depths using the present invention versus a traditional "high resolution" parallel-hole collimator.

FIG. 15 plots the resolution at different depths (distance from the collimator to the point of interest in the patient) of the present invention versus a traditional parallel-hole collimator. The slotted arc system is assumed to have a slot width of 2.4 mm, a detector width of 4 mm and other parameters as discussed with respect to FIG. 4. The parallel-hole collimator for which data is plotted has a hole diameter of 2.2 mm and a collimator thickness of 3 cm.

The detection efficiency of the slotted aperture system is proportional to the detector solid angle, $\Omega$, for a point source at the center of the field-of-view and may be calculated based on Rogers (IEEE TIMI, vol. MI-1, pp. 63–68, 1982) as:

$$\Omega = n_{slots} \frac{1}{R_D^2} \left[ \sqrt{r_{obj}^2 - r_D^2} \cdot \frac{1}{R_A} \sqrt{[r_{obj}(R_D - R_A)]^2 - [R_A r_D]^2} \right] f p_{det}$$

where $r_{obj}$ and $r_D$ are the full-width-half-maximum object and detector resolution respectively, $p_{det}$ is the detector packing fraction and f is the fraction of frontal area closed by the longitudinal collimating vanes. In the configuration of this invention, f=vane thickness/vane separation.

As the aperture arc moves to differing positions relative to the detectors, the apparent width of the aperture slots will vary as a function of the sine of the angle between the slot and the detector. Since the apparent width of the detector as viewed from the slot also changes according to a similar function, the overall detection efficiency will vary as a function of the square of the sine of the detector-slot angle. The exact function will depend on the photon cross-section of the detector element (a function of detector thickness) and on the photon cross-section of the slot aperture. This variation of detector sensitivity with slot position is easily mapped for a given detector and may be corrected for in software in a manner similar to the detector uniformity corrections routinely performed in traditional gamma cameras.

It is to be noted that imaging systems constructed according to the methods of this disclosure are relatively insensitive to the structured image artifacts seen in rotating gamma camera SPECT systems when non-uniformities of detector sensitivity exist. In the systems described here, the reduced count sensitivity caused by a particular, relatively insensitive, detector element is spread across the entire image plane, rather than appearing as the structured "ring" or "arc" artifacts seen in traditional systems. Such artifacts frequently trouble present artifact systems.

XI. Collimator Construction

As will be appreciated by those of skill in the art, the construction of lead collimators presents significant challenges. Lead has a very high density, but is not particularly stiff or strong. Therefore, vanes of lead are heavy and vulnerable to damage. In traditional parallel hole collimators, the vanes are made very thin and define a plurality of small parallel holes. The depth of the holes in the collimators is somewhat limited by the strength and stiffness of the lead material. That is, if a collimator is to be constructed that has more than a particular depth, the thin lead vanes may actually sag over time, destroying the usefulness of the collimator. Similar considerations apply to the present invention. The collimating vanes, such as 220 in FIG. 13 and 210 in FIG. 12 are large and heavy, thereby presenting challenges to how to adequately support the individual vanes. Additionally, it is important that the individual vanes be accurately positioned and aligned.

Figure 16:
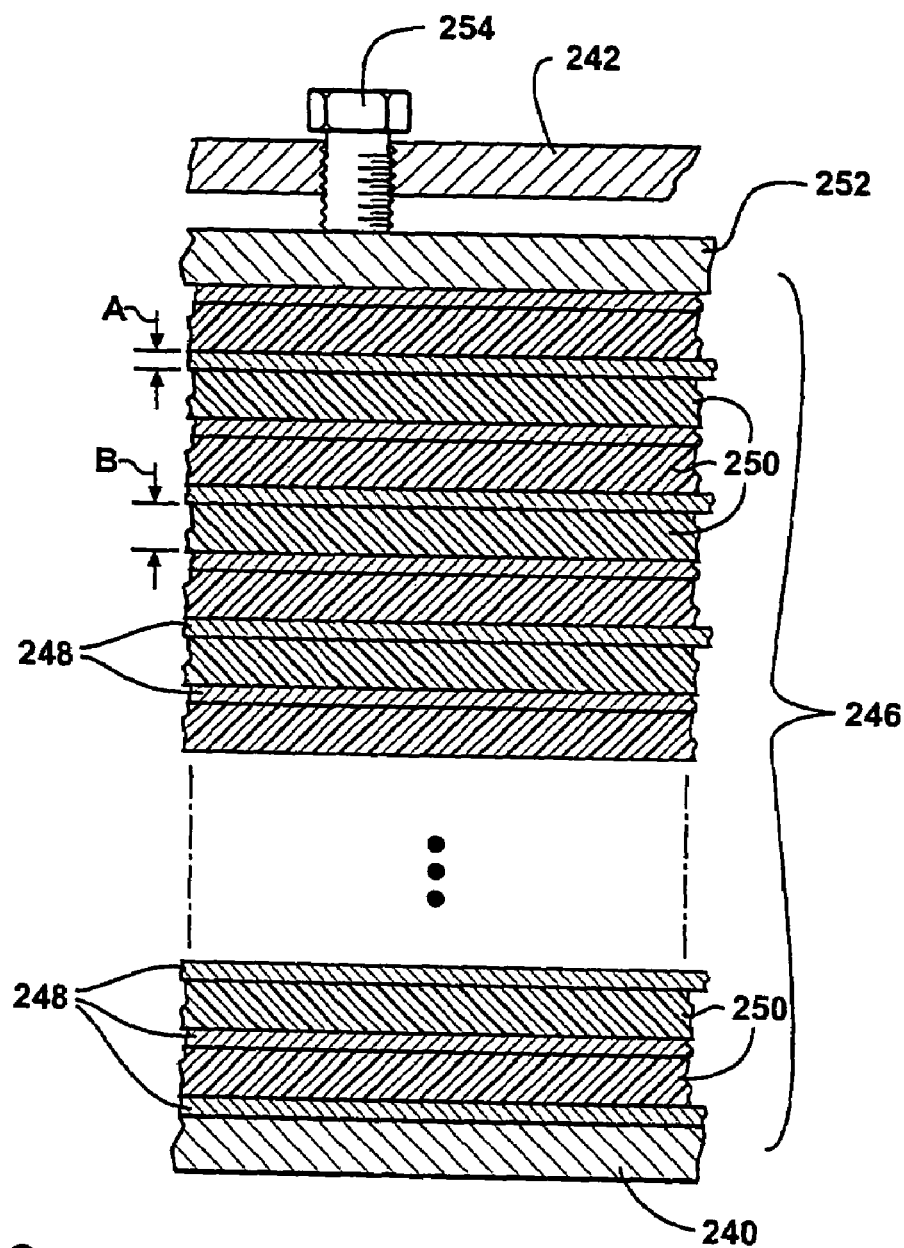
FIG. 16 is a cross-sectional view of a portion of a parallel vane collimator according to the present invention.

A further inventive aspect of the present invention is a design providing a collimator with parallel lead vanes that are supported by being formed in a stack with sheets of radiolucent material disposed between each lead vane. FIG. 16 illustrates a portion of a parallel vane collimator constructed according to this aspect of the present invention. FIG. 16 also illustrates a portion of a support assembly, including a lower support member 240 and an upper support member 242.

Figure 17:
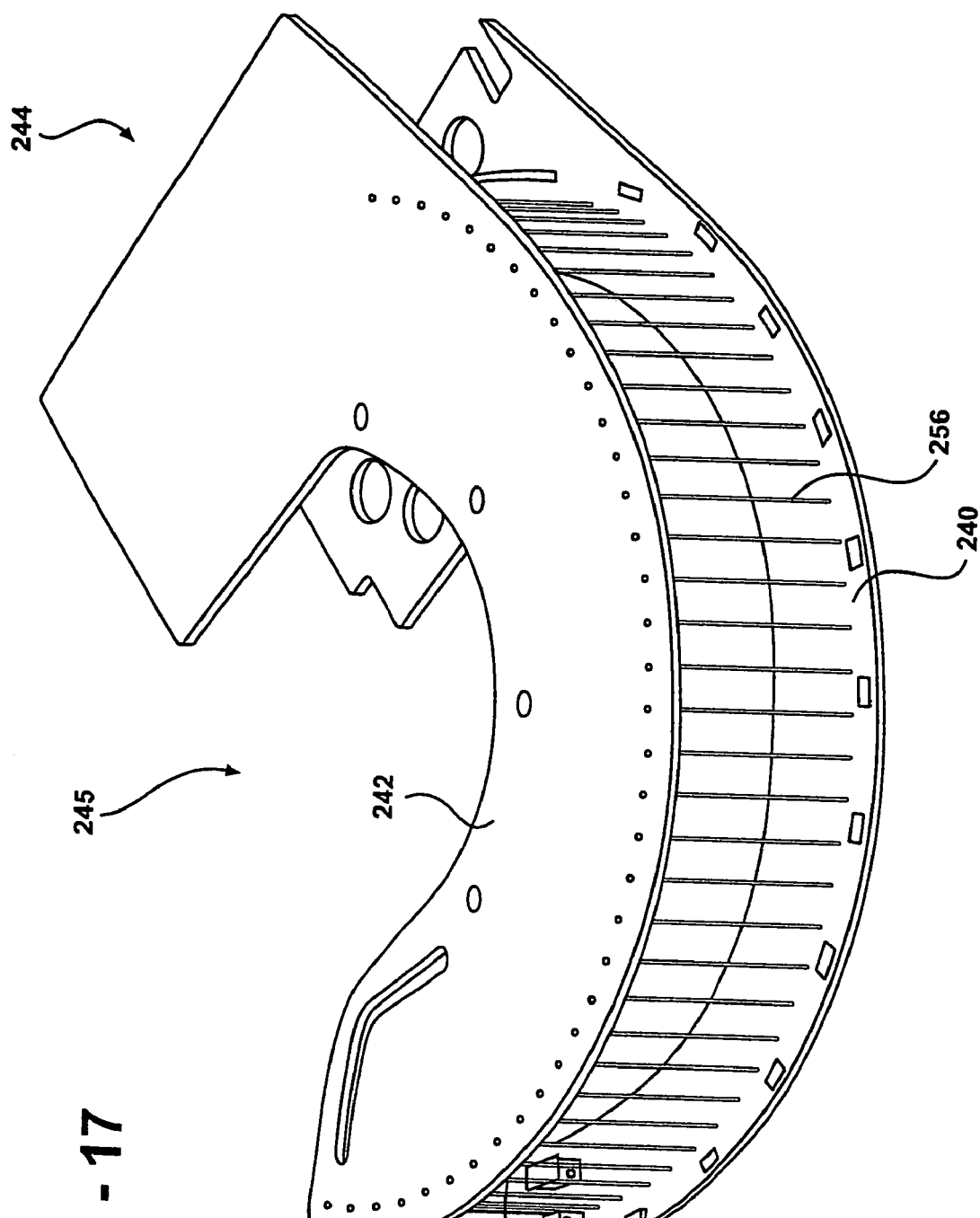
FIG. 17 is a perspective view of the support assembly for one embodiment of an imaging arc according to the present invention.

FIG. 17 shows the lower support member 240 and upper support member 242 in their entirety, according to one embodiment of the present invention. However, FIG. 17 does not illustrate the collimation assembly inside of the support assembly. Referring to FIG. 17, the lower support member 240 and upper support member 242 form part of a support assembly 244. This support assembly 244 forms part of the imaging arc 106, as shown in FIGS. 1A and 1B. It wraps about the patient field of view, illustrated at 245 in FIG. 17. When assembled, the imaging arc includes the support assembly 244, the parallel vane collimating assembly supported therein, single or multiple detectors, and the aperture arc. It is also preferably clad in a housing so as to protect the internal workings, and provide an aesthetically pleasing exterior appearance. One end of the support assembly 244 is interconnected with the chair base 108 for supporting the imaging arc. This may be accomplished in a variety of ways. Alternatively, an additional support may be provided mid-arc.

Referring again to FIG. 16, a portion of the parallel vane collimating assembly is shown at 246. The collimating assembly includes sheets or panels of lead 248 with sheets or panels of radiolucent material 250 separating the lead sheets 248. The collimator assembly may be formed by stacking a lead sheet, and then a radiolucent sheet, and then repeating the process until a sufficiently tall stack is formed, as shown. The radiolucent material maintains the relative positioning of the lead sheets, and prevents any sagging or movement of the lead sheets. Preferably, a compression panel or upper support plate 252 is provided on top of the stack of lead sheets and radiolucent material, and below the upper support member 242. Biasing devices, such as threaded member 254 are then provided to press downwardly on the compression panel 252. This compresses and stabilizes the stack 246. Preferably, a thicker lead sheet, or other photon blocking material 253 is provided at the top and bottom of the stack, to block photons from entering the top or bottom of the collimator assembly.

As will be clear to those of skill in the art, a modified version of this assembly procedure may be used to construct a collimator assembly such as shown in FIG. 12. According to a further aspect of the present invention, a related approach may be used to form parallel hole collimators. That is, a parallel hole collimator may be formed using radiolucent material filling the holes in the parallel hole collimator, to thereby support the collimator vanes. Parallel hole collimators are often damaged in use, because of the fragility of the lead septae between the holes. According to the present invention, the holes of the collimator may be filled with a radiolucent material as it is constructed. This turns the parallel hole collimator into substantially a solid block, which is more resistant to damage. Also, this allows deeper and/or thinner vanes to be formed and supported than would otherwise be practical.

Figure 18:
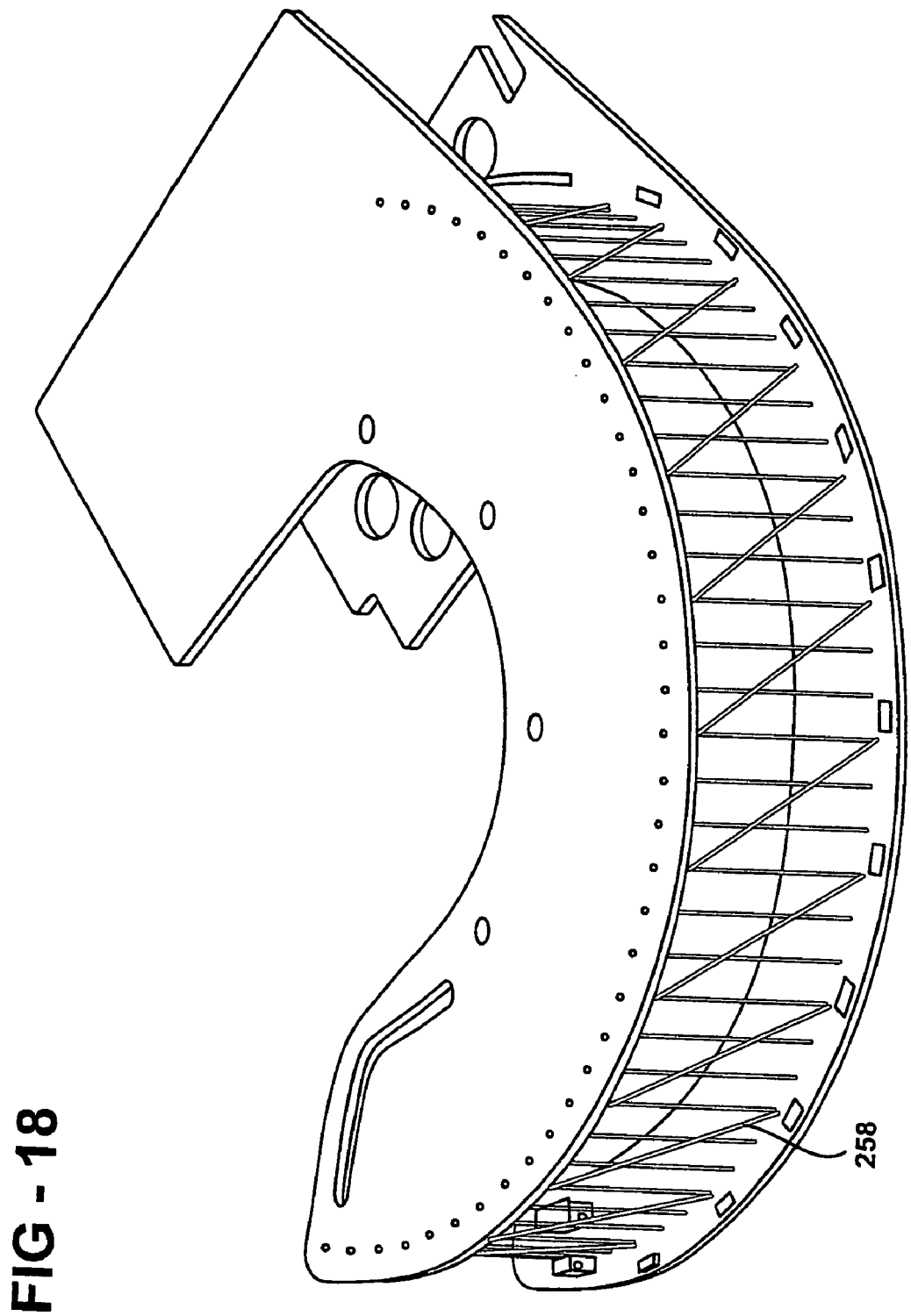
FIG. 18 is a perspective view of a support assembly similar to FIG. 17, with additional tension members.

Referring again to FIG. 17, an alternative approach to forming a parallel vane collimator assembly according to the present invention may be provided by allowing the upper and lower support members 240 and 242 to be tensioned against each other, such as by tensioning members 256. That is, the alternating stack of lead panels and radiolucent panels may be placed on the lower support member 240, covered by upper support member 242, and compressed using compression or tension members 256. Those of skill in the art will appreciate that the parallel vane collimator according to the present invention is very heavy, and therefore the cantilevered arc support assembly bears a substantial load. FIG. 18 illustrates that the support assembly may include a plurality of angled tension members 258, either angled to the left as shown, or angled to the right, or both. The tension members act like bicycle spokes in providing structure and support. They also allow a substantially open back to the arc for access to the electronics and for cooling.

Figure 19:
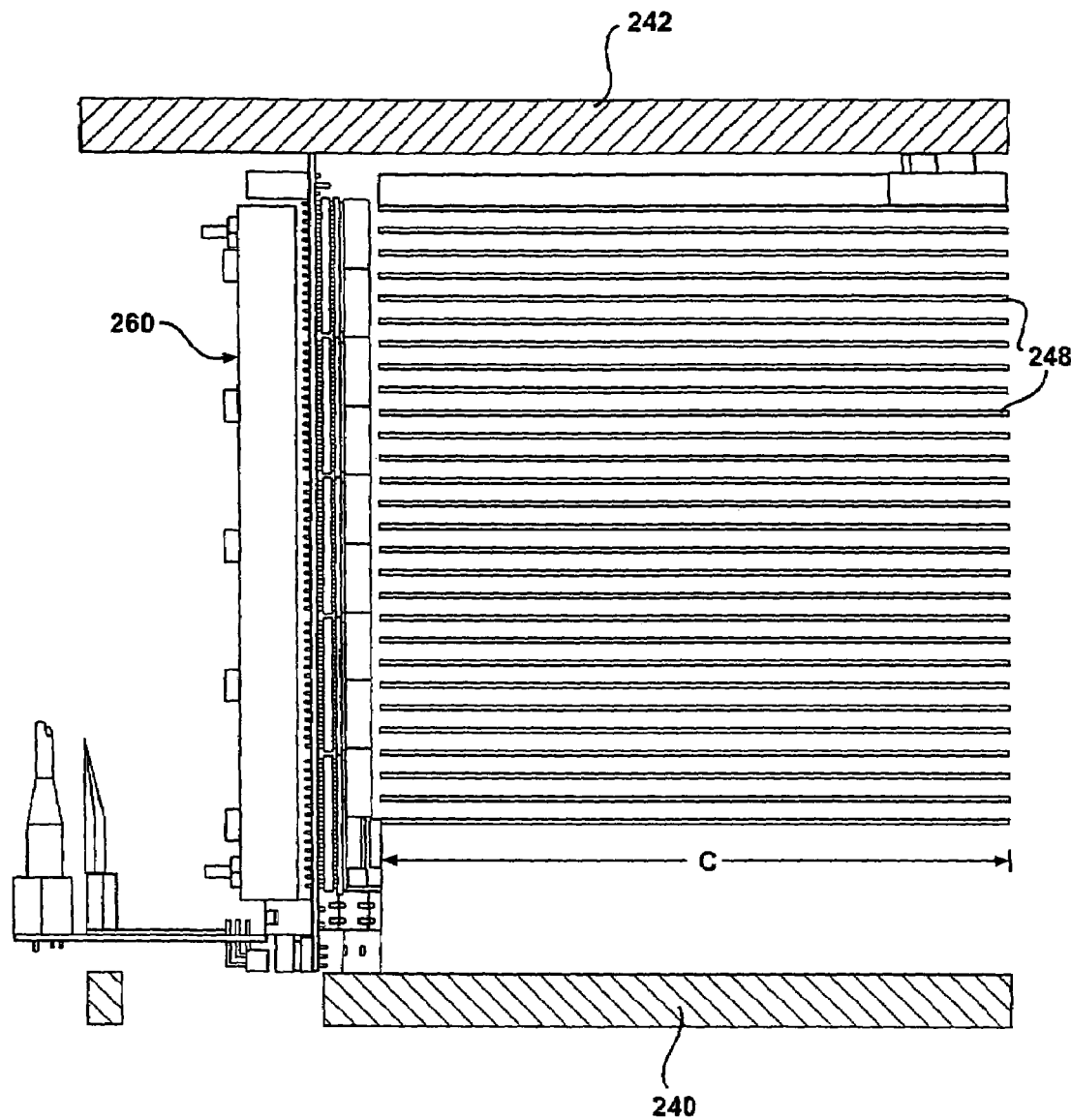
FIG. 19 is a cross-sectional view of a portion of a parallel vane collimator and a sensor assembly according to the present invention, showing the relative depth of the collimator vanes.

FIG. 19 provides a cross-sectional view of a portion of the imaging section of the present invention. It illustrates the lower support member 240, the upper support member 242 and the lead sheets 248 positioned therebetween. The radiolucent material is not illustrated in this view. However, an electronics package or detector array for detecting incoming photons is illustrated generally at 260. This detector array will be discussed in more detail hereinbelow.

The design of the present invention provides advantages heretofore unavailable with respect to collimator design. Traditionally, collimator designers have limited the depth to width ratio of the collimator holes. That is, the holes defined by the collimator may be considered to have a front-to-back depth and a side-to-side or top-to-bottom width. (In a parallel hole collimator, a side-to-side and top-to-bottom widths are typically the same. In the present invention, the "side-to-side width" is a function of the size of the aperture in the aperture arc, while the top-to-bottom width is a function of the spacing between the parallel vanes.) In the prior art, a depth-to-width ratio of less than 10:1 has been considered optimal. In fact, the literature has stated that a 10:1 ratio is almost equivalent to an infinitely large ratio. In other words, excepted theory has taught against depth to width ratios over 10:1. Additionally, prior art designs for collimators have made it extraordinarily difficult to create a depth-to-width ratio that is very large. Deep collimators suffer from structural integrity issues. To get a high depth to width ratio in prior art designs requires vanes that are too thin and tall to be self supporting. So, practicality also taught away from high depth to width ratios.

The present invention departs dramatically from the prior art approach. In one embodiment of the present invention, the lead sheets have a thickness of approximately 2 mm, as indicated at A in FIG. 16. The radiolucent sheets have a thickness of approximately 4.5 mm. Therefore, the "gap" between adjacent lead sheets is approximately 4.5 mm. In this same embodiment, the front-to-back depth of the lead vanes 248, as shown at C in FIG. 19, is approximately 150 mm. In this embodiment, the depth-to-width ratio is greater than 33:1. In a more preferred embodiment of the present invention, the lead vanes have a thickness of approximately 1.25 mm. However, the gap remains the same at approximately 4.5 mm. Therefore, the depth-to-width ratio remains the same. According to the present invention, depth-to-width ratios greater than the prior art maximum of 10:1 are preferred. Depth-to-width ratios greater than 20:1 are more preferred. Depth-to-width ratios over 30:1 are even more preferred.

According to the present invention, it is also preferred that the thickness of the lead vanes be greater than 0.5 mm. A thickness of greater than 0.75 mm is more preferred, a thickness of 1 mm or more is even more preferred, and a thickness of at least 1.25 mm is most preferred. These thicknesses also depart dramatically from the prior art. Prior art high resolution parallel hole collimators typically have lead vanes with a thickness of 0.2 mm or less, and significant effort has been expended to obtain thinner and thinner lead vanes.

The use of substantially greater depth-to-width ratios than used in the prior art, as well as the use of substantially thicker lead vanes, provides significant advantages that have not been recognized or appreciated in the prior art.

In SPECT imaging, it is important to accurately determine the direction from which a photon is traveling, the energy level of the photon, and the number of photons coming from that direction. These photons have sufficient energy to penetrate lead if it is not sufficiently thick. In prior art parallel hole collimators, the thin lead vanes are typically too thin to stop many of the photons from passing therethrough. Therefore, a photon that strikes a particular area cannot be assumed to have traveled straight down the hole adjacent that area. Instead, the photon may have originated in a different hole and penetrated the lead vane in-between the adjacent hole and the hole in which it is sensed. Consequently, accuracy is sacrificed. This contributes to blur in the resulting image. The depth-to-width ratio of the holes in the collimator also has an effect on the resolution of the imaging device. If a collimator hole is short and wide, a photon may enter that hole at an angle significantly off from the axis of the hole. If the hole is deeper and narrower, the range of angles of incoming photons that travel just down that hole is much narrower.

In the present invention, the use of substantially thicker vanes and the use of a collimator with a very high depth-to-width ratio, both lead to substantially increased accuracy or resolution. Because the vanes are thick and the depth is very high, any photon that reaches the sensor at the back of the collimator can be assumed to have passed through the aperture in the aperture arc and between the adjacent lead vanes. In other words, each photon "count" is a good count.

The prior art also tends towards the use of much smaller gaps than in the present invention. Experimentation with the present invention have shown that larger gaps, on the order of 4 or 4.5 mm, along with thicker lead vanes leads to higher efficiency and resolution. As a further aspect of the present invention, the use of gaps greater than 2 mm is preferred, with gaps greater than 3 mm being more preferred, and gaps of 4 or more mm being most preferred.

Referring again to FIG. 19, the sensor array 260 is positioned adjacent the back of the collimating assembly. In some embodiments, the individual sensors are positioned immediately adjacent the rearmost end of the vanes, while in other embodiments the sensors are spaced from the back of the vanes by a short distance. Increasing the gap between the back of the vanes 248 and the sensors reduces some of the effective dark area caused by the photons that are blocked by the vanes. In one preferred embodiment, the sensors are spaced from the back of the vanes by 2 to 3 mm.

XII. Extension Flaps

As shown in FIGS. 1 and 4, for an embodiment optimized for cardiac imaging, the use of an arc shaped imaging apparatus allows the patient to easily enter and leave the imaging system. As the aperture arc rotates however, it will extend slightly into the open area of the arc. The invention therefore optionally provides for pivoted Extension Flaps to be located at one or both ends of the aperture arc, as shown in FIGS. 20A and 20B. This figure shows one end of the aperture arc 300 that includes an extension vane 302 extending its length. FIG. 20A shows the aperture arc 300 and vane 302 at one extreme of the arc's movement and FIG. 20B shows them at the other extreme. Extension vane 302 is movably attached to the aperture arc by hinge 304. Pivot rod 306 is located in the path of the vane such that, as the extension vane is pushed against it by the movement of the aperture arc, the extension vane is caused to pivot away from the patient as shown in FIG. 20B. This minimizes the extension of the arc or vane into the opening while maintaining shielding of the detectors from unwanted external radiation.

Figure 21:
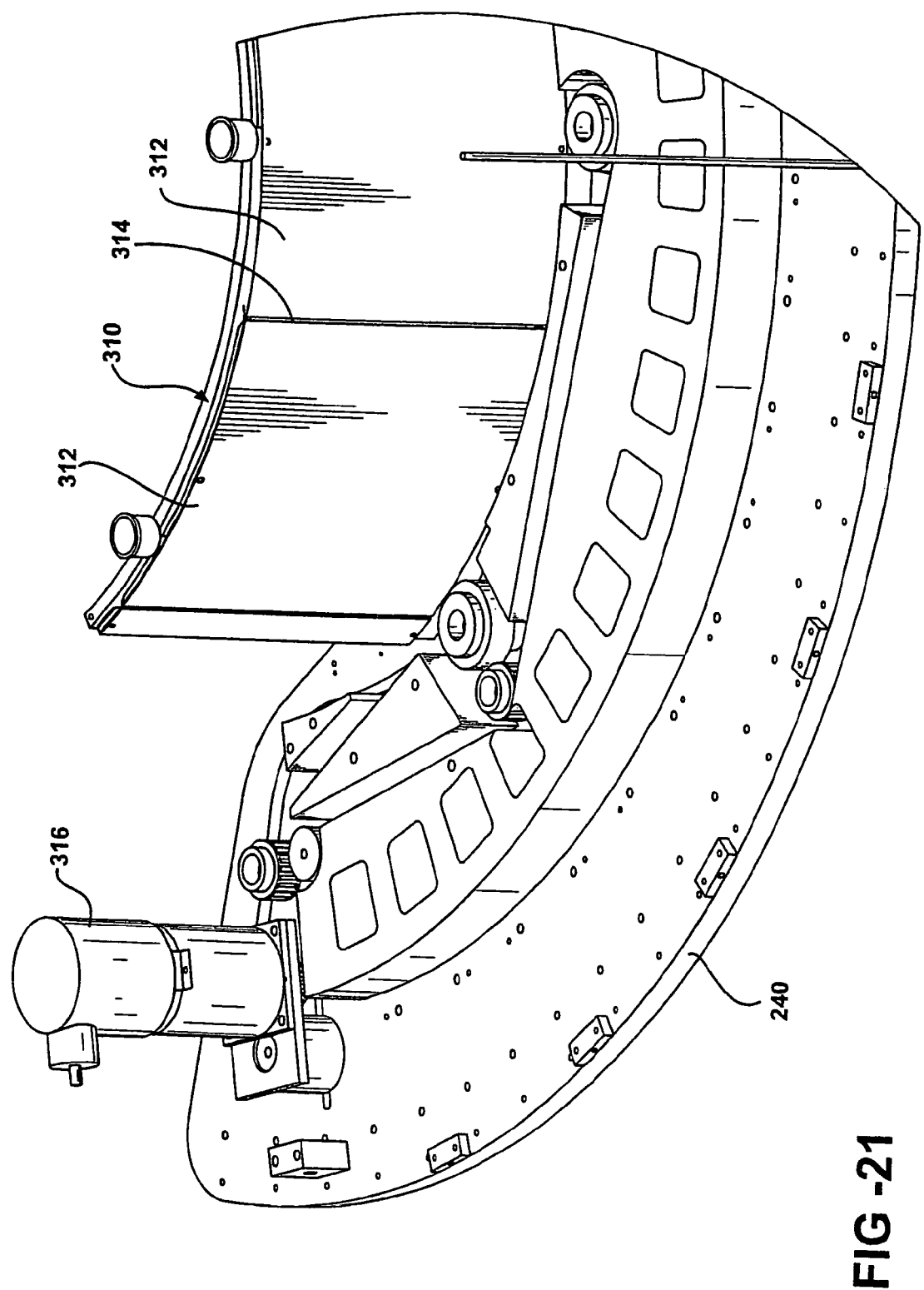
FIG. 21 is a perspective view of a portion of a lower support member and a portion of an aperture arc according to one embodiment of the present invention.

Referring now to FIG. 21, one preferred construction of the aperture arc is illustrated. The aperture arc is shown at 310, being supported on the support member 240, which forms the bottom part of the support structure of the imaging arc. In this embodiment, the aperture arc 310 is formed from individual arcuate panels 312 that are positioned adjacent one another so as to provide an aperture 314 therebetween. The width of the aperture 314 may be determined by the relative positioning of the panels 312. The aperture arc 310 is supported in a track in the support member 240 and moved by a drive motor 316, which drives a series of belts and pulleys.

XIII. Detector Variations

Turning now to detector or sensor designs, a variety of approaches may be used with the present invention. FIGS. 2 and 3 illustrate strip detectors that may be considered one-dimensional linear arrays. Two-dimensional arrays are also provided in this invention. Such arrays may be provided as integral units or may be approximated by placing two or more one-dimensional arrays in close proximity. The overall sensitivity of the imaging system is linearly proportional to the detector surface area available.

Figure 22:
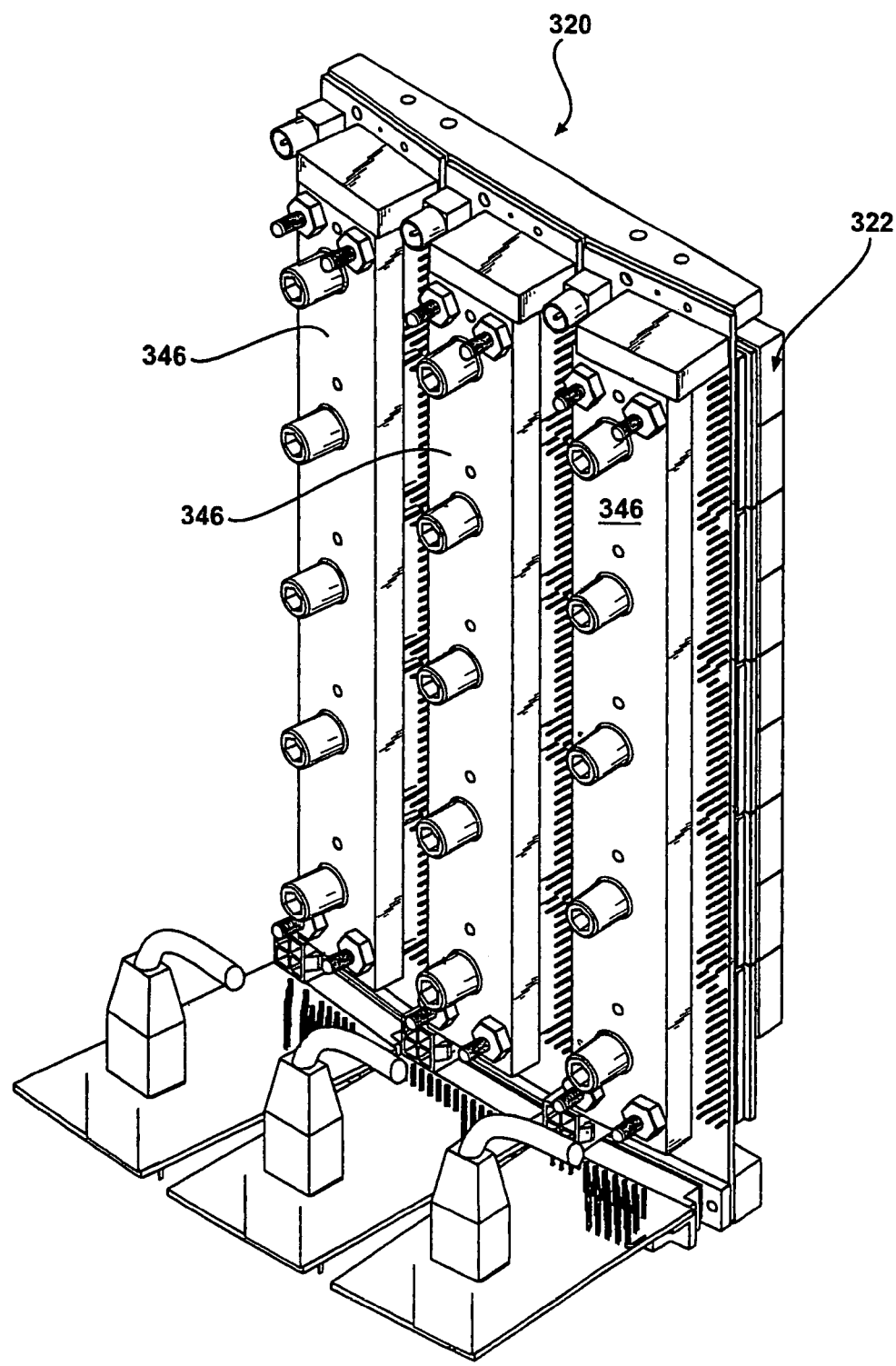
FIG. 22 is a rear perspective view of a sensor assembly for use with the present invention.
Figure 23:
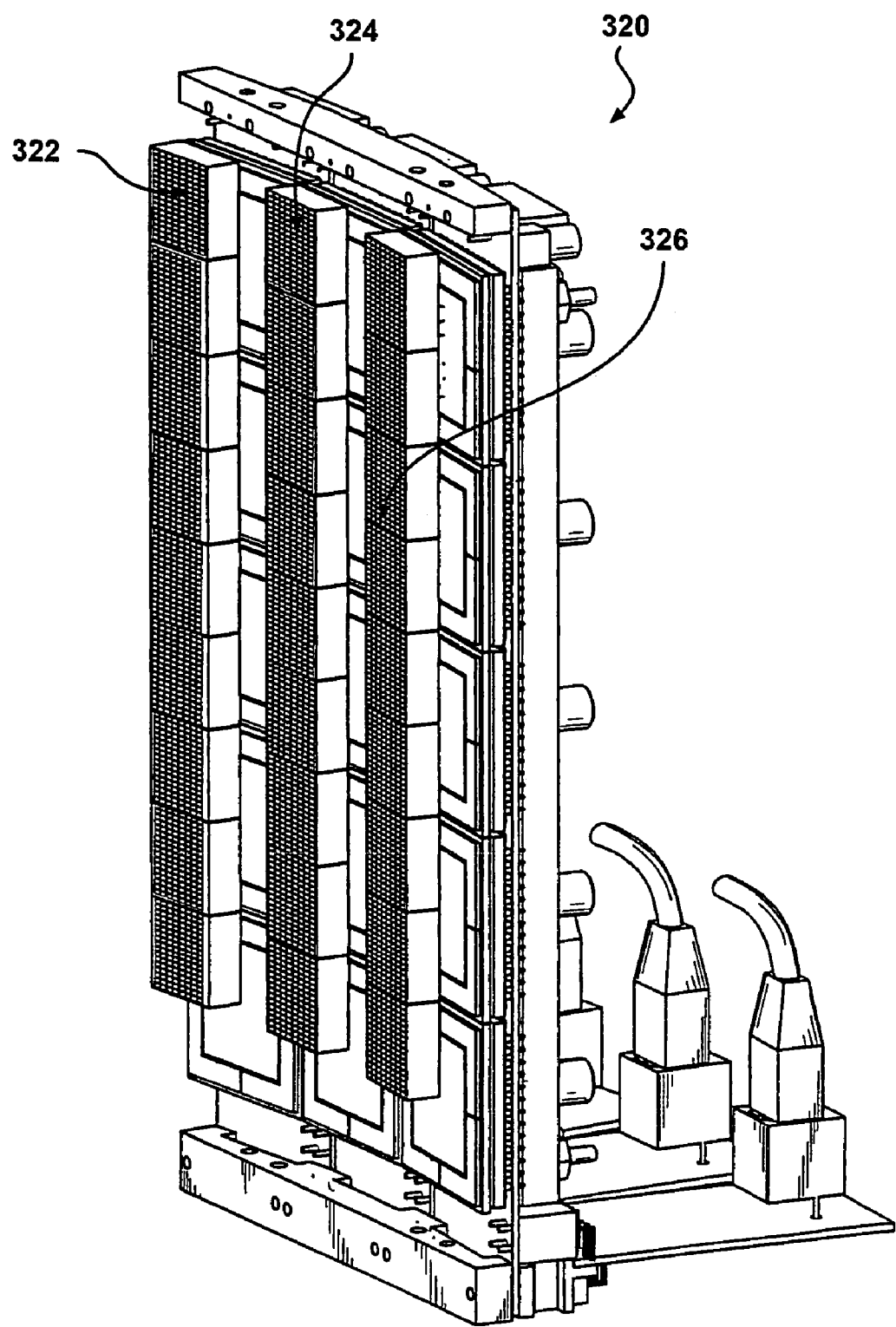
FIG. 23 is a front perspective view of the sensor assembly of FIG. 22.
Figure 24:
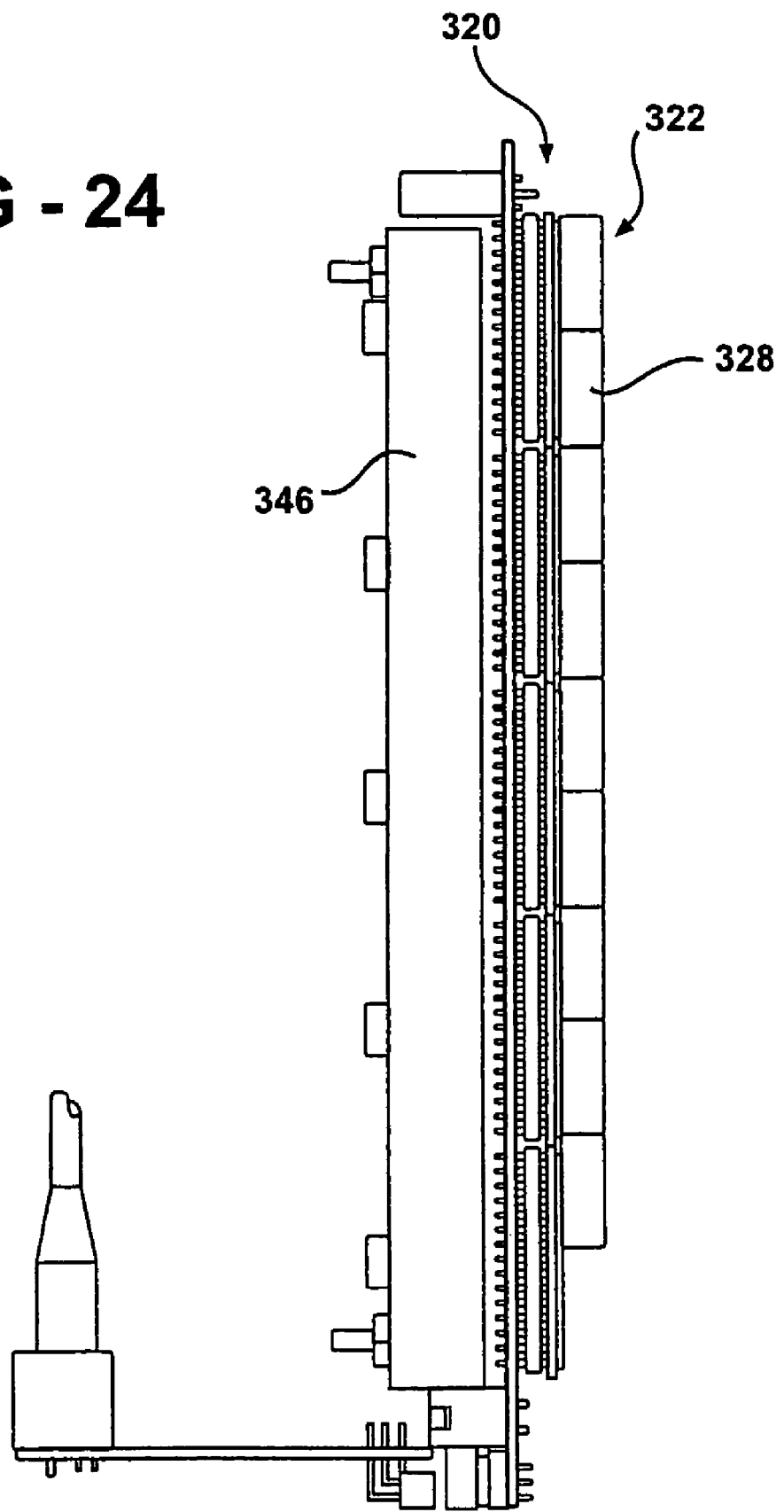
FIG. 24 is a side-elevational view of the sensor assembly of FIGS. 22–24.

Referring to FIGS. 22–24, three views of a preferred embodiment of a sensor assembly for use with the present invention is generally shown at 320. As best shown in FIG. 23, the assembly 320 includes three two-dimensional sensor arrays 322, 324, and 326. Each sensor array, in turn, is formed of a series of sensor modules, such as 328 in FIG. 24. The sensor modules are solid state CZT (Cadmium Zinc Telluride), or alternatively, Cadmium Telluride may also be used. FIG. 25 illustrates a cross-sectional view of one of the sensor modules 328. The module has a central body of CZT 330 with multiple small, thin, square electrodes 332 on the front face. A larger electrode is provided on the back surface, and a chip for processing data signals from the sensor is provided on the back at 336. Photons strike the front surface of the sensor module 328 and are sensed by the module. FIG. 26 illustrates an alternative embodiment wherein a chip 338 is only half covered by sensing materials 340. FIG. 26 also illustrates the configuration of the electrodes 342 on the face of the module.

FIGS. 22 and 24 illustrate cooling manifolds 346 for the sensing assemblies.

As known to those of skill in the art, solid state photon sensors are difficult to produce without internal flaws. Referring to FIG. 25, the body of CZT material 330 is a crystal that may develop flaws during creation or manufacturing. If the body 330 does not have flaws, a photon passing through the front face and into the CZT body 330 enables the presence of this photon to be sensed by the electrodes 332 and 334. As shown in FIG. 26, the electrodes 342 define a two-dimensional grid. Consequently, the location of the photon strike may be determined by determining which electrode senses the presence of the photon. If the CZT is flawed, it may have dead spots, where a photon strike is not sensed. Typically, electrodes on the front of the CZT body are sized and spaced so that one electrode is responsible for sensing one "pixel" of information. Typically, a pixel size is chosen and equal to the desired resolution of the sensing system. In cardiac sensing, it is preferred to have resolution of approximately 4 to 4.5 mm. Therefore, the electrodes would typically be arranged on 4–5 mm centers such that one electrode is responsible for each "pixel." If the CZT has a flaw, the flaw may cause a dead pixel, which can seriously affect image quality.

Figure 27:
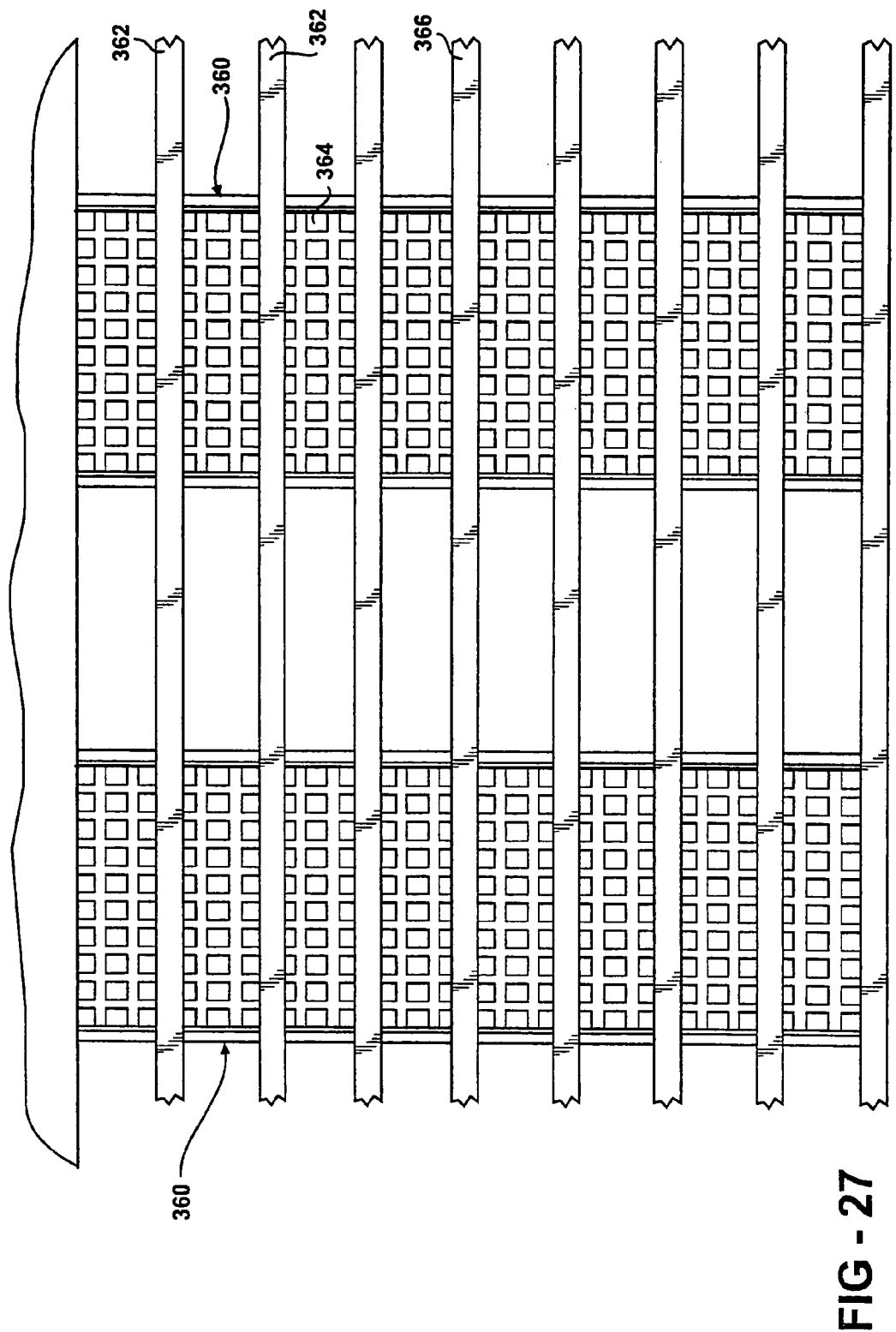
FIG. 27 is a view of a pair of sensor arrays as viewed through the collimator assembly.

According to a further aspect of the present invention, the desired resolution, in this case, 4 to 4.5 mm, is subdivided into smaller segments and smaller electrodes are used. In FIG. 26, box 350 represents an area that is approximately 4 to 5 mm wide and tall. However, rather than having a single electrode in this area, this "macro pixel" is subdivided into four pixels, each with its own electrode 352. If the CZT underlying the macro pixel 350 has a flaw, the flaw will typically lead to only a single bad pixel associated with one of the electrodes 352. For example, one of the four electrodes may be associated with a portion of the CZT that has no sensitivity, reduced sensitivity, or, in rare cases, increased sensitivity. The sensor module can then be calibrated, and the data from the four electrodes 352 processed so as to provide meaningful data from the macro pixel 350. For example, if one electrode is associated with a pixel that is dead, the output from the remaining three pixels may be combined, and multiplied by ¾ to obtain an output for the macro pixel 350. In this way, a sensor module with a CZT body with some flaws is still useable. In the module of FIG. 26, the electrodes 352 preferably have a side-to-side and top-to-bottom dimension of approximately 2.46 mm, and spacing between adjacent electrodes of approximately 0.04 mm. In another preferred embodiment, especially optimized for cardiac use, the electrode-to-electrode pitch is approximately 2.25 mm. Referring again to FIG. 19, the sensor assembly 260 is shown adjacent the rear of the lead vanes 248. FIG. 27 illustrates a view of the sensor arrays 360 as viewed through the vanes 362. In some embodiments, the pitch between the vanes 362 is not evenly divisible by the pitch between the electrodes 364. For example, in one embodiment, the pitch between the vanes 362 is approximately 6.5 mm, while the pitch between the electrodes 364 is approximately 2.5 mm. In order to avoid moiré patterns due to the alignment between the vanes and the pixels, it is desirable that the number of pixels in each gap between the vanes is approximately the same. Because the vane pitch is not a multiple of the pixel or electrode pitch in this embodiment, the sensor arrays 360 are arranged such that they are centered on the middle vane 366. As shown in FIG. 27, this arrangement prevents an electrode, and hence a pixel, from lying directly behind one of the vanes 362.

This invention also provides for radiation detectors constructed from scintillation materials such as sodium iodide or cesium iodide with associated photomultiplier tubes or other photo-detectors such as solid state photodiodes. FIG. 28 shows one embodiment of a scintillation-based detector module 400. This embodiment includes a cylindrical crystal 402 of scintillation material clad in a radiolucent, light-reflective covering 404 such as aluminum. The covering 404 is open at both ends of the cylinder. Affixed to each end, via optical coupling material, is a light detector such as a photomultiplier tube, photodiode, or other photo-detector (not shown). The position of scintillation events occurring within the scintillation material is determined by the ratio of outputs of the two photo-detectors, thus providing longitudinal position sensing within the detector. This embodiment is extremely inexpensive to produce, but has the disadvantage of a variable photon detection efficiency across its horizontal dimension caused by the varying scintillator thickness over its circular cross-section. This causes a deviation of the detector's response function from a pure rect function, thus slightly degrading spatial resolution.

Figure 29C:
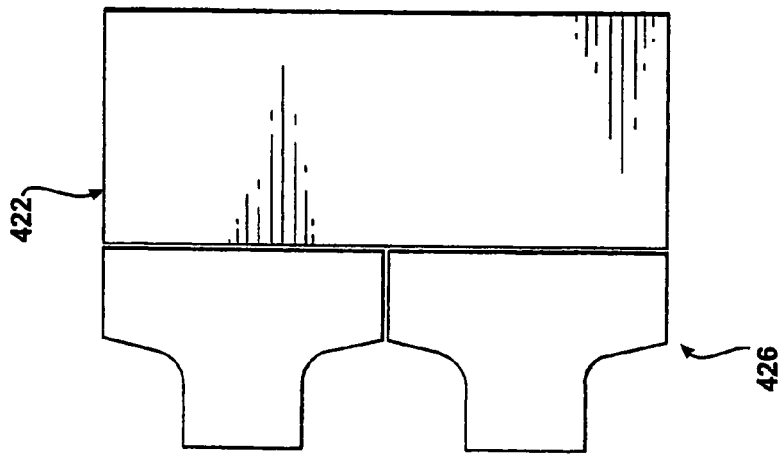
FIG. 29C is a view similar to FIG. 29B but with the photo detectors positioned at the rear face of the scintillation material.
Figure 29B:
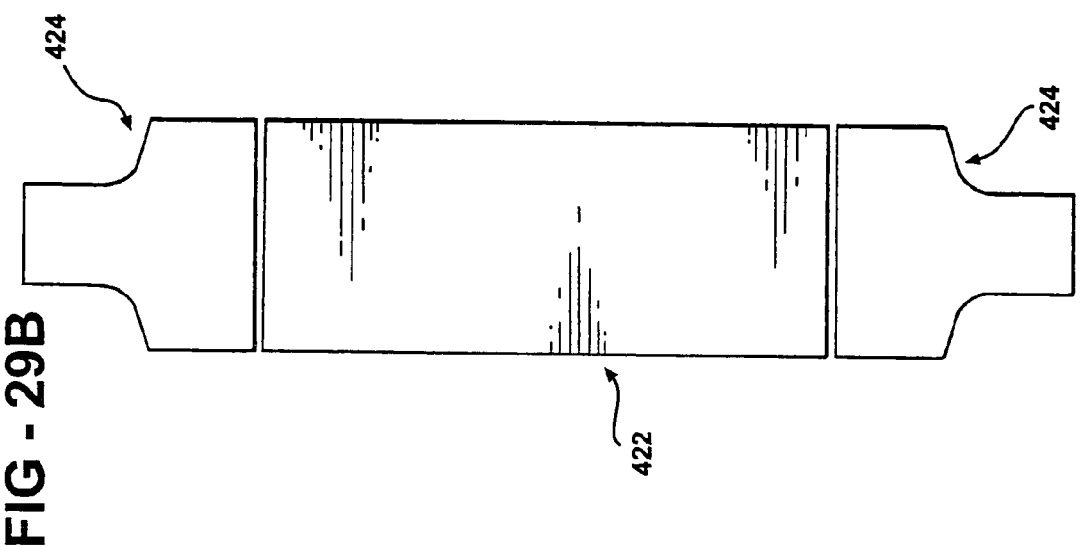
FIG. 29B is a side elevational view of the module of FIG. 29A with photo detectors at the top and bottom.
Figure 29A:
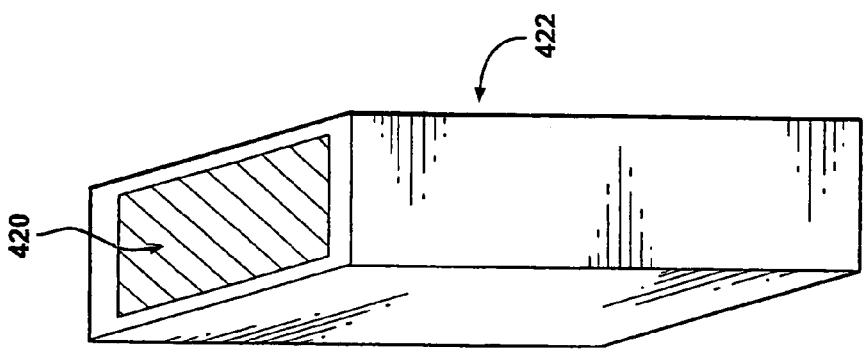
FIG. 29A is a perspective view of another embodiment of a detector module using a rectangular bar-shaped piece of scintillation material.

FIGS. 29A–C show more efficient embodiments of a scintillator-based detector, consisting of a rectangular bar 420 of scintillator material clad in a radiolucent, light-reflective material 422 such as aluminum. In FIG. 29B, the cladding is open at the top and bottom so as to permit placement of photo detectors 424. In the alternative embodiment shown in FIG. 29C, the cladding is open at the rear of the module so that two or more photo-detectors 426 can be affixed. In either case, the photo-detectors are considered to be adjacent the ends of the scintillation material so that they can locate the position of a scintillation event.

FIG. 30 shows a piece of scintillator material 430 with a trapezoidal cross section clad in reflecting material 432, similar to the previous Figures. As with the embodiments of FIGS. 29A–C, the photo-detectors may be affixed on either the top and bottom of the module or at the rear face. The embodiment with the trapezoidal cross section has the advantage of presenting a more uniform cross-section to incoming radiation, but is more costly to manufacture. That is, radiation coming at an angle to the front face still encounters the full depth of the scintillator material.

Axial resolution of the tomography system is directly dependent on detector width, as described above. Specifically, narrower detectors increase the axial resolution of the system. As detector width narrows, however, photon detection efficiency drops because photons striking the front face of the narrow detector may scatter out of the detector material before they have deposited all of their energy. According to the present invention, the efficiency of a high resolution elongated strip of scintillation material may be improved by masking a portion of its front face. FIG. 31A shows a detector configuration 440 based on a rectangular piece of scintillation material. FIG. 31B shows a detector configuration 442 based on a cylindrical piece of scintillation material. FIG. 31C shows a detector configuration 44 based on a piece of scintillation material with a trapezoidal cross section. In each of these embodiments, in addition to the reflective cladding 446, the scintillator is clad in an additional masking layer 448 of lead, tungsten or similar high-attenuation material. This outer masking or shielding layer is configured to have a narrow vertical opening 450 of the dimensions desired for the detector cross-section. Once photons have passed through the opening and struck the scintillator, further scattering is more likely to occur within the larger volume of scintillator located behind the opening 450 in the mask 448 rather than scattering outside the scintillator material. If desired, an additional layer of low-Z material (not shown) may be interposed between the cladding and the shielding layers so as to absorb secondary lead x-rays emitted by the mask 448. As will be clear to those of skill in the art, the detectors shown in FIGS. 31D have the improved efficiency of wider detectors with the higher resolution of narrower detectors. Similar masking can be applied to solid-state detectors, such as shown in FIG. 2, resulting in similar advantages.

Figure 34:
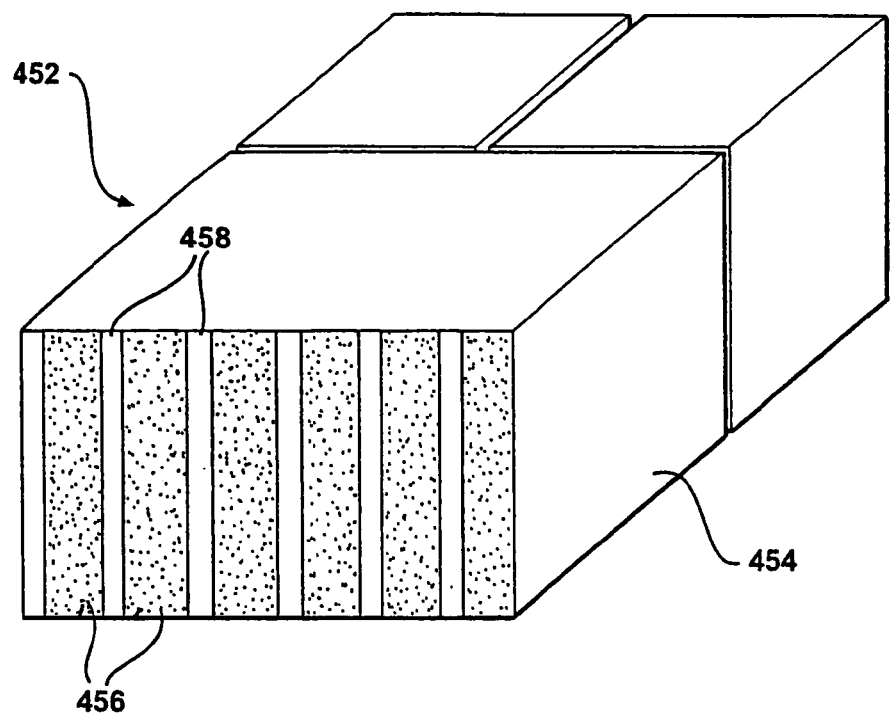
FIG. 34 is a perspective view of a two-dimensional scintillator based detector having masking strips according to the present invention.

Referring to FIG. 34, a similar masking approach may be applied to a two dimensional piece of scintillation material to form a detector 452 with the benefits described above. Specifically, a piece of scintillation material 454 has mask of lead applied in strips 456 to its face. Narrow vertical openings 458 are left to allow entrance of photons aligned with the openings. Like with the embodiment of FIGS. 14a–14c, this give increased accuracy. Photodetectors 459 are positioned behind the scintillation material 454 and are capable, by means such as "Anger logic", of detecting where a pulse of light occurs. Because a portion of the face is masked, the electronics "knows" that the photon did not strike in the masked areas and can therefore more precisely pinpoint the location of the strike. The masking off of certain portions of the detector surface reduces, in effect, the positional uncertainty of a given pulse of light, thus permitting its position to be determined more accurately and precisely.

Figure 32:
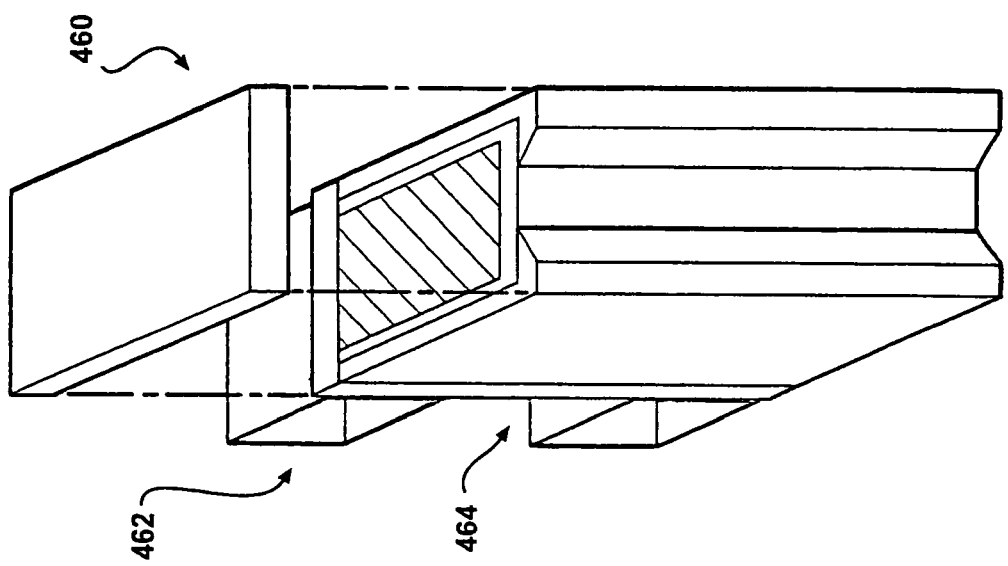
FIG. 32 is a perspective view showing construction details of a bar-shaped, masked detector module similar to FIG. 31A, but with photo-detectors placed along its rear face.

FIG. 32 shows details of construction of a bar-shaped, masked detector module 460 as described in the previous Figures but with the photo-detectors 462 attached at the rear face through use of optical coupling material 464. A similar masking configuration may be used with solid-state detector modules.

As will be clear to those of skill in the art, photo-detectors of various types are somewhat costly. Therefore, it is desirable to reduce the number required. According to another embodiment of the present invention, a pair or more of optical fibers may be attached to each of the scintillation-based detectors, with one fiber connected to each end of the detector. The fiber may be connected to the top and bottom and/or to the back face adjacent the top and bottom. The optical fibers may then be routed to a photomultiplier of the type have position sensitivity. These readily available multichannel photomultipliers are capable of providing distinct outputs for a multiplicity of locations across the face of an individual tube. Such a photomultiplier can then sense light pulses from a large number of optical fibers running from various detectors. In this way, the total number of photo detectors is reduced. A similar approach may be applied to two-dimensional scintillation based detectors. Rather than using photodetectors mounted to the rear of the material, multiple optical fibers may be used to route the light to multichannel detectors.

As previously discussed, the pieces of scintillation material that form the core of a scintillation based detector are clad in a radiolucent, light reflecting material such as aluminum. This increases the brightness of the pulse of light as perceived by the light detectors. However, in some situations, this reflectivity may interfere with the ability of the light detectors to determine the longitudinal position where the photon struck the scintillation material. Therefore, it may be beneficial to reduce the reflectance of one or more surfaces of the scintillation material. For this purpose, the surface may be roughened prior to cladding, the cladding may be roughened in certain areas, or a lower reflectance coating may be applied to either the scintillation material or the cladding. Alternatively, it may be desirable to vary the reflectance along the length of the reflector. For example, a roughed strip on one surface of the scintillation material may vary in width along the length of the detector. The strip could be narrow in the center, so that reflectance remains high, and wider near the ends so that reflectance is reduced. This increases the likelihood of events near the center being detected at the ends.

XIV. Detectors and Arc may Both Move

Figure 33:
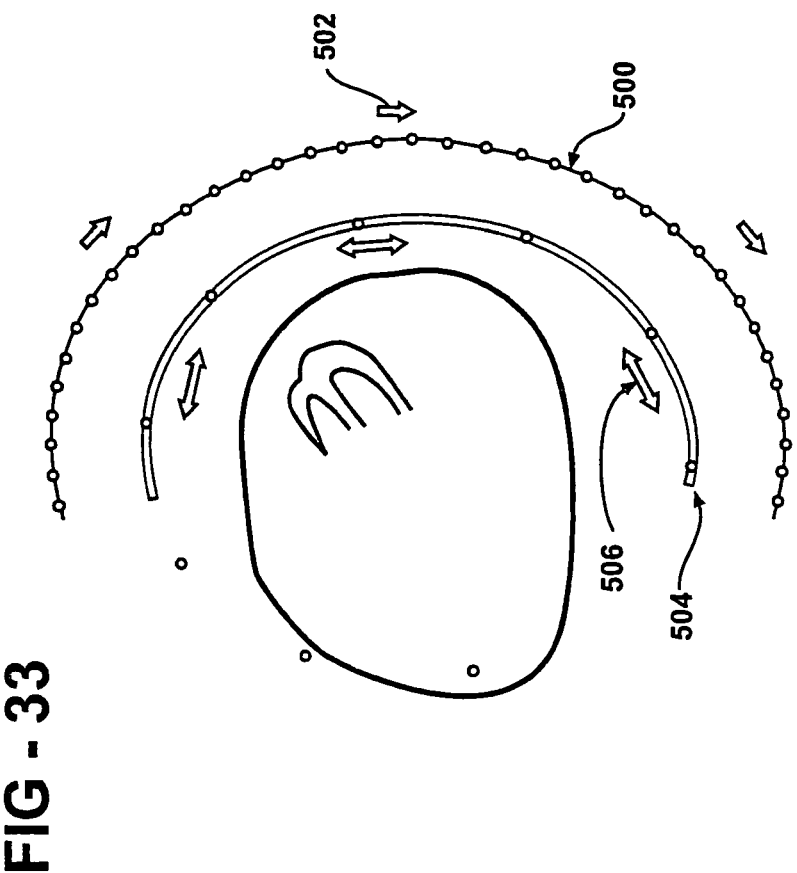
FIG. 33 is a diagrammatic representation of the directions of concurrent detector and aperture arc motion for one embodiment of the invention.

If the spacing of detector modules is sparse, gaps may be seen in the pattern of angular sampling provided by this system. The importance of such gaps depends on the number of angular "bins" of data obtained as the aperture arc moves. In addition, the significance of any artifacts caused by incomplete angular sampling depends on the clinical setting. If such artifacts are objectionable, this invention optionally provides for a means (FIG. 33) of rotation of the arc of detector modules 500 through a limited angular range 502, such motion occurring either continuously or in a limited number of discrete steps. The range of motion of the detector arc is equal to the spacing between detectors. At each step of detector motion, the aperture arc 504 is moved through its range of motion 506. In this manner, a full set of angular projections may be obtained with even sparse detector population.

As another alternative, a tomography system according to the present invention may be provided with a reduced number of detectors to reduce the cost of the system. This system would have either reduced resolution or would require an increased scan time. Later, the system may be upgraded by adding additional detectors at positions between the existing detectors.

XV. Calibration

Figure 35:
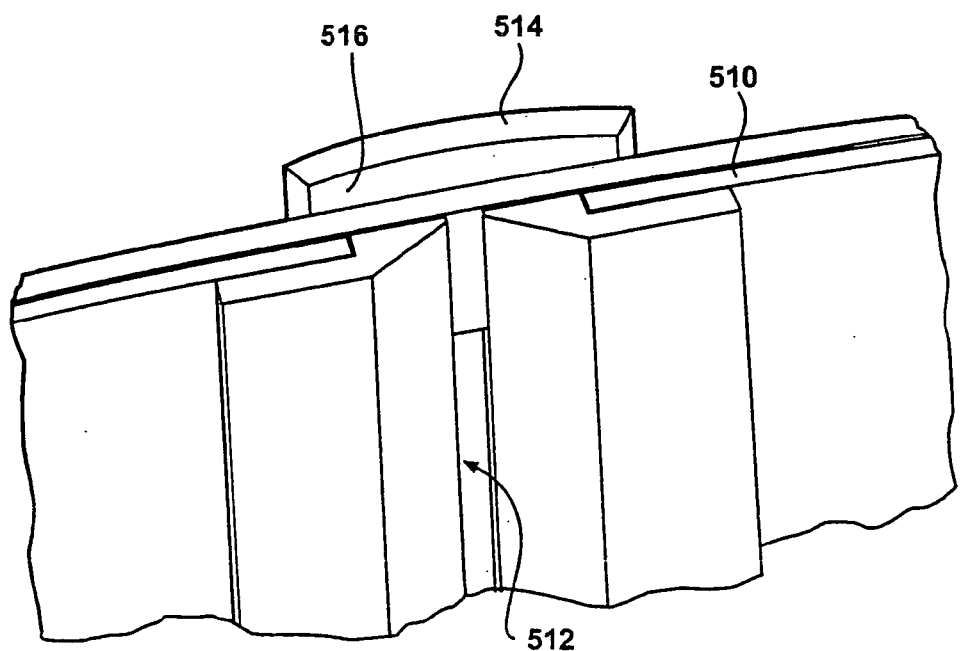
FIG. 35 is a perspective view of a portion of an aperture arc with a calibration module disposed by the aperture.

As known to those of skill in the art, nuclear medical imaging devices require regular calibration. With typical parallel hole gamma cameras, a sheet of material with radioactive substance on one side is positioned against the face of the collimator in order to perform a calibration. The present invention creates different challenges. A tubular radiation source could be positioned at the patient axis. However, calibration would then be very time consuming, since it would require long exposure times at each arc position over a number of positions. This would also lead to unacceptable levels of radiation in the room during the calibration process. FIG. 35 presents a preferred calibration approach. A portion of an aperture arc is shown at 510 with an aperture at 512. A calibration member 514 is shown positioned adjacent the aperture 512. It is arc-shaped, and may have a smaller radius and curvature than shown. The inside surface 516 has a radioactive material on it, and is positioned such that the radioactive material causes photons to travel through the aperture 512. This results in radioactive material covering the entire field of view of the sensors that can "see" the aperture. Obviously, multiple calibration members 514 are used, with one being placed at each of the apertures. This allows a rapid calibration of the device, allows for compact storage of the calibration devices, and minimizes the exposure to radiation.

XVI. Alternative Configurations

Figure 36:
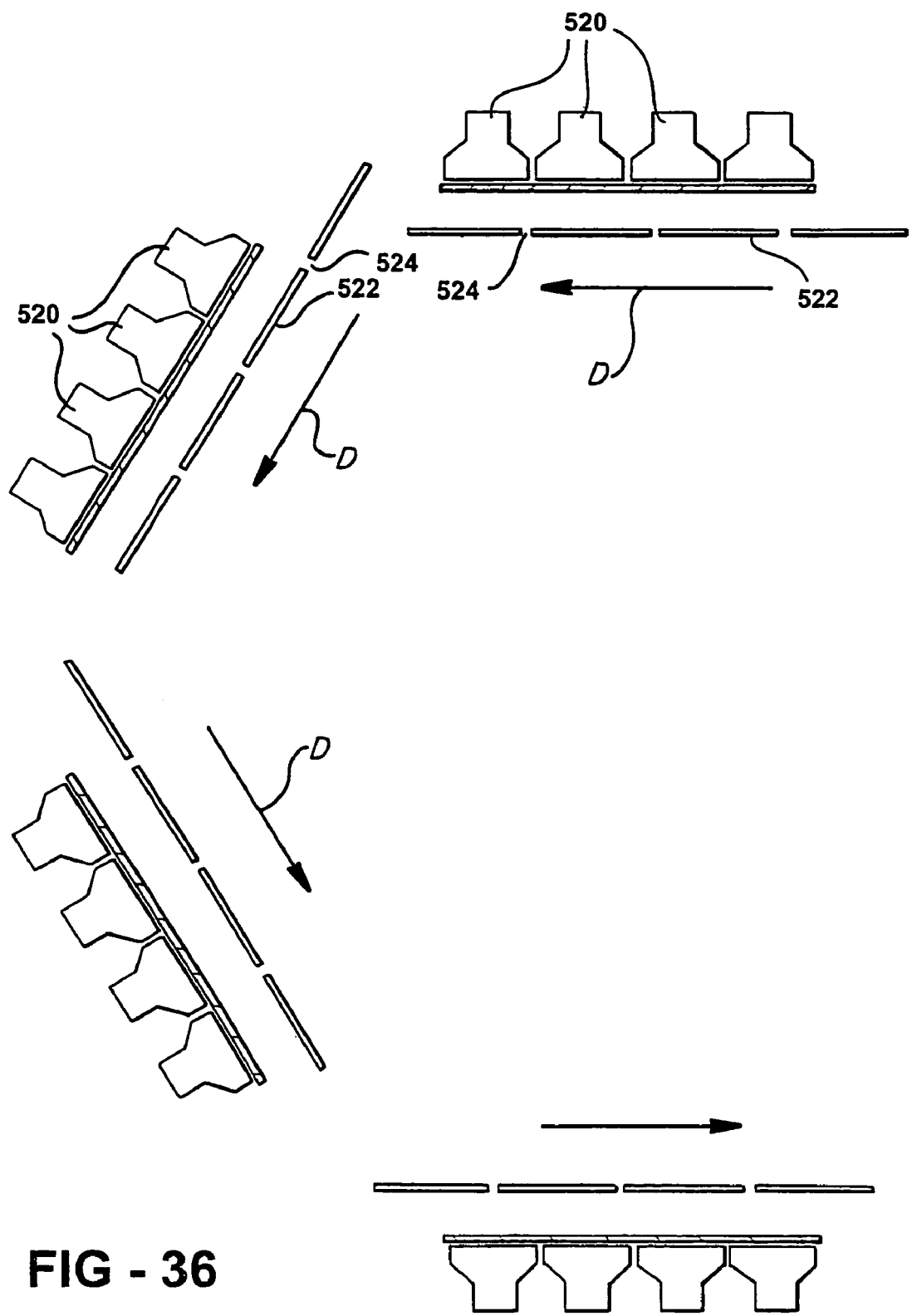
FIG. 36 is a top diagrammatic view of yet another embodiment of the present invention, which makes use of two-dimensional detectors and linear blocking members.

The previously described embodiments of the present invention have specified that the detector sensor arrays, the collimators, and the blocking member each be arcuate in shape. As will be clear to those of skill in the art, other shapes are also possible. For example, the detectors may be laid out in a rectangular or square arrangement. The blocking member and the collimators could be shaped likewise. As another example, sets of either strip or two-dimensional detectors may be arranged in straight rows at various positions around the field of view. This approach is shown in FIG. 36 using two-dimensional detectors 520. Each row of detectors 520 has a blocking member 522 in the form of a straight sheet positioned in front of it. The blocking member 522 has apertures, such as slots 524, defined through it and moves as shown by arrows D so that lines or response are swept across the field of view. Collimators, as discussed with other embodiments herein, may also be provided. As a further alternative, the detectors, either strip or two dimensional, may be arranged as shown in FIG. 36 and an arc or ring shaped blocking member may be used. This arrangement, or the arrangement of FIG. 36 may cover an arc between 180 and 360 degrees. In these embodiments, if two-dimensional detectors are used, conventional large two-dimensional detectors, as used in gamma cameras may be cut into several, preferably four, pieces to provide the smaller two-dimensional detectors necessary for these embodiments. This reduces the total cost of components.

Depending on the application, the system of the present invention may include other accessories. For example, in cardiac work, it may be desirable to stress the heart by having the patient perform an exercise. For this purpose, the system may include a bicycle ergometer that is either permanent or detachable. Also, the system may include an electrocardiogram and/or a built in cardiac defibrillator. Also, an intravenous infusion pump may be included or be attachable.

XVII. Structural Considerations

Figure 37:
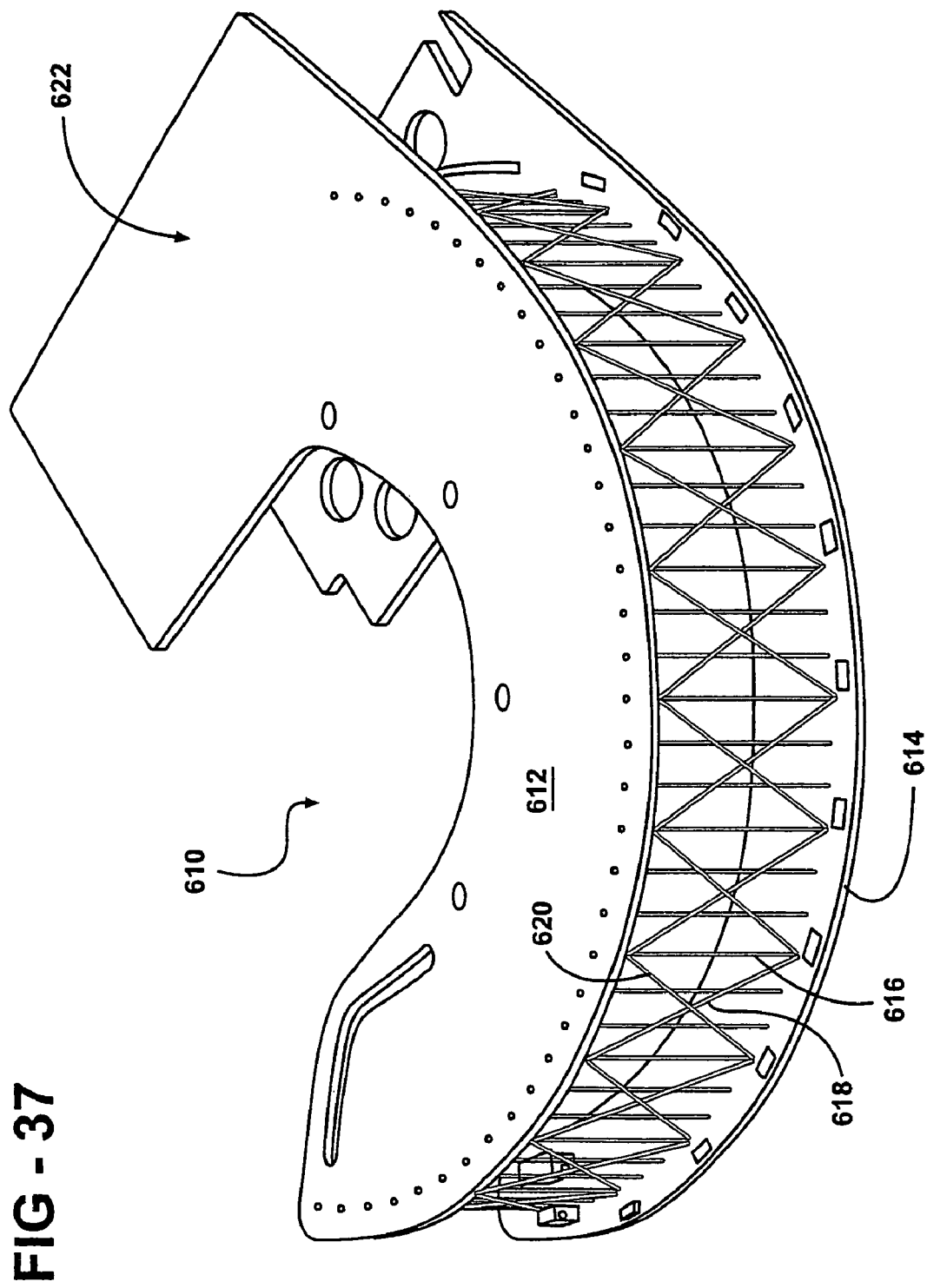
FIG. 37 is a perspective view of an imaging arc.

FIG. 37 shows a support assembly for an imaging arc 610 similar to the one shown in FIG. 18. However, FIG. 37 shows the arc having diagonal spokes or tension members running in an additional directional between an upper support member 612 and a lower support member 614. The spokes may be considered to include a vertical set and a first and second diagonal set. A horizontal spoke representative of spokes in the vertical set is labeled 616. A spoke representative of the spokes in the first diagonal set is labeled 618, and a spoke representative of the spokes in the second diagonal set is labeled 620. As shown, each set includes a plurality of similarly positioned spokes arranged along the arc and extending between the upper and lower support members 612 and 614. While the arc 610 may be constructed with all three sets of spokes, it may also be constructed with only one or two sets of spokes. In one preferred embodiment, only the second set of diagonal spokes, as represented by 620, are provided. As discussed previously, the support assembly 610 has a base portion or fixed end 622 that is attached to the rest of the imaging apparatus of the present invention, with the remainder of the arc extending away from the base 622 to a free end. In some embodiments, the remainder of the arc 610 is unsupported, and therefore must be self-supporting. Because the arc 610 may be quite heavy, it is necessary to construct it so as to resist sag and twist along its length. By providing the spokes as represented by 620, some compensation for sag of the arc may be provided. As will be clear to those of skill in the art, by tightening the spokes 620, the cantilevered free end of the arc 610 may be raised relative to the position it would take if the spokes are loosened. In some cases, the spokes as represented by 616 and 618 may also be provided to provide additional structure or to provide for other compensation.

The arc 610 preferably includes a collimator that is constructed with multiple sheets of plastic and lead. Experimentation has shown that if the upper support member 612 and lower support member 614 are not pulled tightly together, the end of the arc may be raised somewhat which causes the individual sheets in the collimator assembly to slide very slightly relative to one another. If the two support members 612 and 614 are then compressed against each other, the individual sheets of the collimator assembly lock to one another and greatly increase the stiffness of the overall arc 610. Therefore, the arc may be moved into a preferred position, such as by using a fixture, and then various spokes may be tightened to clamp the upper plate 612 and lower plate 614 tightly to one another.

Figure 38:
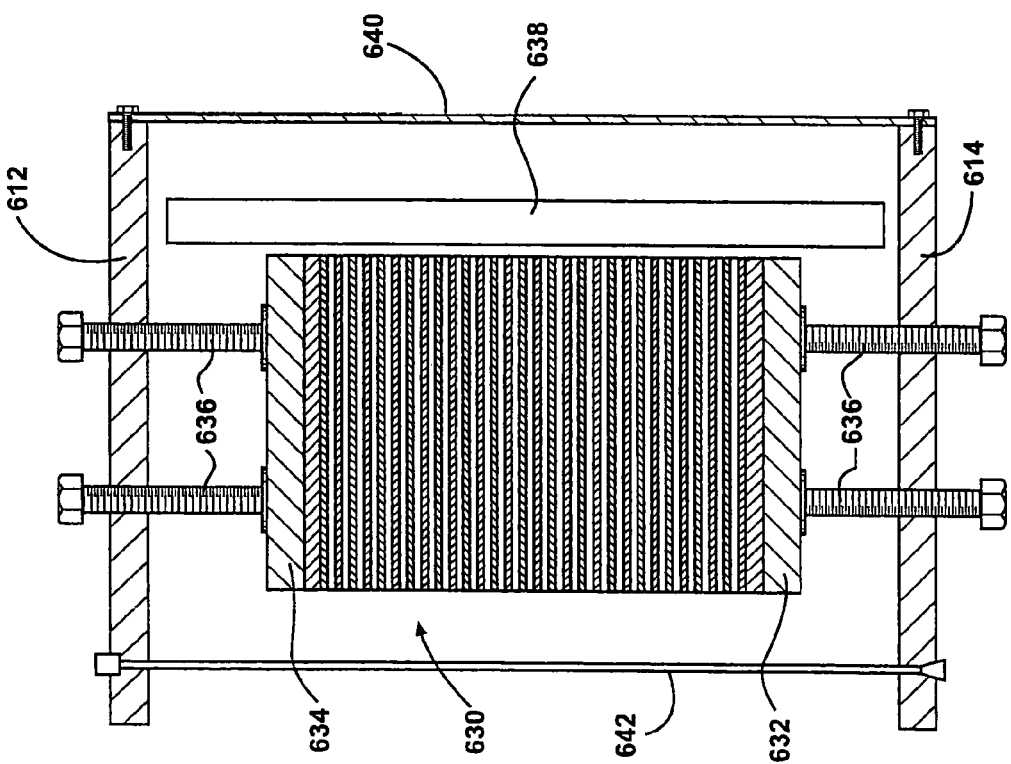
FIG. 38 is a cross-sectional view of one embodiment of an imaging arc according to the present invention.

Referring to FIG. 38, a cross-section of the arc is shown. In this embodiment, the collimator assembly 630 is constructed with a plurality of alternating layers of lead and plastic supported between a lower support plate 632 and an upper support plate 634. Threaded adjusting members 636 extend through the lower plate 614 to the lower support member 632 and through the upper plate 612 to the upper support member 634. The various parts may not be to scale. By adjusting the adjusting members 636, the position of the collimator assembly 630 may be adjusted relative to the remainder of the arc. As will be clear to those of skill in the art, the adjusting members are provided at a plurality of locations along the length of the arcs, so that the position of the collimator assembly may be adjusted throughout the length of the arc. By adjusting the various adjusting members 636, the sag of the collimator assembly along this length may be compensated for. In addition, any twist in the collimator assembly may be adjusted out. Preferably, the collimator assembly is adjusted such that each vane is substantially planar.

FIG. 38 shows the aperture arc 638 positioned between the collimator assembly and the patient side of the arc. The patient side of the arc may have a thin sheet of radiolucent material, such as aluminum, as shown at 640. This thin piece of material 640 ties the upper support member 612 to the lower support member 614 so as to provide a structurally sound arc. A single spoke 642 is shown on the side of the arc away from the patient, and represents one of the spokes as illustrated at 616–620.

Figure 39:
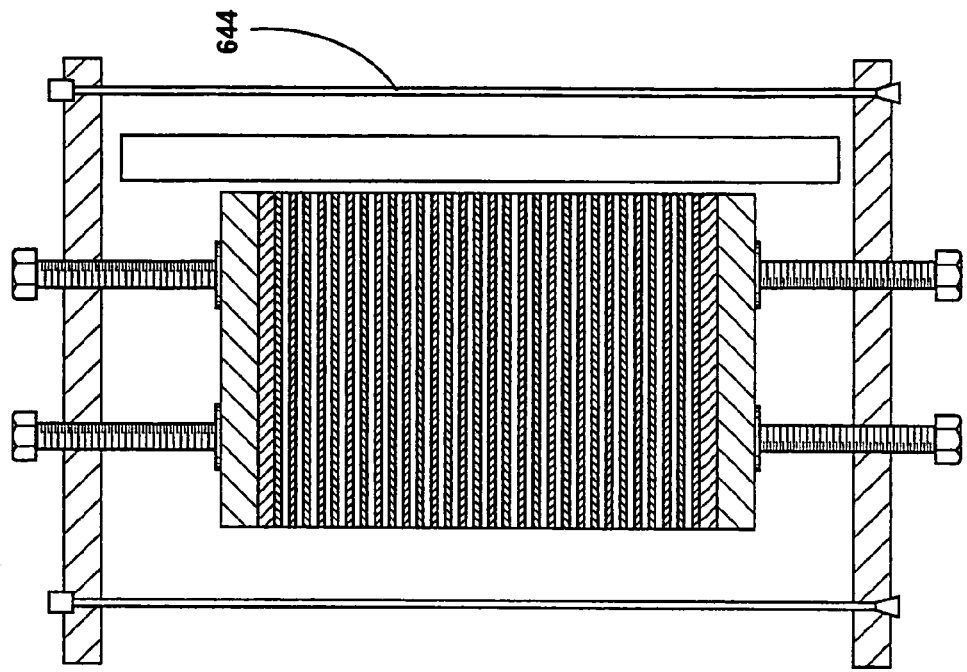
FIG. 39 is a cross-sectional of another embodiment of an imaging arc according to the present invention.

FIG. 39 shows an alternative embodiment where the thin piece of material 640 is replaced by an additional spoke 644. The sheet of material 640 in FIG. 38 is preferred, as it provides a slight uniform reduction in transmission of photons, whereas the use of spokes causes a localized reduction in the passage of photons. However, as will be clear to those of skill in the art, the machine may be calibrated such that the presence of spoke 644 may be compensated for.

Figure 40:
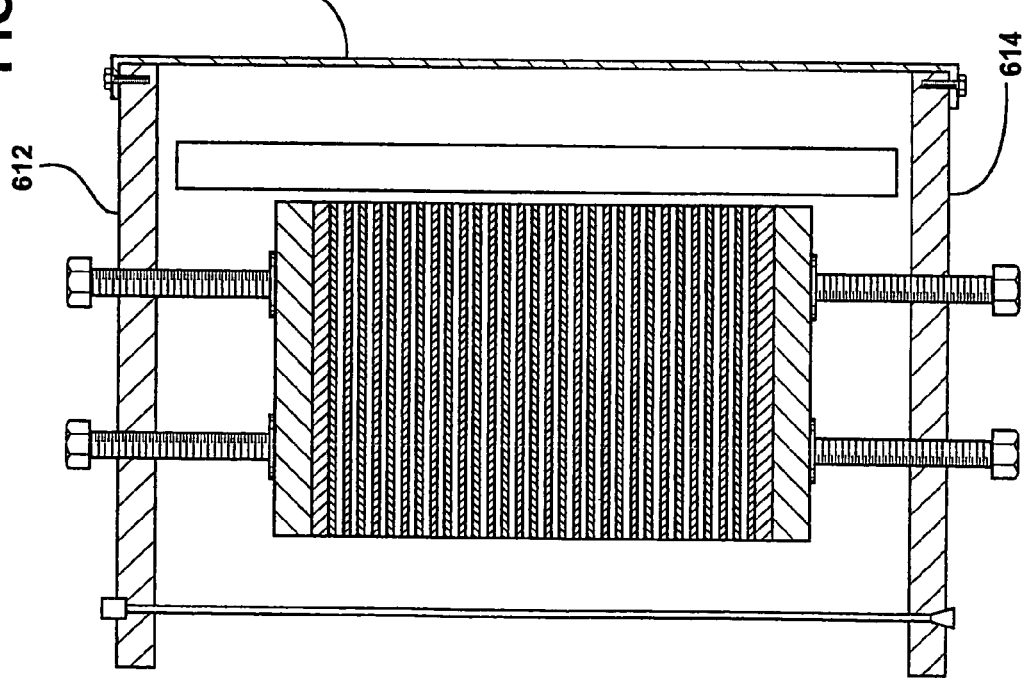
FIG. 40 is a cross-sectional view of yet another embodiment of an imaging arc according to the present invention.

FIG. 40 illustrates an alternative embodiment where the sheet on the patient side of the arc, here labeled 646, bends around the top of the upper support member 612 and around the bottom of the lower support member 614. This is a preferred construction as it provides easier attachment of the fasteners.

XVIII. Rebinning of Data

As will be clear to those of skill in the art, the imaging system according to the present invention provides data in a form different than current imaging cameras, which have generally rectangular flat faces. These traditional cameras take images from multiple angles, with each image providing a two-dimensional "picture" of the patient from that angle. In the present invention, photons are received from multiple angles by the multiple detectors, with the lines of response for the various detectors being swept across the patient area as the aperture arc and detectors move relative to one another. Because the imaging is accomplished in a different manner, it is preferred to initially process the data from the present invention such that the data is put in the format used with current machines. Then, traditional reconstruction software may be used to process the resulting data. This interim step of formatting the data into the format currently provided by imaging devices is referred to herein as "rebinning."

Figure 41:
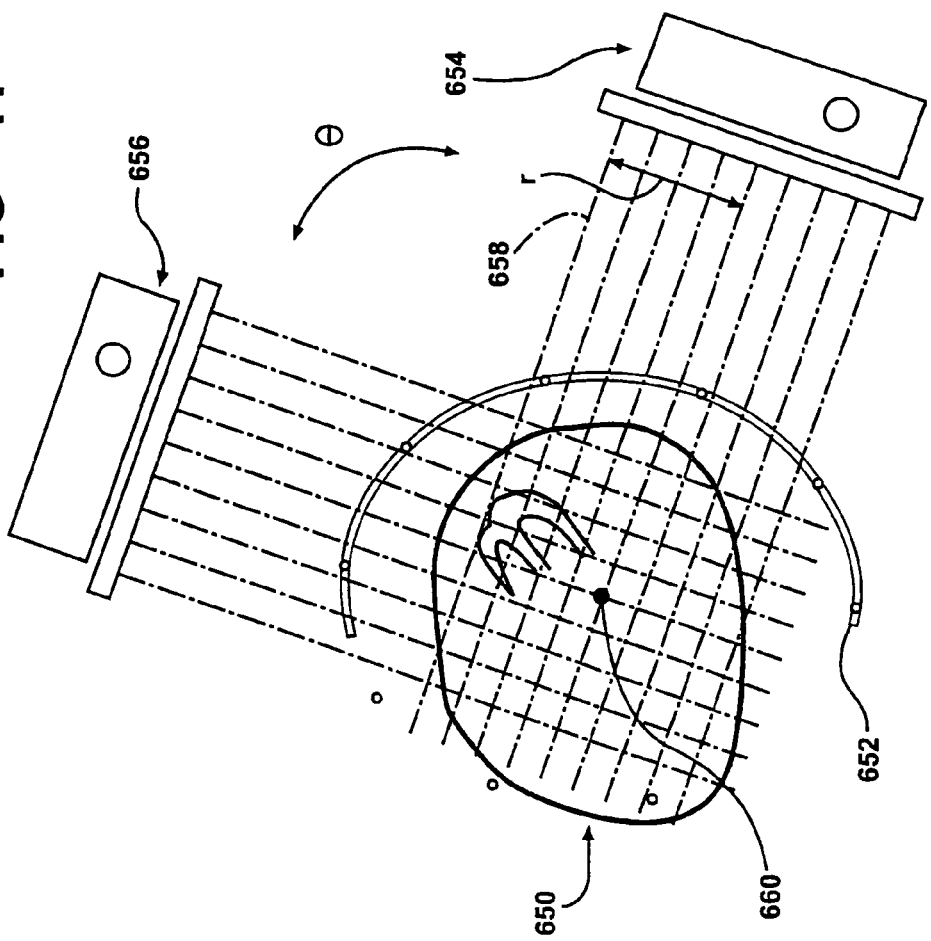
FIG. 41 is a schematic view of a patient field of view along with a traditional gamma camera shown in two different positions.

In order to understand the rebinning of data in accordance with the present invention, it is best to first discuss how data is treated in traditional imaging devices. FIG. 41 illustrates a cross-section of a patient 650. A portion of an arc 652, which forms part of some embodiments of the present invention, is shown surrounding part of the cross-section of the patient 650. A traditional two-dimensional imaging camera is shown schematically as 654 in a first position and again as 656 at a position 90 degrees from the first position. A plurality of parallel imaging lines is shown projecting from each camera 654 and 656. In processing data from the camera indicated at 654 and 656, the position of incoming photons is generally designated using r and θ. These variables refer to the distance of the incoming photon from the center of the detector, r, and the angular position of the camera, θ. One of the incoming photon paths is labeled as 658 in FIG. 41. The distance of the path of this photon from the center of the camera in position 654 is marked as r in the drawing. This data may be plotted in a graph referred to as the sinogram. A sample sinogram is shown in FIG. 42. A sinogram plots the position from the center of the imager, r, with zero being in the center, versus the angular position of the camera, θ. If a point 660 in the very middle of the imaging area is the only point emitting photons, a sinogram will be a straight vertical line as shown in FIG. 42. That is because the photons emitted from the single point 660 will strike the center of the camera (r=0) at all angular positions of a camera (θ=0 to 360 degrees). FIG. 43 illustrates a sinogram for a single off center point. As the imaging camera rotates about the imaging area, the off center point appears to move side-to-side with respect to the center of the camera, thereby giving a sine-shaped curve on the sinogram.

Referring again to FIG. 41, the cross-sectional slice illustrated as 650 may be considered to be a single horizontal slice, if the patient is positioned vertically. Obviously, a sinogram resulting from an actual patient imaging session will be significantly more complex than shown in FIGS. 42 and 43. In addition, sinograms may be created for each "slice" of a patient. As discussed previously, the field of view in which the patient is positioned may be defined as having a longitudinal axis. The "slice" of the patient will typically be perpendicular to this longitudinal axis. This may also be referred to as a sensing plane. As will be clear to those of skill in the art, multiple sensing planes may be defined so as to obtain different "slices" of the patient. Referring again to FIG. 41, it will be appreciated that the distance r may be defined as the distance in the sensing plane between a center point or center line of the camera and the position where the photon is received. In order to define the angular position of a traditional gamma camera, a position line may be defined as extending perpendicularly between the longitudinal axis and the center line of the camera in the sensing plane. The angle θ may then be defined as the angle between the position line and an arbitrary base line also contained in the sensing plane and perpendicular to the longitudinal axis.

Referring back to FIG. 9B, it can be seen how the lines of response of various detectors in the present device are swept across the field of view as the aperture arc and the detectors move relative to one another.

FIG. 44 illustrates what may be considered a sinogram for an imaging system according to the present invention with an aperture arc having six apertures. If a single point is imaged, and the data is plotted on a chart of aperture arc position versus the position on the detector array where the photon is sensed, a plurality of angled parallel lines will be created. This is because as the aperture arc position moves, the position on the detector array where a photon from the point source can reach the detectors is also moved in a generally linear relationship. It should be noted that FIG. 44 is not to scale, but is intended only to represent a general concept. In order to treat data such as shown in FIG. 44 using algorithms designed for data presented in the format of FIGS. 42 and 43, the data must be resorted or rebinned.

Figure 45:
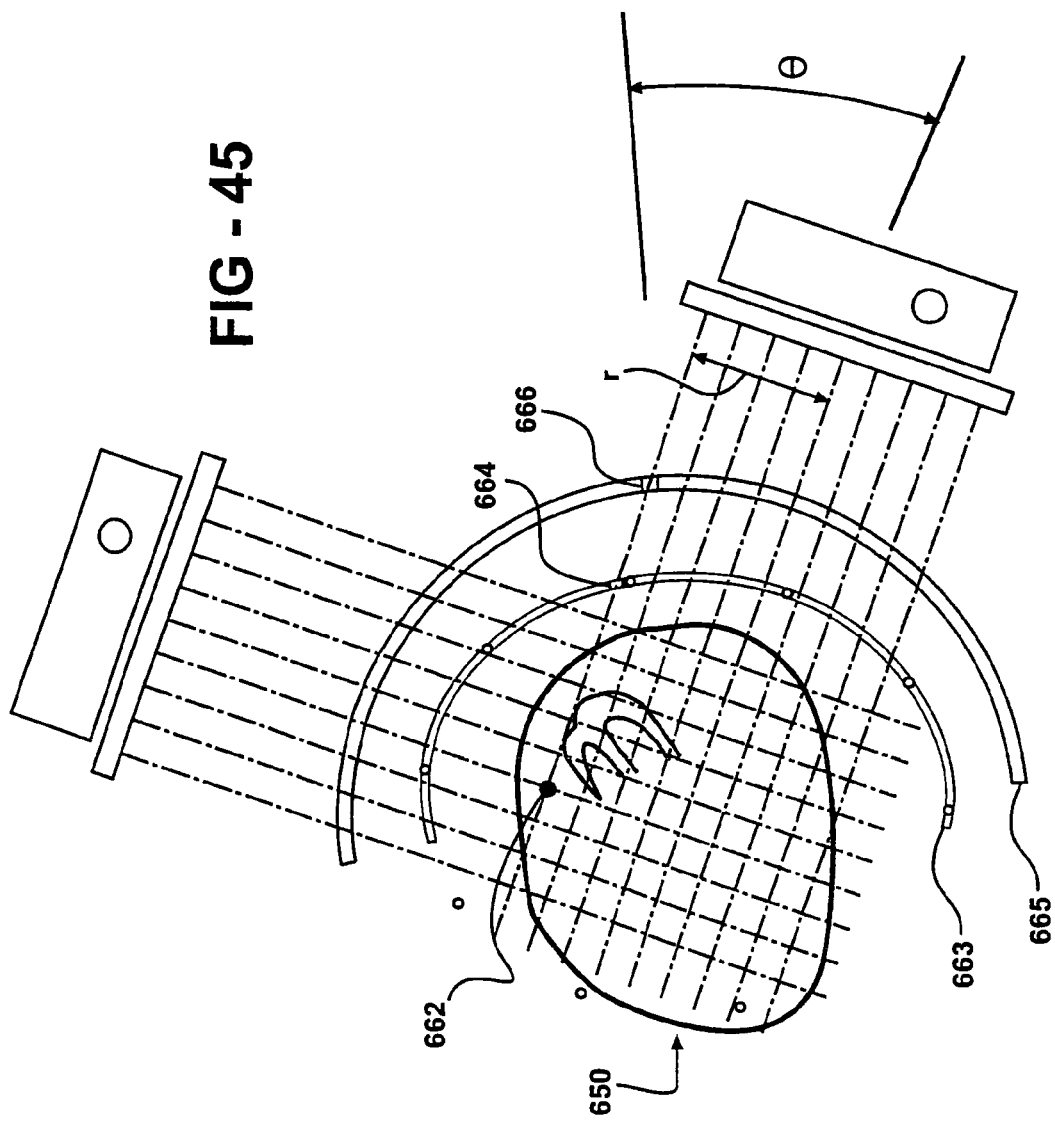
FIG. 45 is a schematic similar to FIG. 41 showing the equivalent aperture arc and detector arc positions for the present invention.

Referring to FIG. 45, the slice 650 is shown with an emitting point 662. An aperture arc 663 with an aperture 664 surrounds the imaging area, with a detector arc or assembly 665, with a detector 666, surrounding the aperture arc. A photon emitted from point 662 will pass through the aperture 664 and be received by the detector or sensor at 666. Because the position of the aperture 664 and the detecting position 666 are known, the equivalent positional data, r and θ, for a two-dimensional camera may be computed. This equivalent r and θ is shown in FIG. 45 for a two-dimensional camera.

Figure 46:
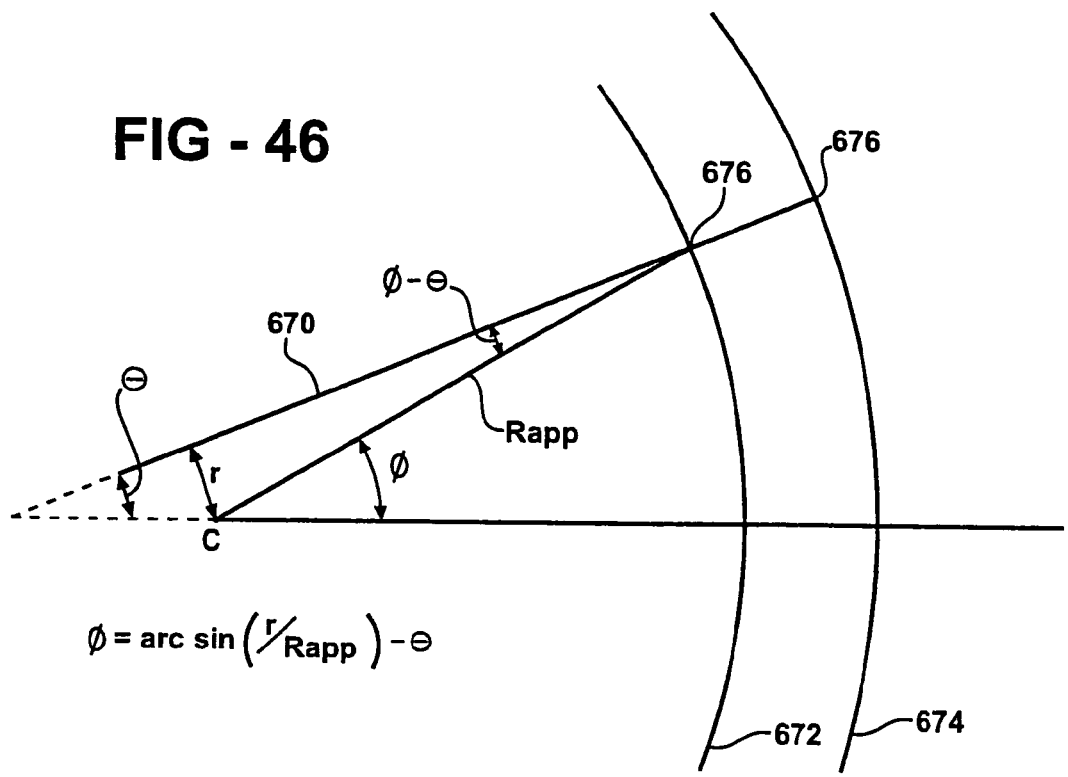
FIGS. 46 and 47 are schematics showing the geometry necessary for conversion of positions of the aperture arc and detector arc for use with traditional two-dimensional data processing.

Referring now to schematic FIG. 46, a photon path is shown at 670, with an aperture arc shown at 672 and a detector assembly or arc shown at 674. As shown, the photon path 670 will pass through an aperture at 676 and strike a detector at 678. The center of the aperture arc is shown at C, with the equivalent r and θ for a two-dimensional imaging camera being indicated on the diagram. C also represents the center of the field of view, and may lie on the longitudinal axis. The angle of the aperture 676 is expressed as φ, while the radius of the aperture arc is indicated as $R_{app}$. The relationship between these variables is given by the equation:

$$\phi = \arcsin\left(\frac{r}{R_{app}}\right) - \theta$$

Figure 47:
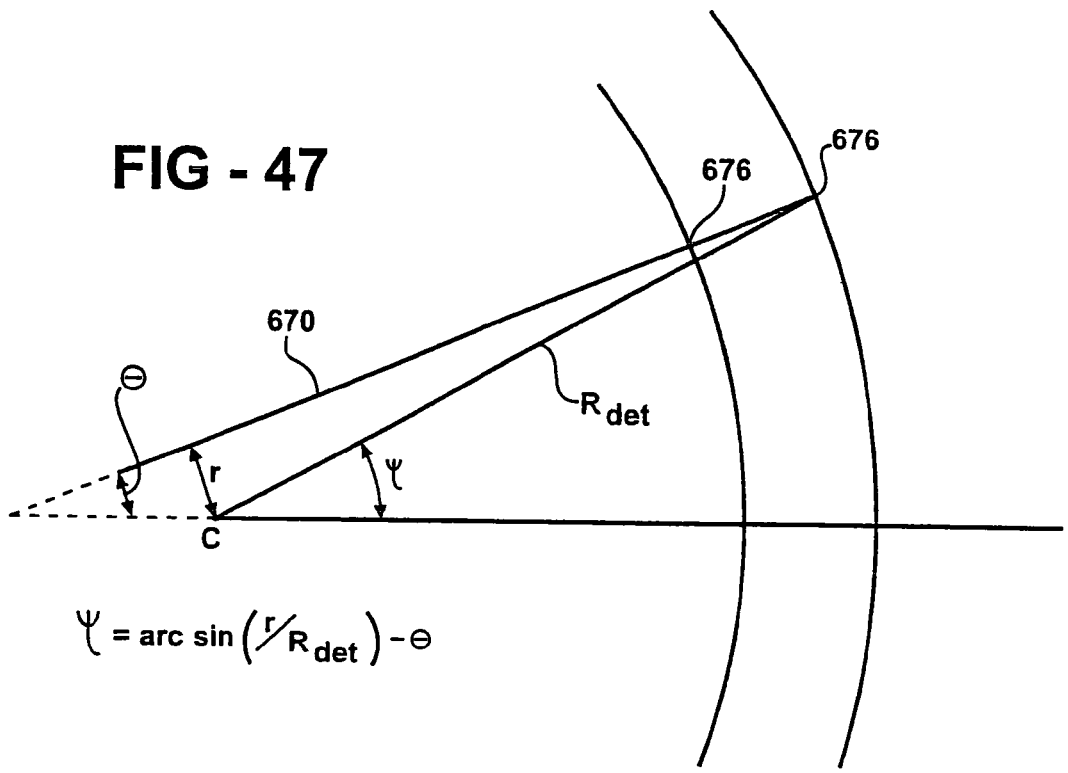

FIG. 47 illustrates a similar relationship for the position of the detector arc 678. In this case, the radius of the detector arc is given as $R_{det}$ and the angle of the position on the detector arc is given as Ψ. The relationship between the variables is given by:

$$\Psi = \arcsin\left(\frac{r}{R_{det}}\right) - \theta$$

As will be clear to those of skill in the art, sinograms may be created for each slice of the patient by plugging in values for θ and r for each position on the sinogram into the equations shown in FIGS. 46 and 47. In each case, this will provide an aperture position φ and a detector position Ψ. The intensity recorded for this combination of aperture position and detector position may then be entered in the sinogram for this combination of θ and r. This may be repeated until a complete sinogram is created. Once a sinogram is created, the data may be processed as with traditional imaging devices. As will also be clear to those of skill in the art, the rebinning may be accomplished using a computing device.

XIX. Additional Calibration Configurations

As discussed with respect to FIG. 35, it is desirable to provide some type of calibration source for calibrating an imaging system according to the present invention. In traditional two-dimensional imaging cameras, a flat sheet radioactive source is typically laid on top of a collimator, which is aimed upwardly. This calibration source exposes the entire surface of the camera to the same level of radioactive emission, such that the camera could be calibrated. That is, software adjustments may be made if a certain portion of the camera reads high or low with respect to other portions of the camera, such that after calibration, the resulting readout is uniform. These traditional calibration approaches have several drawbacks. First, the radioactive calibration source is large and heavy, and often difficult for technicians to manipulate. They are typically stored in large lead boxes to avoid excess radioactive exposure. However, due to the size and weight of the box, the technician is often forced to leave the box in one location and then carry the radioactive source, next to their body, into the room where imaging is actually done. This is inconvenient and leads to additional radioactive exposure by the technician. In addition, the collimator positioned between the calibration source and the sensing surface of the camera allows a passage of only about one in every ten thousand photons to reach the sensing surface. Therefore, the calibration procedure is often time-consuming.

FIG. 35 presents one approach to calibrating the present invention. Additional approaches will be discussed hereinbelow. In each case, a radioactive source is provided in or adjacent an aperture of the aperture arc such that radiation is projected through the aperture arc, through the collimator, and to the detectors. Because of the design of the present invention, a much higher ratio of emitted photons reach the various detectors, allowing for reduced calibration time. After the radioactive calibration source is positioned, the aperture arc is moved and software may be used to calibrate the imaging system to adjust for the variations in detector sensitivity and for the fact that photons intercept the detectors at different angles depending on the position of the detectors relative to the aperture arc.

Figure 48:
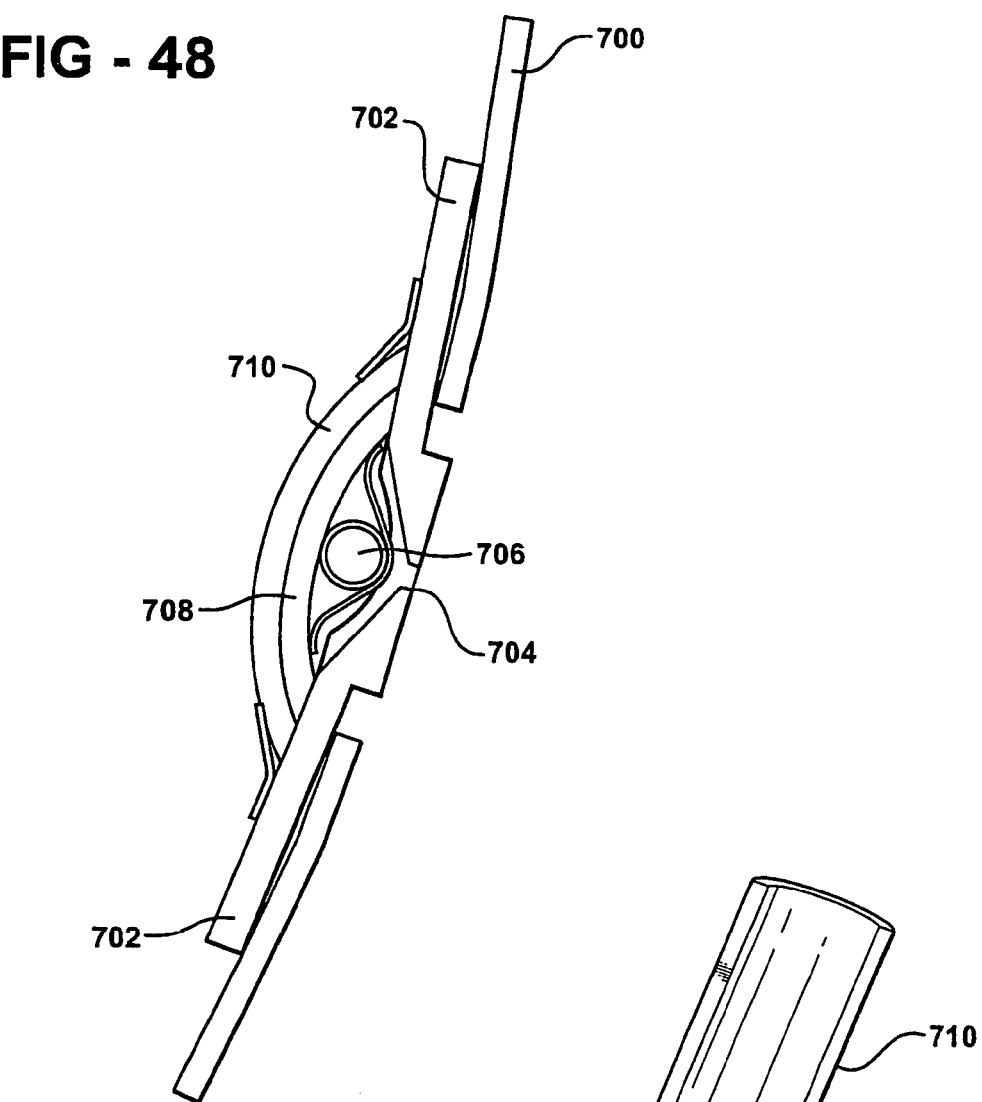
FIG. 48 is a top view of a portion of an aperture arc with one embodiment of a radioactive calibration source and holder.
Figure 49:
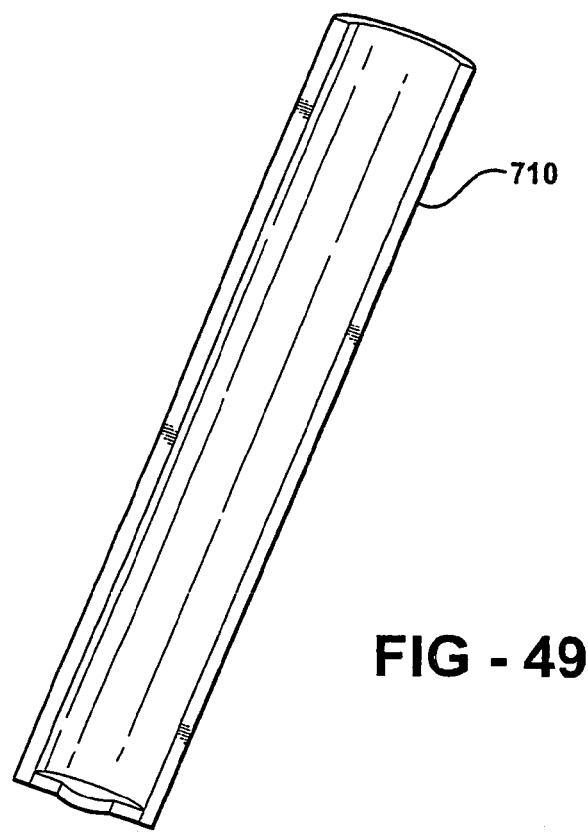
FIG. 49 is a perspective view of the outer shell or holder portion of a calibration source.
Figure 50:
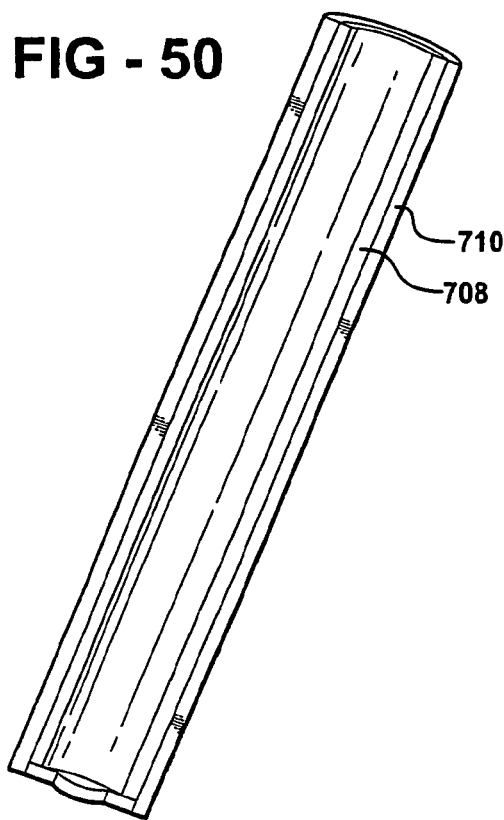
FIG. 50 is a perspective view of the holder of FIG. 49 with a photon blocking shield added.
Figure 51:
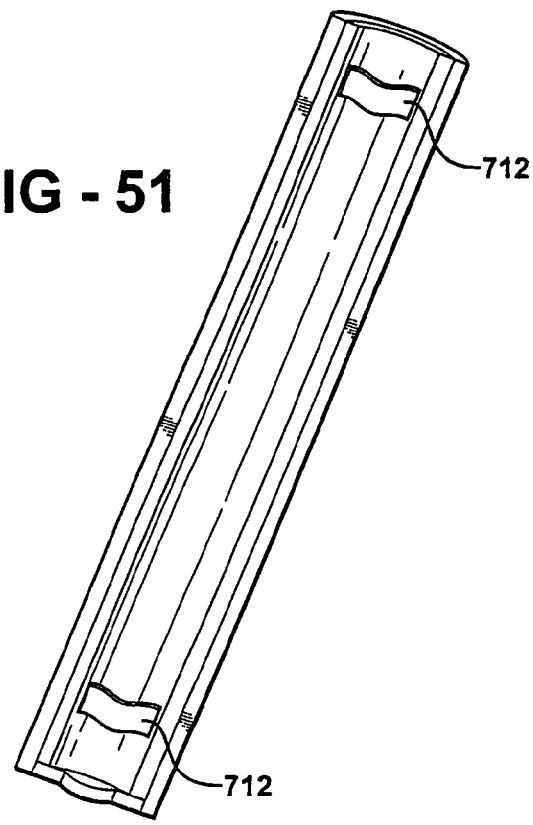
FIG. 51 is a perspective view similar to FIGS. 49 and 50 with the addition of radiation source retainers.
Figure 52:
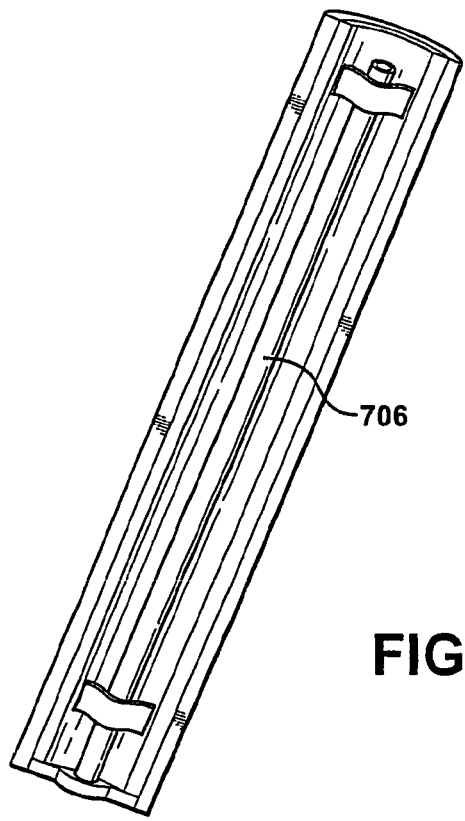
FIG. 52 is a perspective view similar to FIGS. 49–51 with a cylindrical radiation source added.
Figure 53:
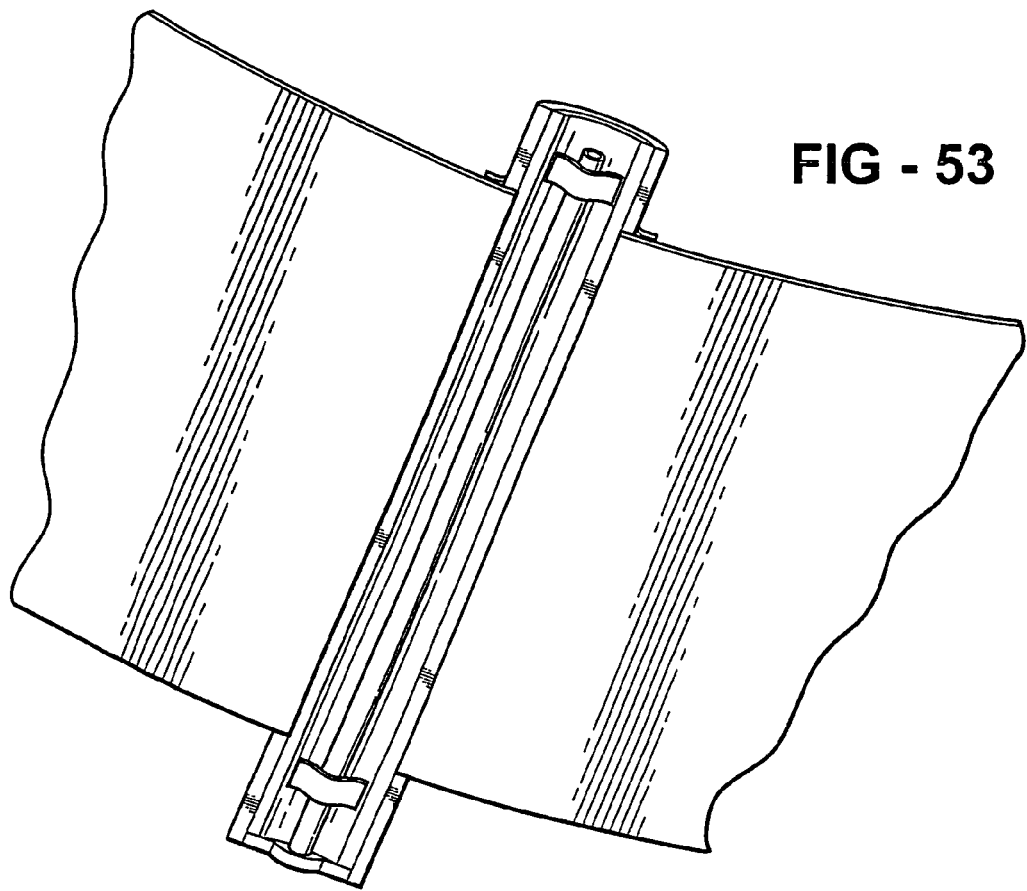
FIG. 53 is a perspective view of the calibration source of FIG. 52 attached to a portion of an aperture arc.
Figure 54:
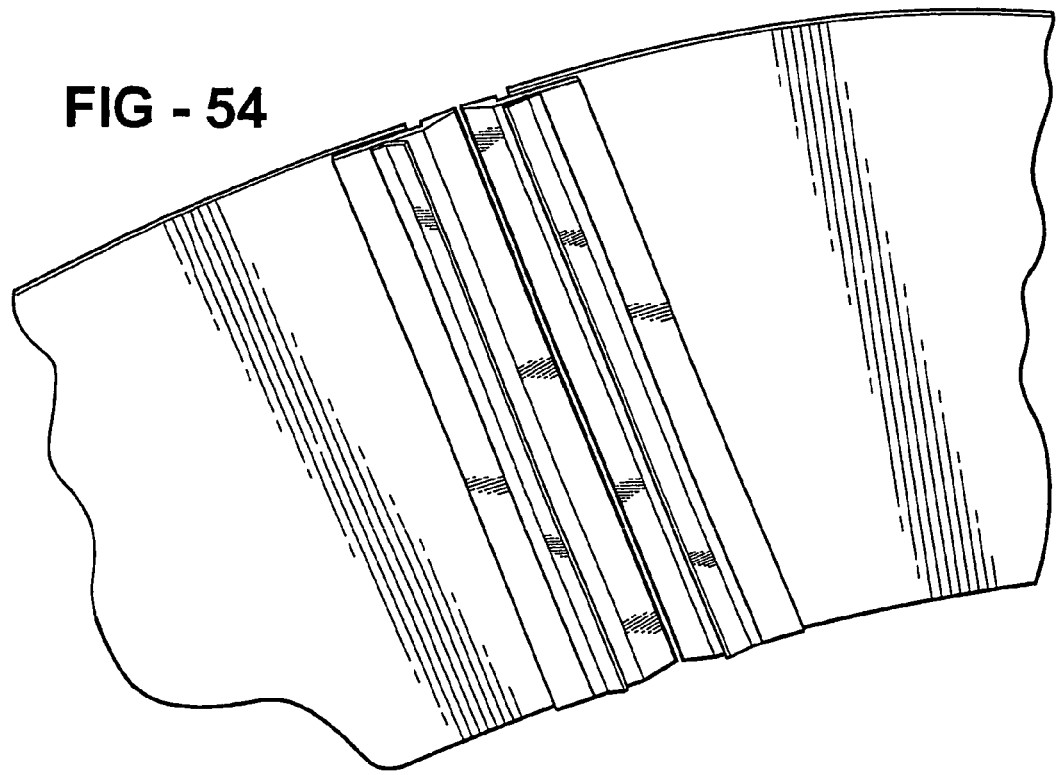
FIG. 54 is a perspective view of one side of a portion of an aperture arc showing receivers for receiving the calibration source.
Figure 55:
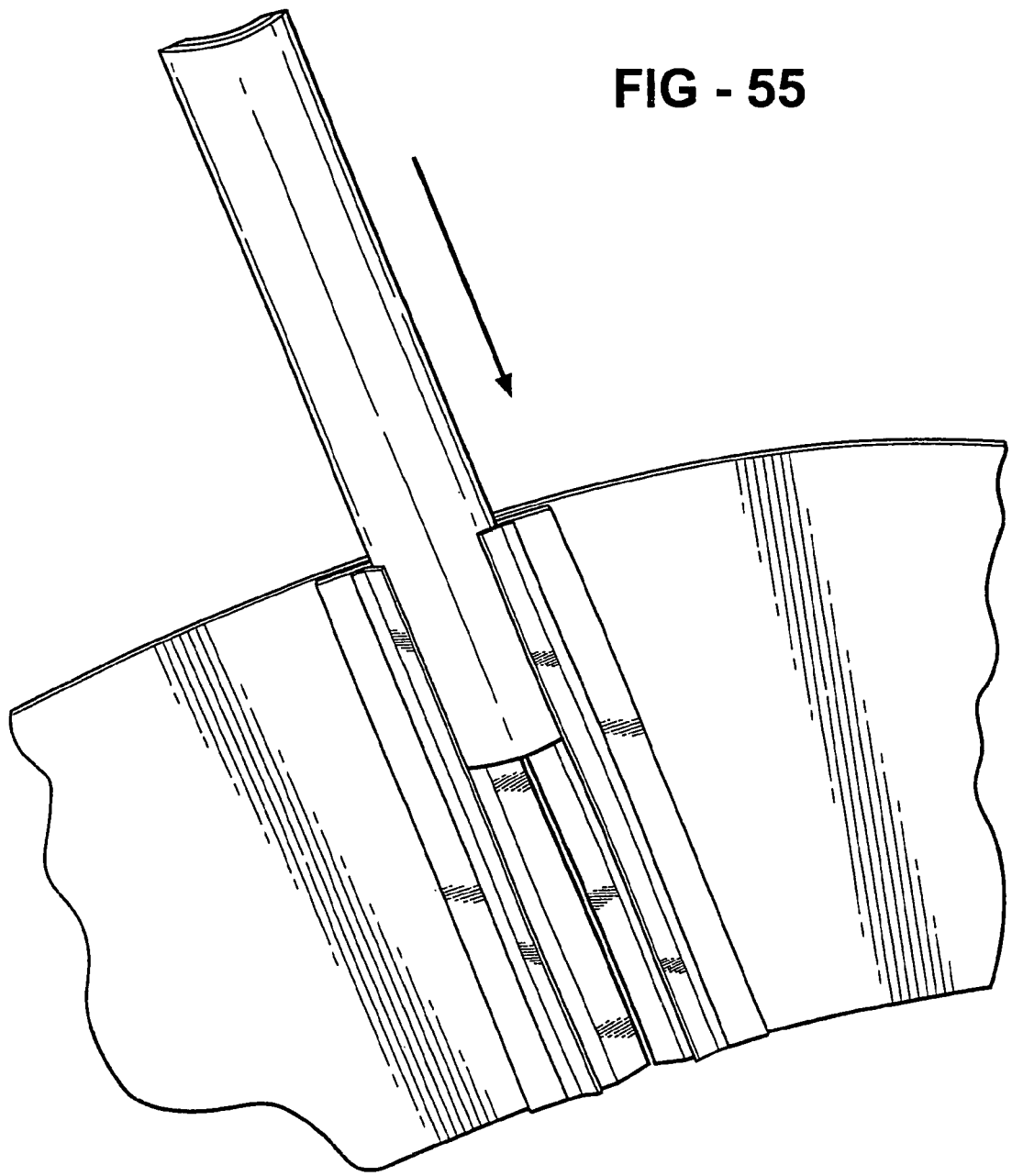
FIG. 55 is a perspective view similar to FIG. 54 illustrating the calibration source being inserted into the holders.

Referring now to FIG. 48, an alternative calibration source will be described. A portion of an aperture arc is shown at 700 with a pair of slot edge pieces 702 defining a slot 704. The calibration source includes a generally tubular radioactive source 706 which is attached to a carrier including a lead shield 708 and a plastic carrier 710. FIGS. 49–55 show the assembly and use of this calibration source. FIG. 49 shows the plastic carrier 710. As shown, the carrier is arcuate with a concave inner face. FIG. 50 shows the similarly shaped lead carrier shield 708 nested in the plastic carrier 710. In some embodiments, the lead shield is approximately 2½ to 3 mm thick. Alternatively, the shield may be formed of tungsten, which allows it to be thinner for the same amount of radioactive blocking. The radioactive source may be connected to the carrier in a variety of ways. FIG. 51 shows the use of clips 712 which may hold the source. Alternatively, it may be attached by gluing or by plastic coating the entire front side of the carrier to hold the source in place. FIG. 52 shows the source itself 706 held by the carrier. The source may be a tube filled with a radioactive material such as cobalt particles embedded in an epoxy or other resin. FIG. 53 shows the calibration source positioned in the aperture arc, with the side edge pieces removed for visibility. FIG. 54 shows the aperture arc with the side pieces installed. FIG. 55 shows the radioactive source being slid into a pair of guide pieces to position it for calibration. The aperture arc may be moved side-to-side during the calibration process. While the calibration source is shown as having a height taller than the aperture arc, it may also have a height equal to or shorter than the height of the aperture arc.

Figure 56:
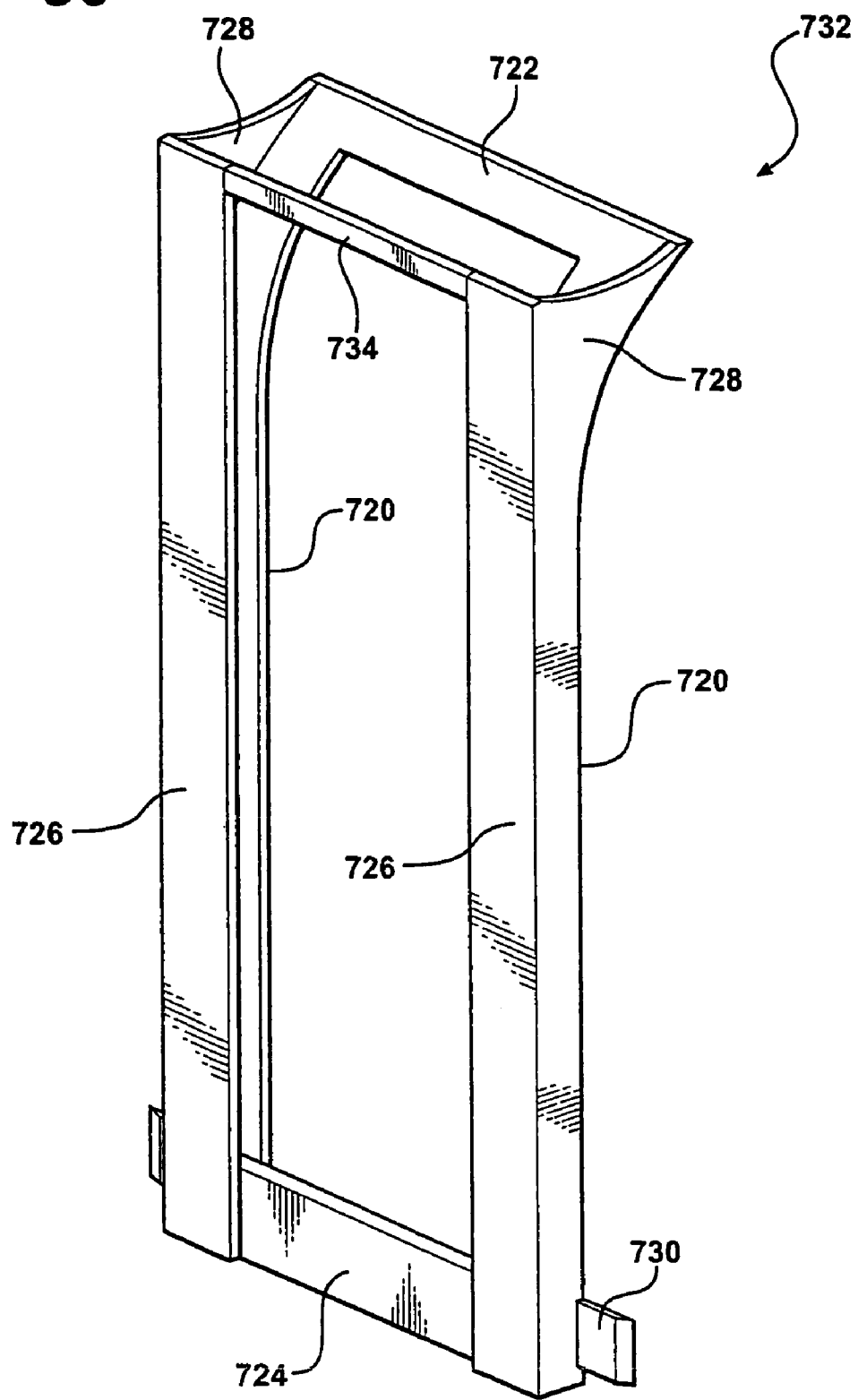
FIG. 56 is a perspective view of an alternative embodiment of a calibration source holder.
Figure 57:
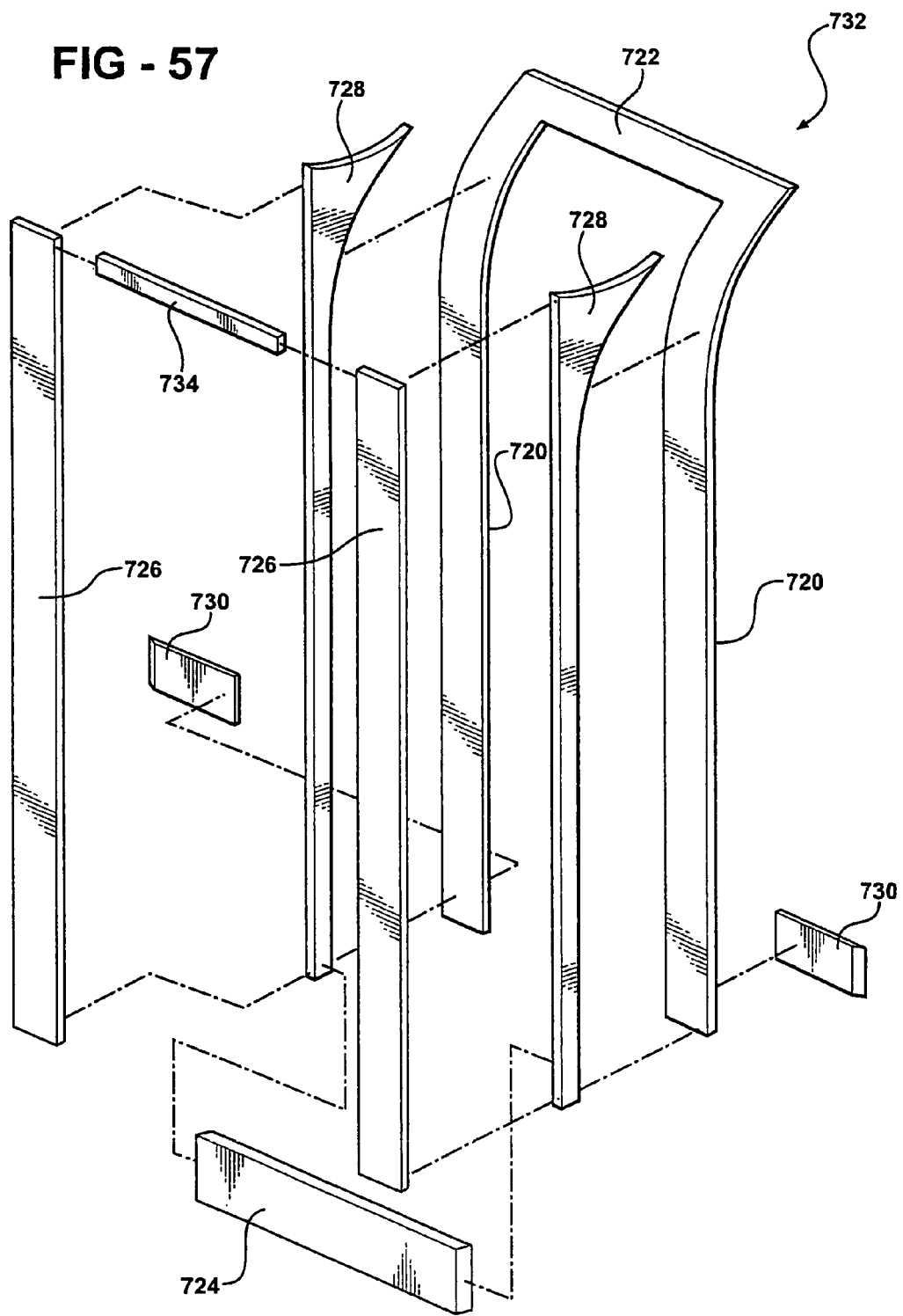
FIG. 57 is a perspective exploded view of the holder of FIG. 56.

As will be clear to those of skill in the art, the aperture arc is housed inside the imaging arc such that access to the arc is not easily provided for positioning of the calibration source. A series of figures starting with FIG. 56 illustrates the assembly, positioning, and use of a calibration source and holder or carrier for the source. FIG. 56 shows the assembled holder 732. It includes a pair of side rails 720 with curved upper ends positioned parallel to one another. The side rails 720 are tied together at their top and bottom by interconnecting portions 722 and 724. The bottom interconnecting portion 724 also acts as a spacer and may be said to be positioned on the inside of the side rails. A pair of inner rails 726 connect to the bottom spacer 724 and extending generally parallel upwardly and spaced from the side rails 720. A pair of slots is defined between the inner rails 726 and the side rails 720. The open sides of the slots are closed by closure members 728. Support flanges 730 are positioned adjacent the bottom of the assembled device. A front cross piece is shown at 734. In one embodiment, the cross piece 734 includes a magnetic latch for locating the carrier or holder 732 during use. FIG. 57 illustrates the carrier 732 in exploded view.

Figure 58:
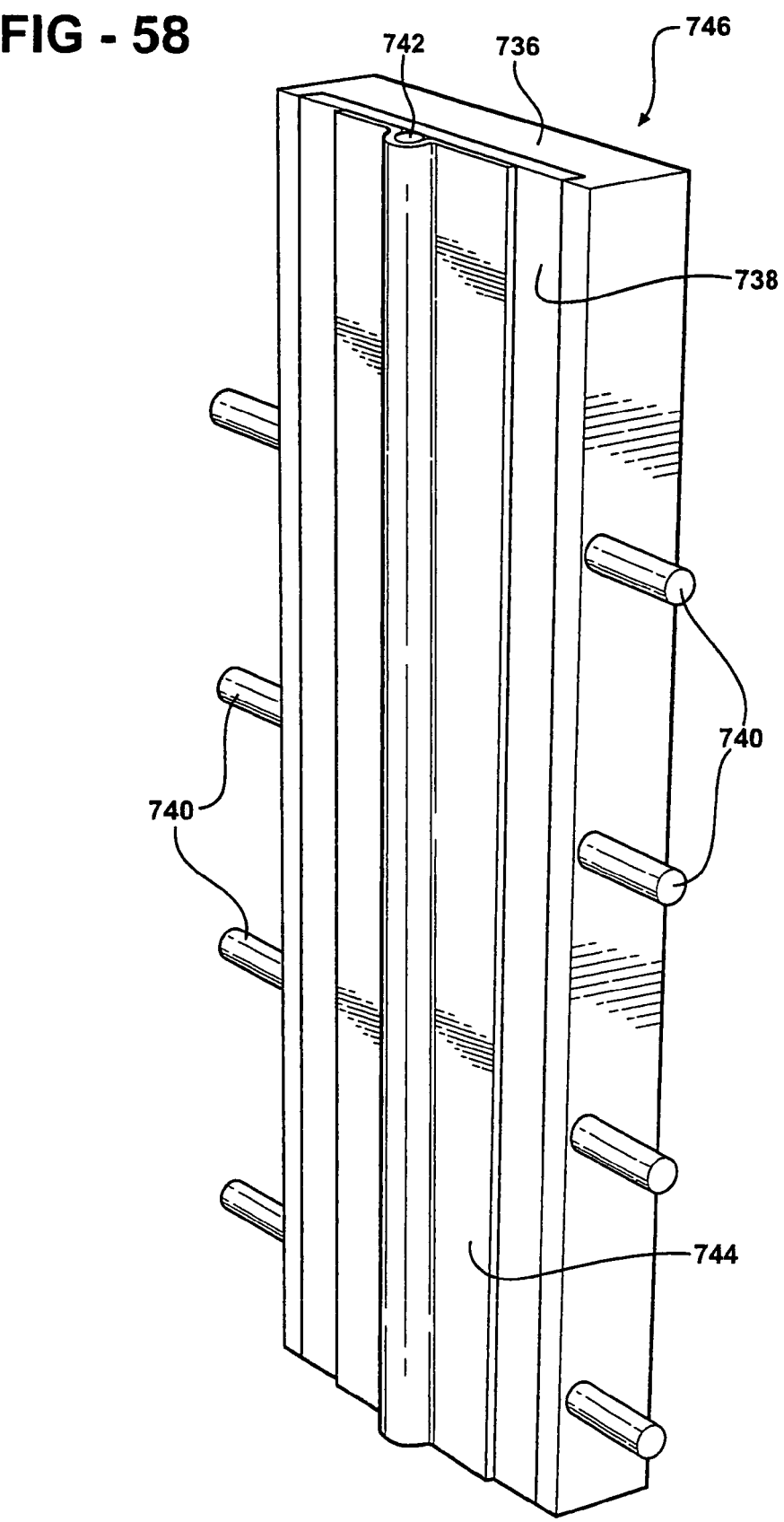
FIG. 58 is a perspective view of a calibration source for use with a holder of FIGS. 56 and 57.
Figure 59:
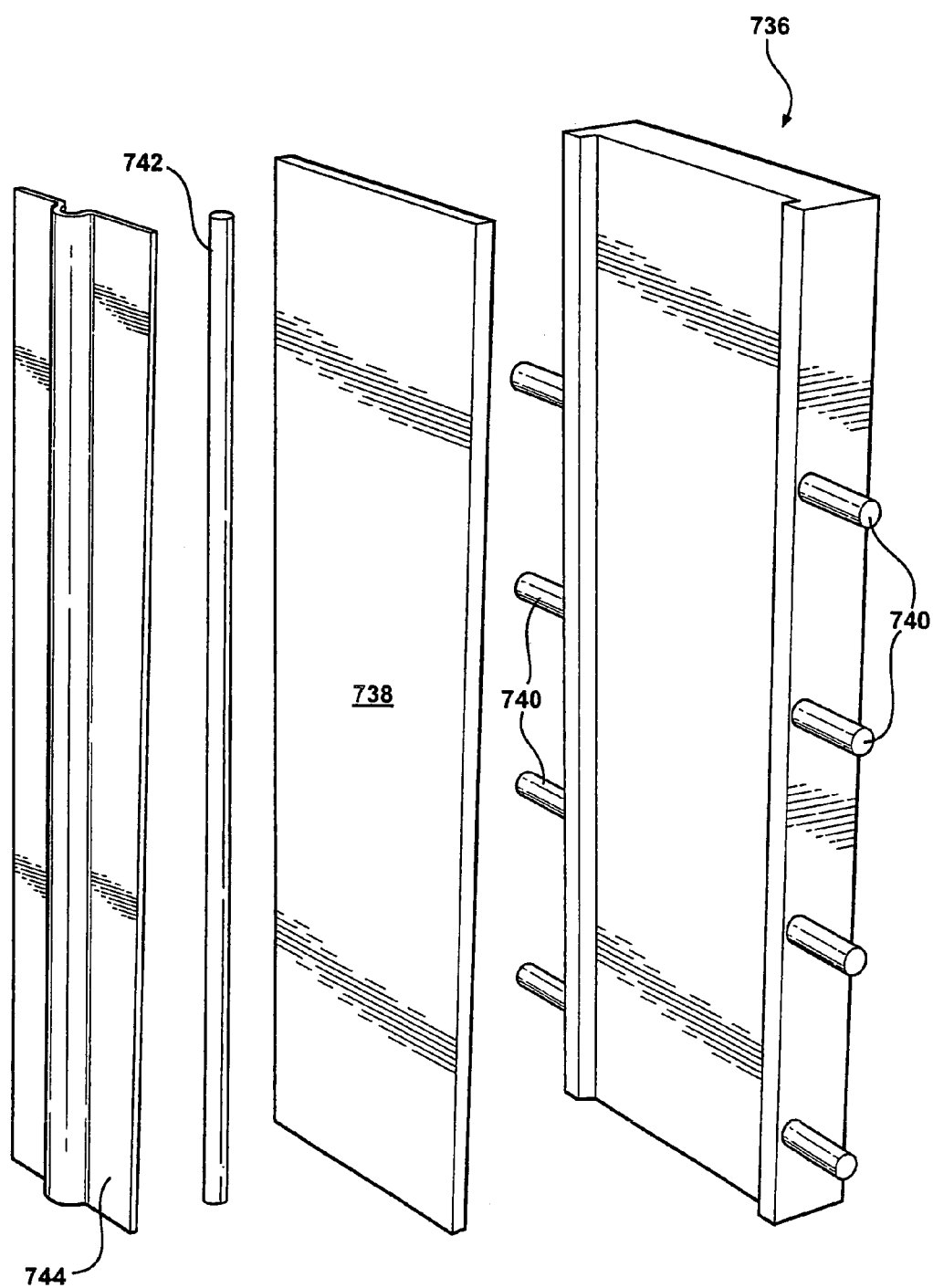
FIG. 59 is an exploded view of the calibration source of FIG. 58.

FIGS. 58 and 59 show a plastic block 736 that forms part of the calibration source 746. As shown, the plastic block 736 has a recess in the front face. A lead shield 738 is positioned in this recess in the plastic block 736. Guide pins 740 are provided extending from the sides of the plastic block 736. A radioactive rod 742 is positioned against the inner face of the lead shield. A plastic or aluminum retainer 744 is then positioned over the source to hold it against the lead shield and plastic block. This results in an assembled calibration source 746.

Figure 60:
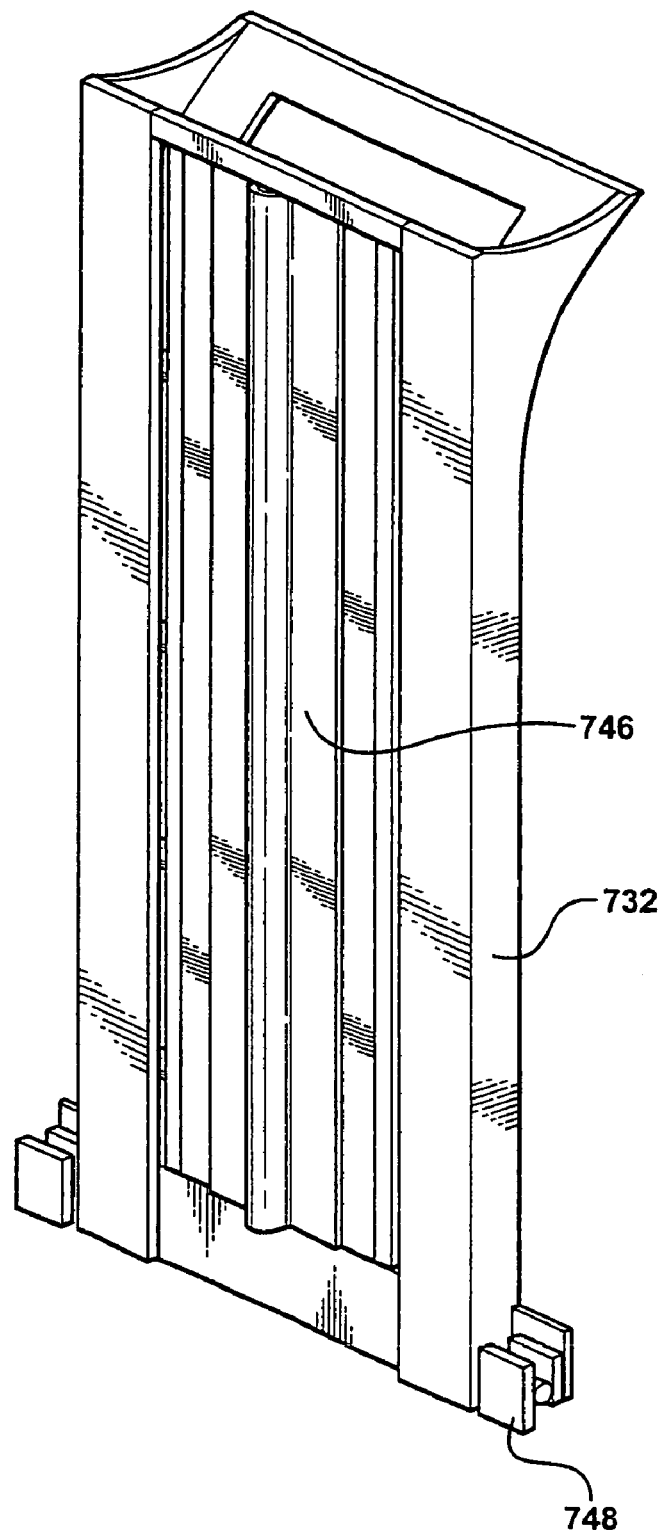
FIG. 60 is a perspective view of the holder of FIGS. 56 and 57 with the calibration source of FIGS. 58 and 59 received therein.
Figure 61:
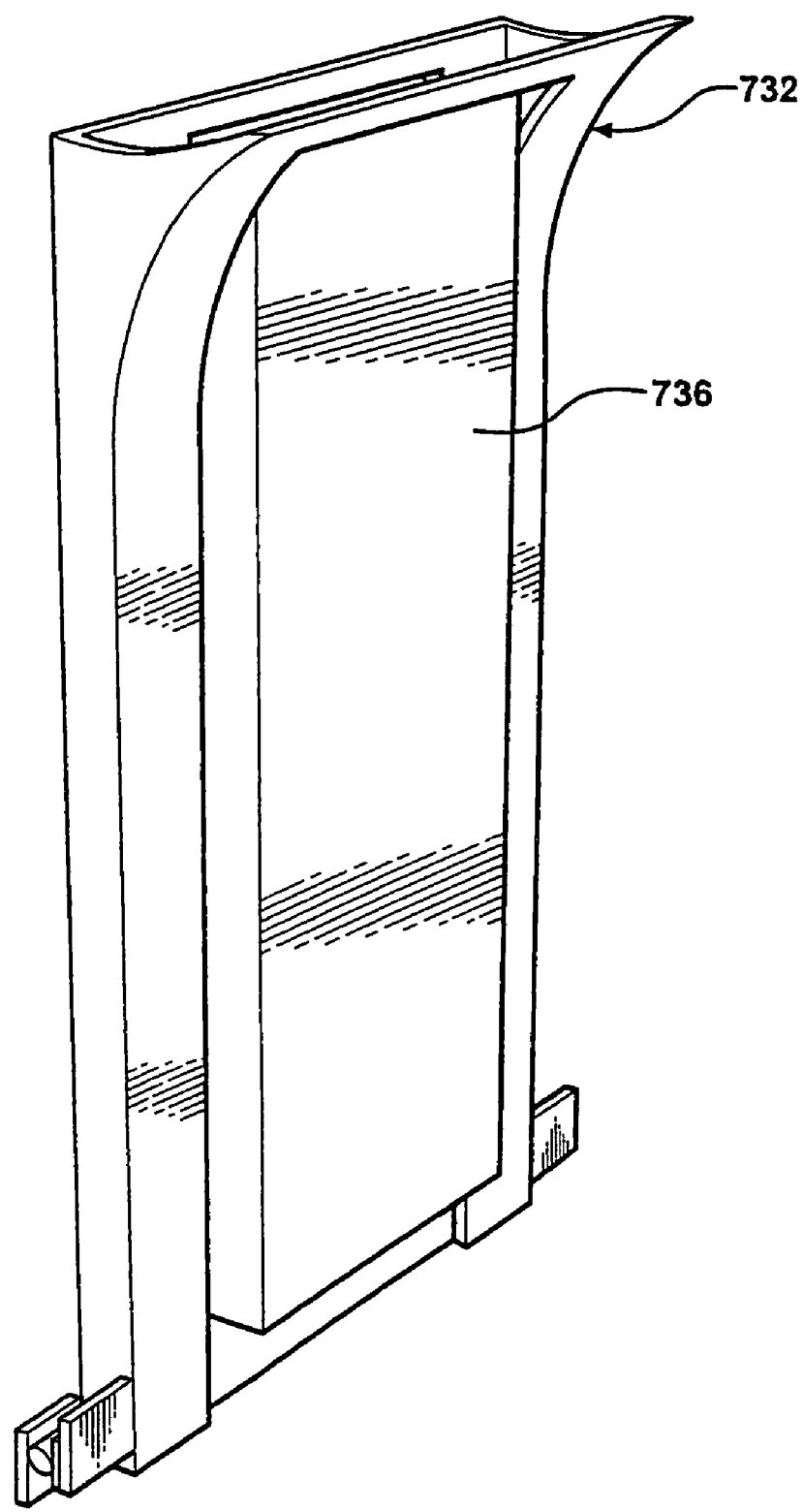
FIG. 61 is a perspective view of the source and holder of FIG. 60 showing the opposite side.
Figure 62:
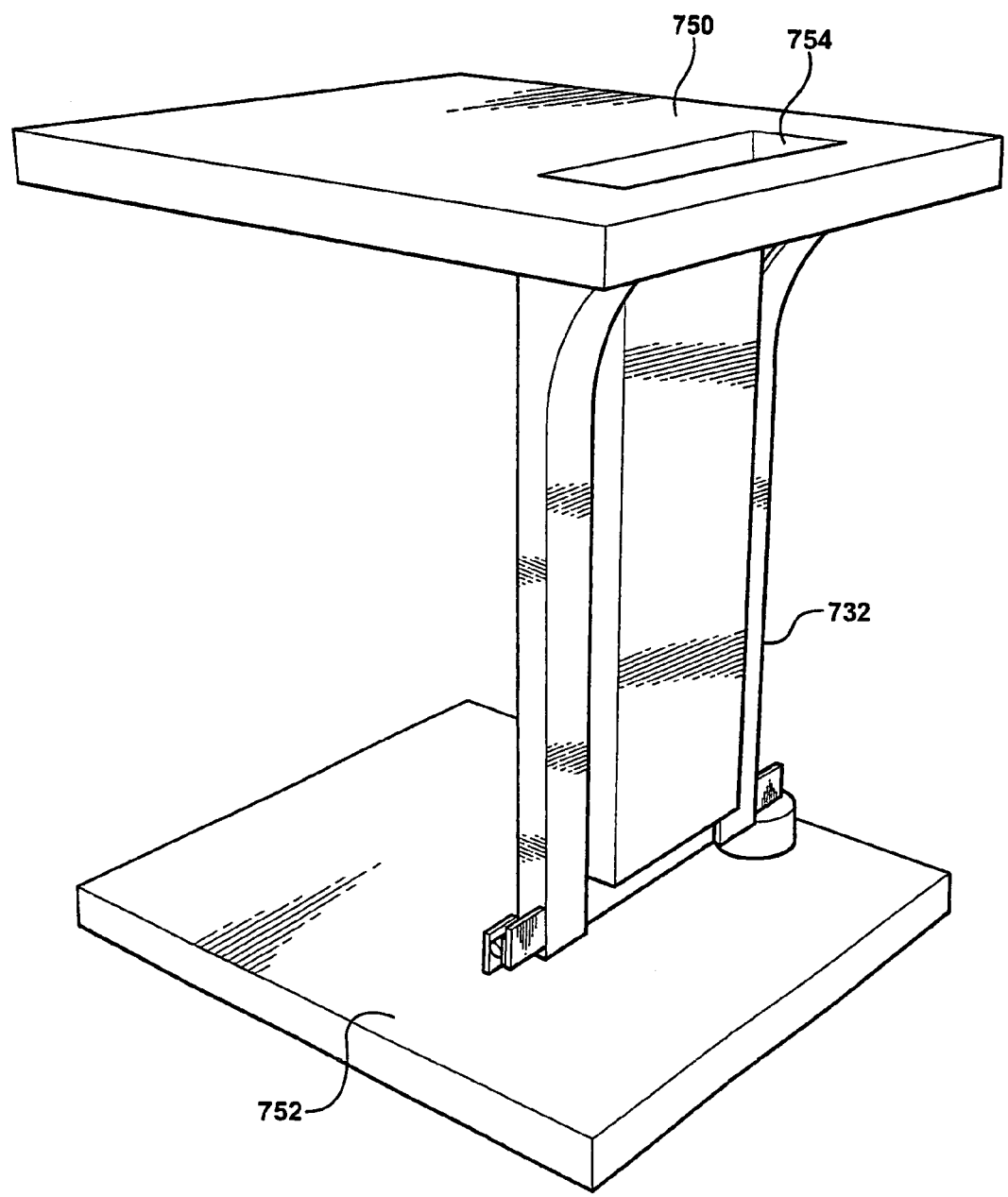
FIG. 62 is a perspective view of an upper and lower support member forming part of an imaging arc along with the holder and source of FIGS. 60 and 61.
Figure 63:
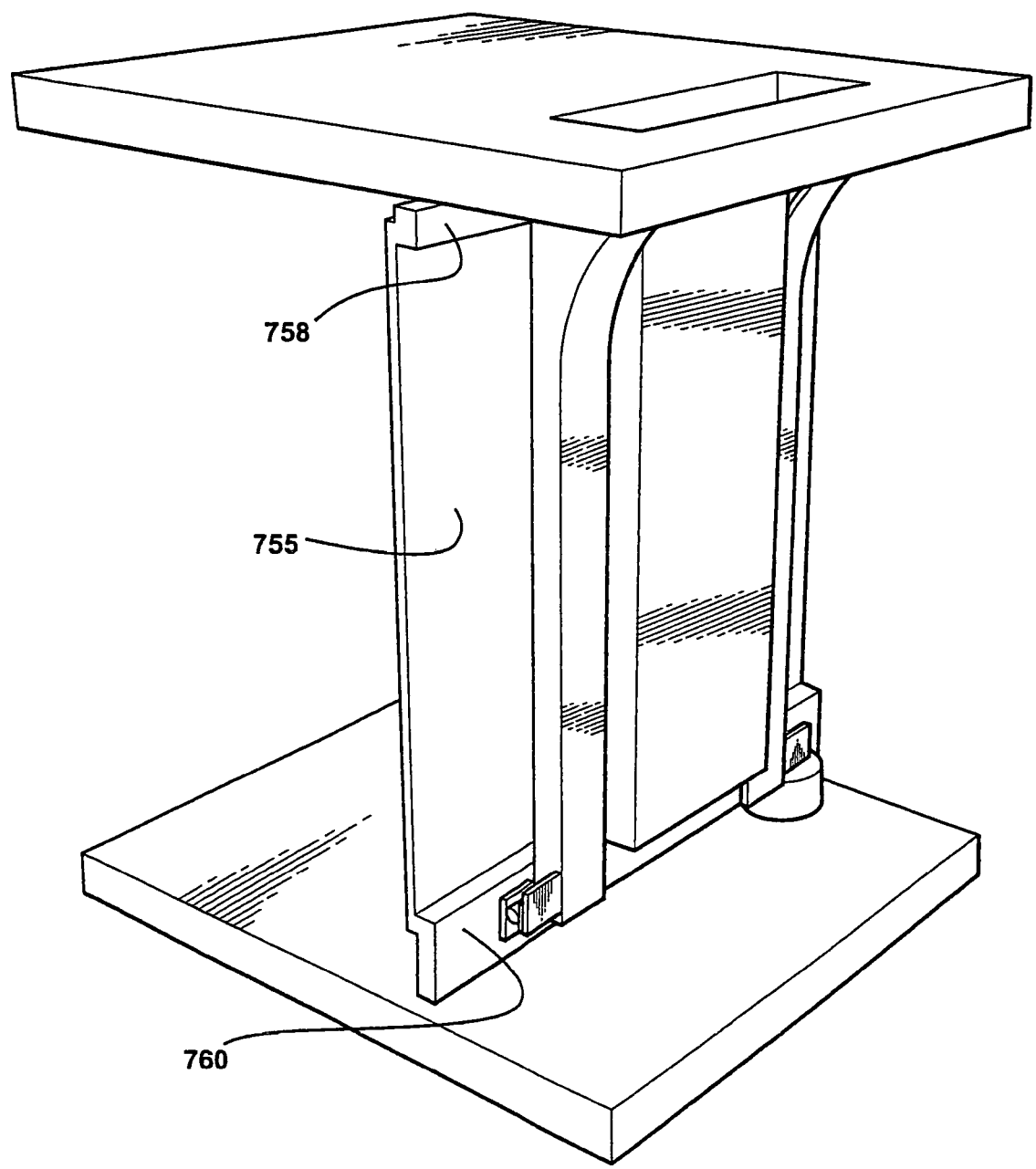
FIG. 63 is a perspective view similar to FIG. 62 with the addition of a portion of an aperture arc added.
Figure 64:
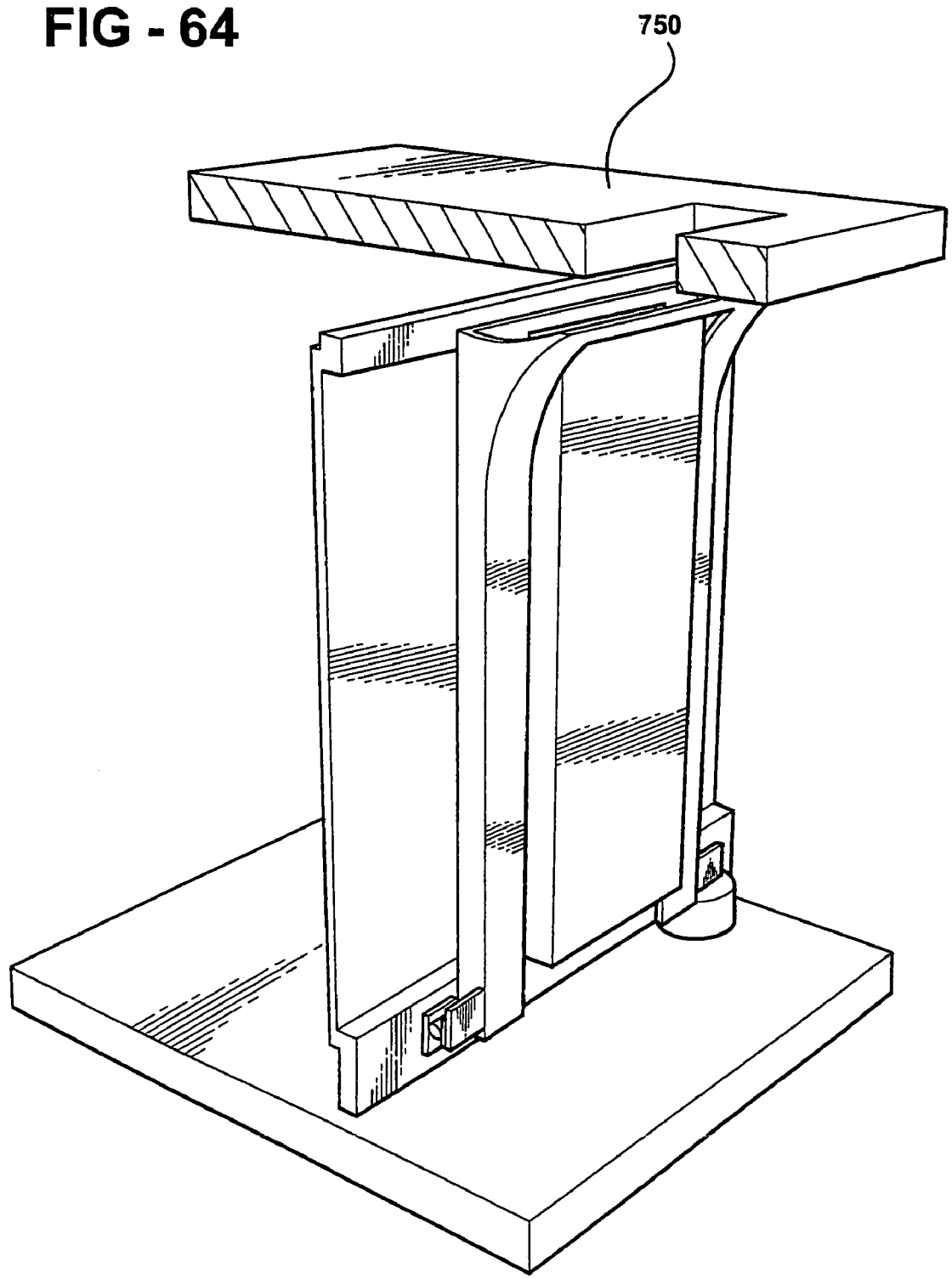
FIG. 64 is a perspective view similar to FIG. 63 with a portion of the upper support member cut away.

FIG. 60 shows the calibration source 746 positioned in the holder 732, with the holder supported by a hinge 748. FIG. 61 shows the holder 732 and the source 746 rotated so as to see the back side of the plastic block 736. FIG. 62 illustrates the holder 732 positioned between an upper support member 750 and lower support member 752 of the imaging arc, with an opening 754 defined through the upper member 750. FIG. 63 adds the aperture arc 755 which has upper and lower guide rails 758 and 760. FIG. 64 shows a portion of the upper support member 750 cut away.

Figure 65:
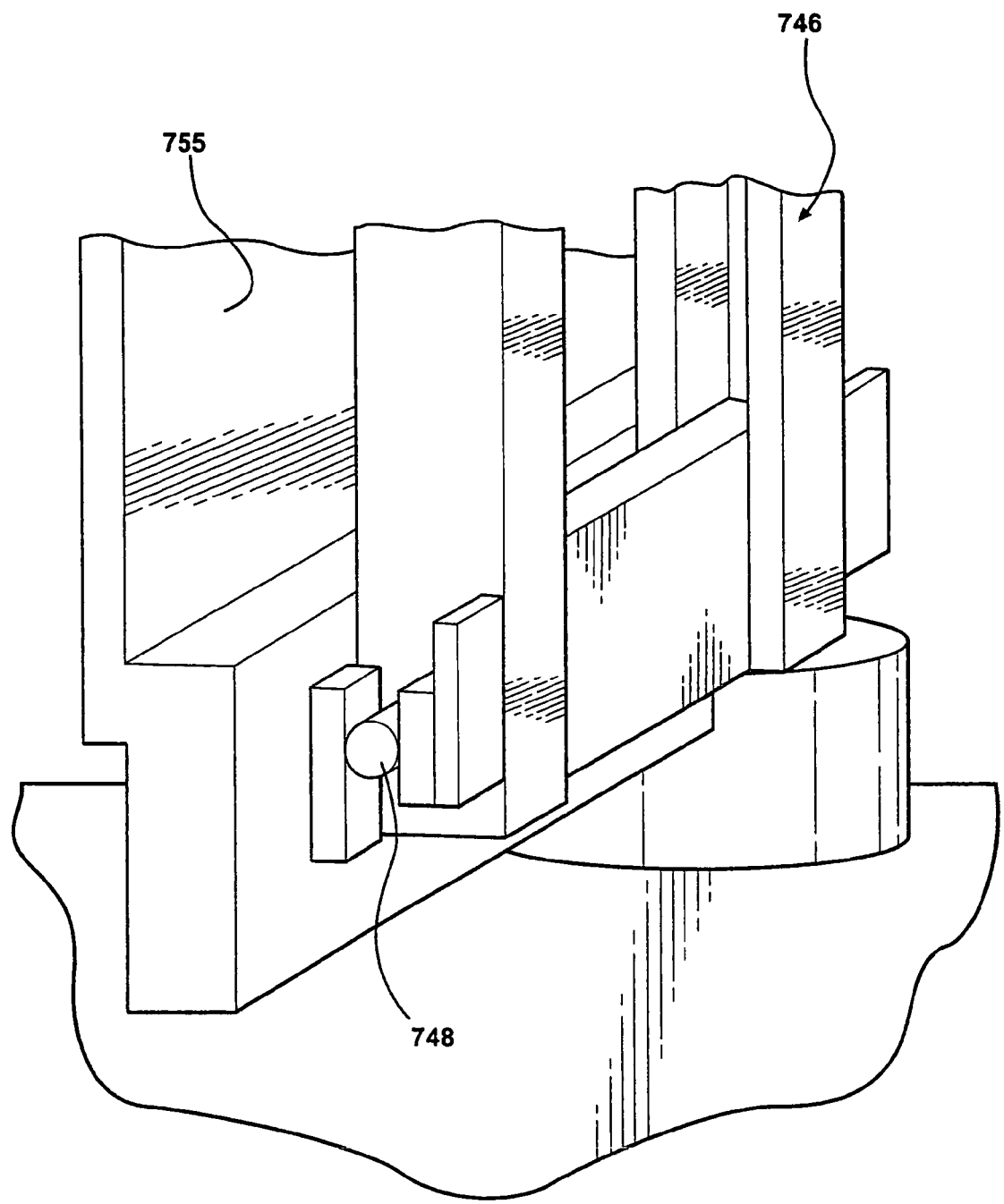
FIG. 65 is a detailed perspective view of a bottom part of the aperture arc and source holder of FIG. 64.

FIG. 65 shows a detailed view of the hinge 748 at the bottom of the source holder 746. In an alternative embodiment, a spring is provided, such as at the hinge 748, for spring biasing the upper end of the holder towards the aperture arc 755.

Figure 66:
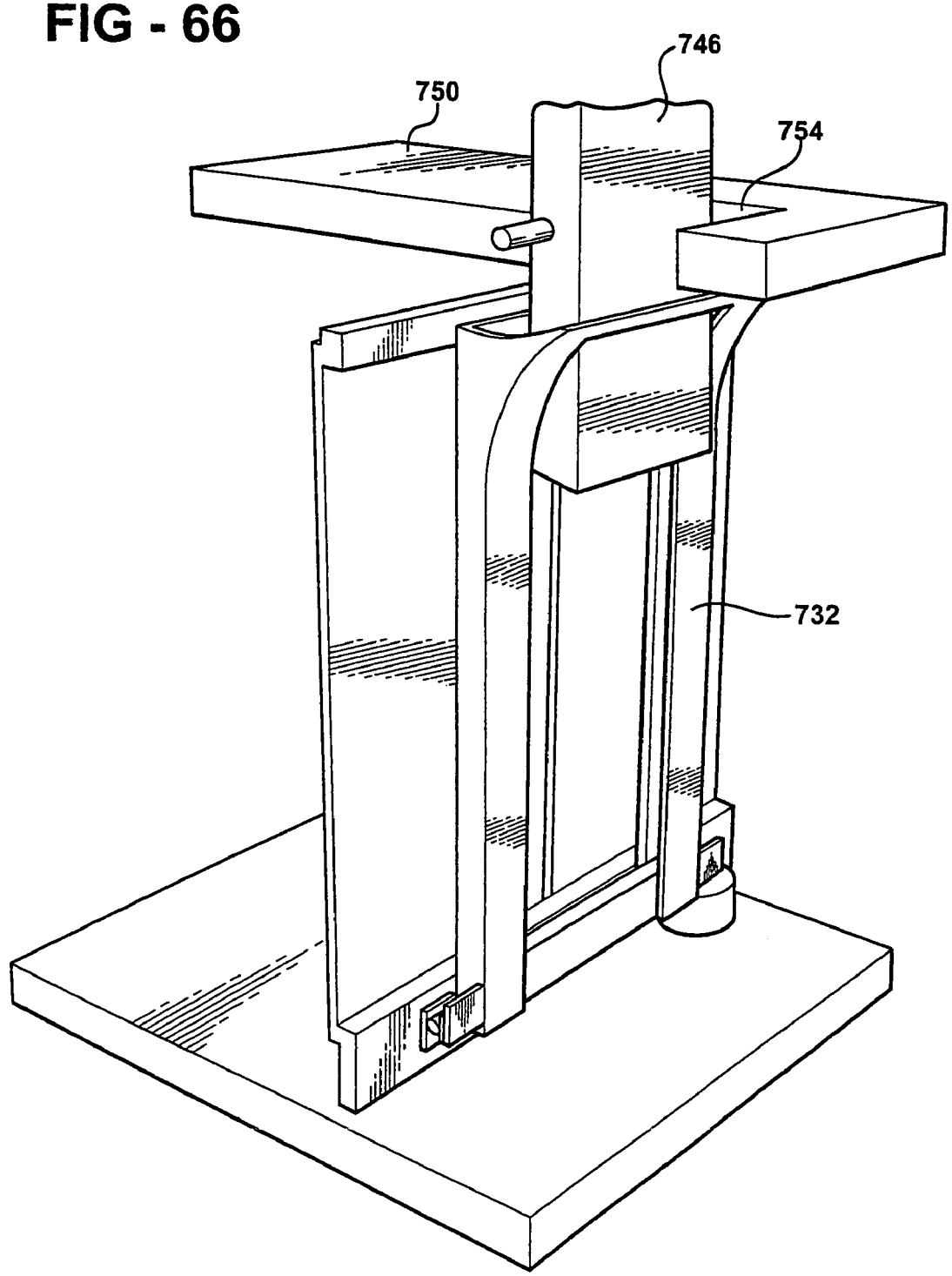
FIG. 66 is a perspective view of the calibration source and holder with the calibration source partially inserted.
Figure 67:
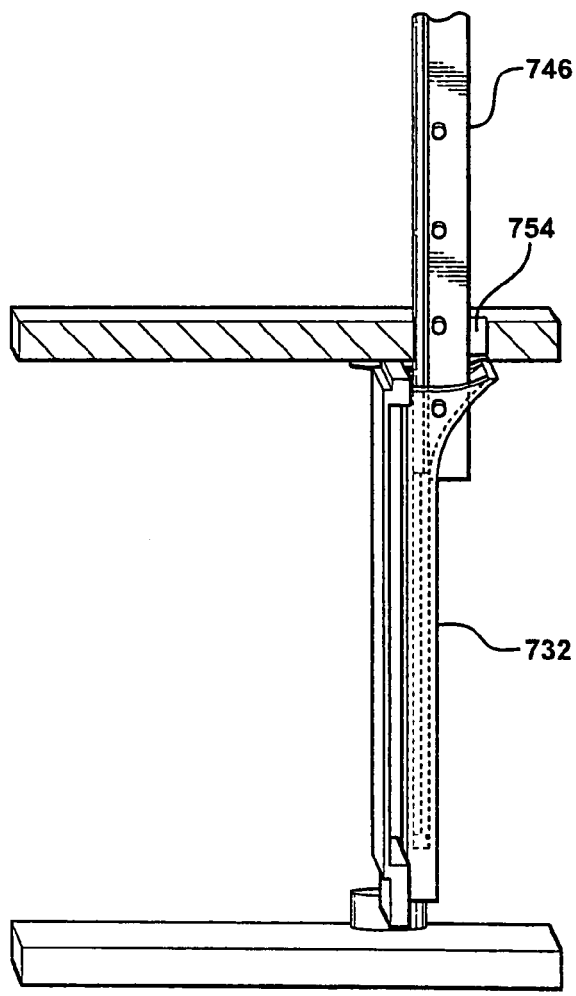
FIG. 67 is a side view of the source and holder of FIG. 66 with the source partially inserted.
Figure 68:
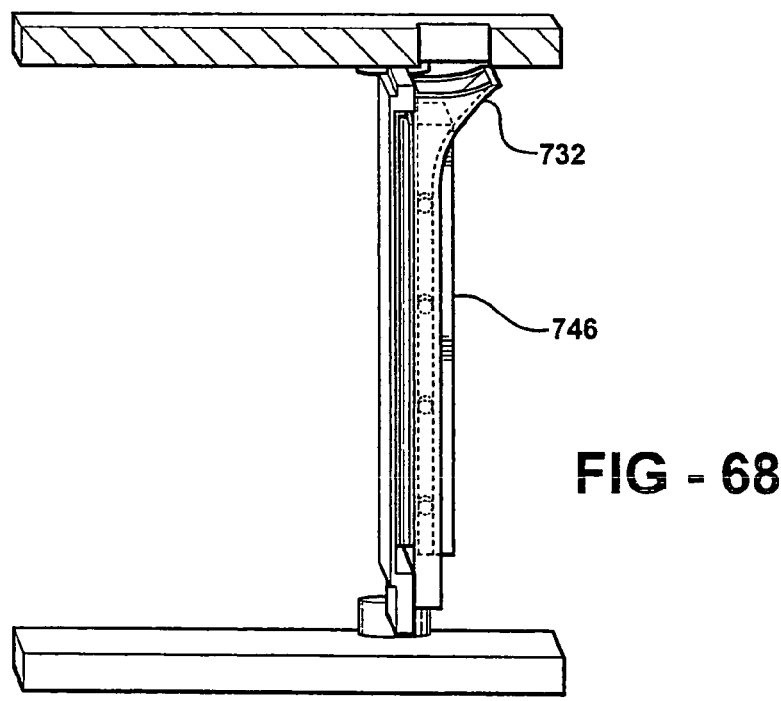
FIG. 68 is a side view similar to FIG. 67 with the source fully inserted.
Figure 69:
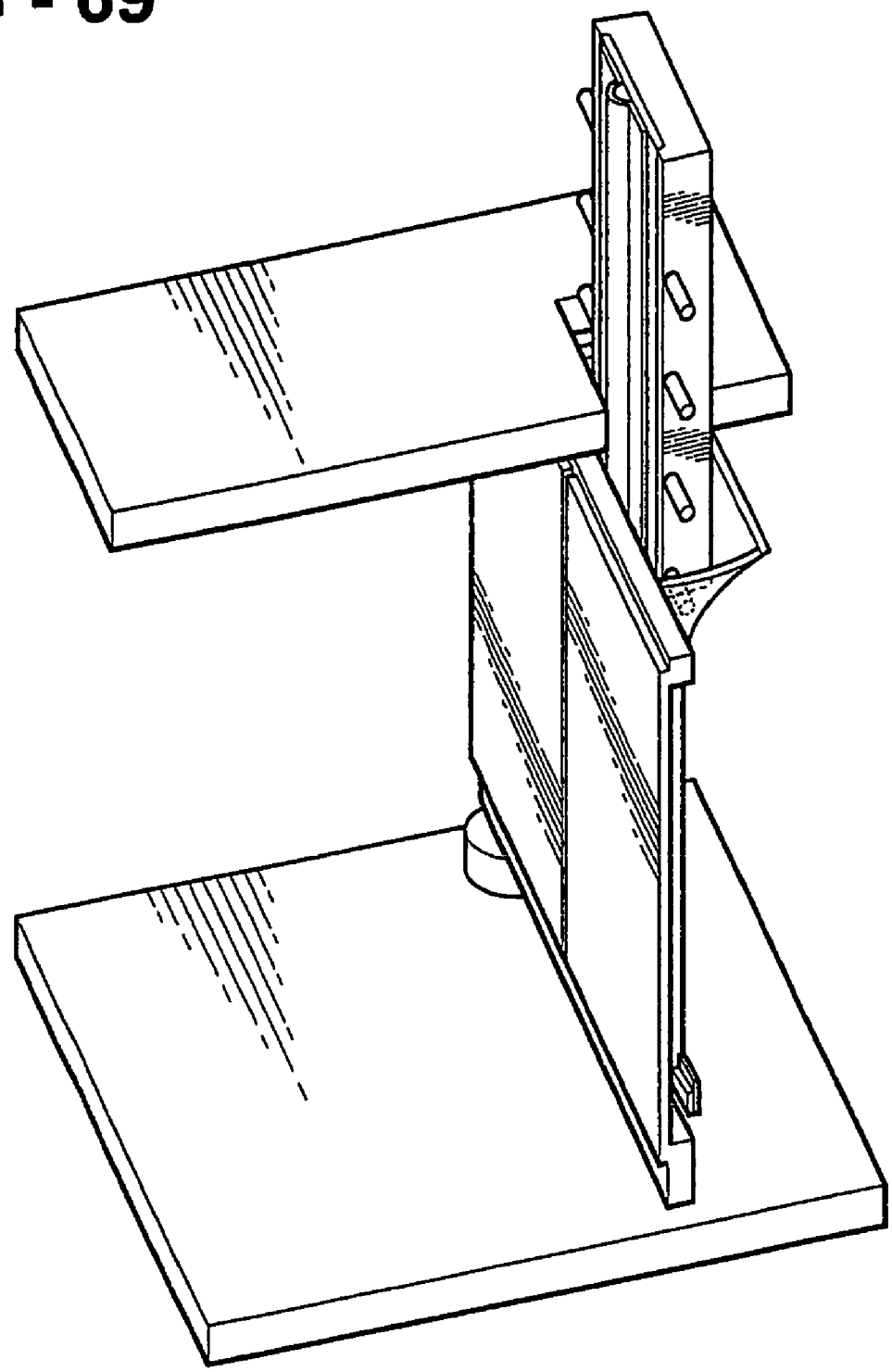
FIG. 69 is an additional perspective view of the source and holder from the opposite side as compared to FIG. 66, with the source partially inserted.
Figure 70:
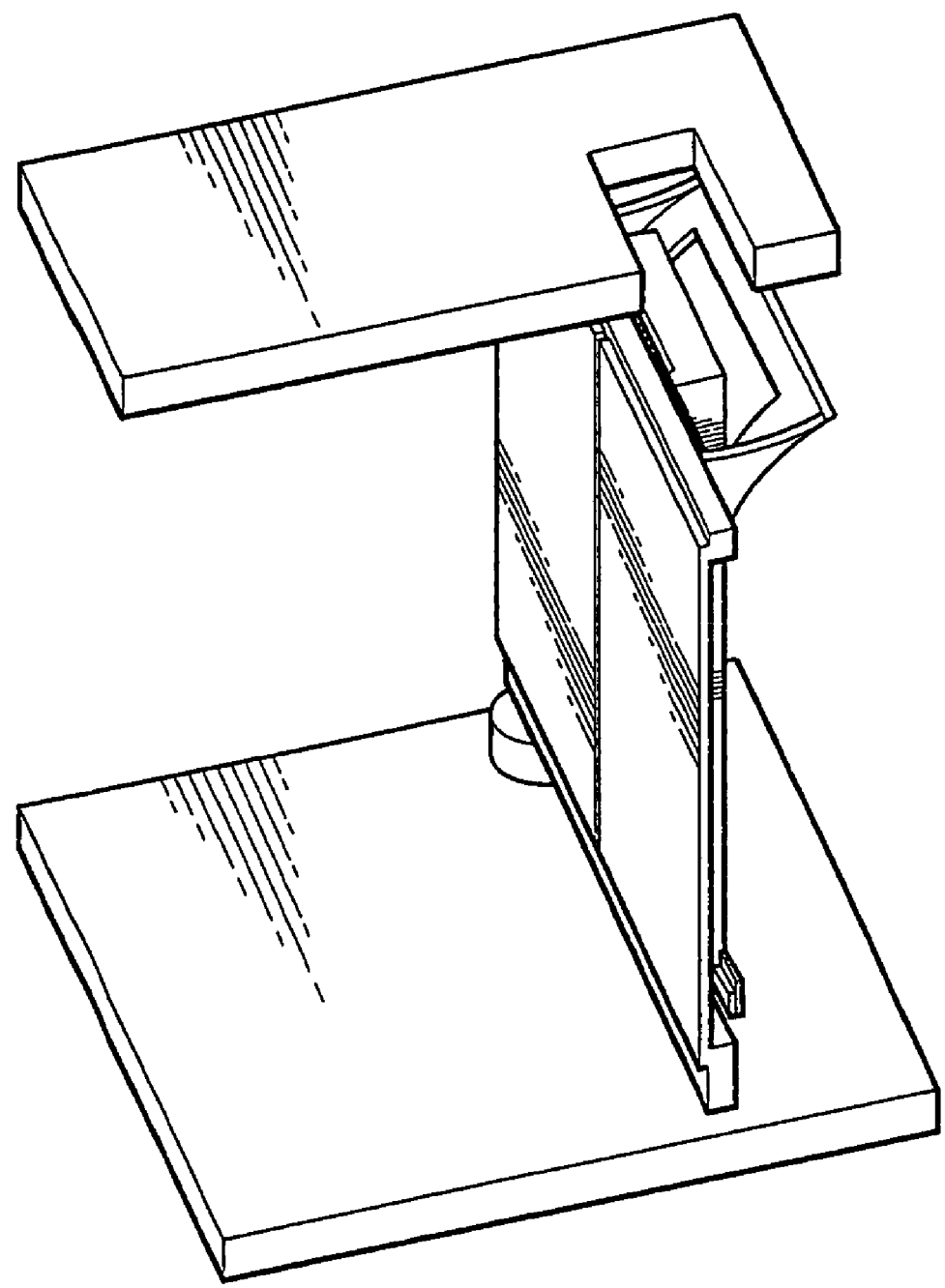
FIG. 70 is a perspective view similar to FIG. 69 with the source shown fully inserted.
Figure 71:
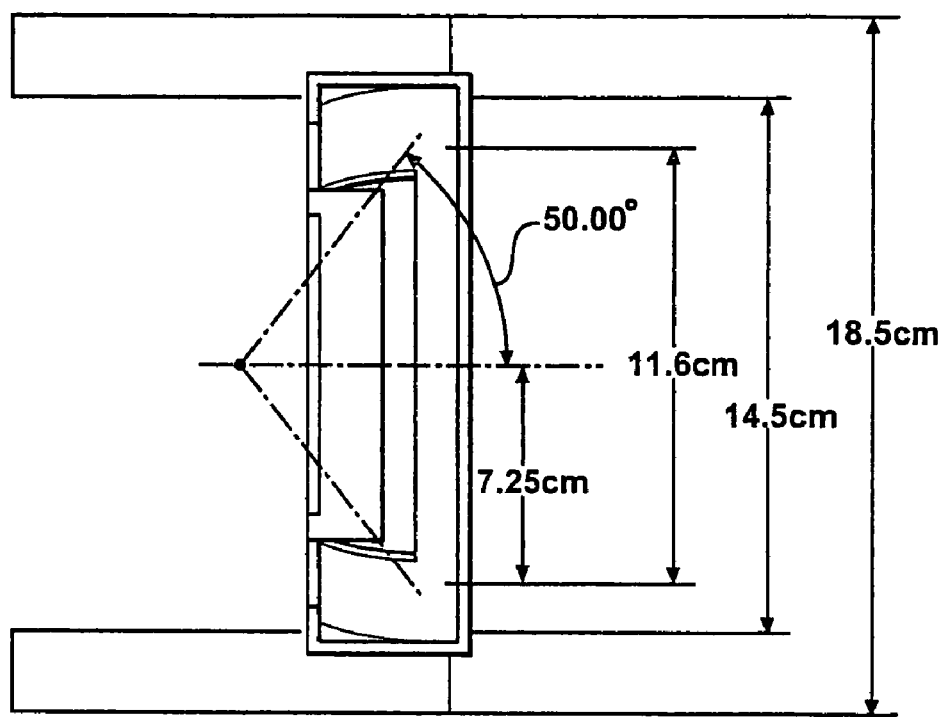
FIG. 71 is a top view of the calibration source holder of FIG. 70 with exemplary dimensions indicated thereon.

Due to construction details of some embodiments of the present invention, the opening in the upper support member cannot be provided close enough to the aperture arc such that the source can be dropped straight into place. Instead, it needs to be positioned away from the portion of the member that supports the aperture arc. FIG. 66 shows the source 746 being dropped through the opening 754 in the upper member 750 into the holder 732. A portion of the member is cut away for visibility. FIG. 67 shows the side view of FIG. 66, and illustrates how the opening 754 is positioned far enough back so that the carrier 746 does not move into position immediately adjacent the aperture arc as it extends through the opening 754. Instead, it strikes the sloped back surface of the holder 732. This causes the source to tilt somewhat, which in turn causes the holder 732 to pivot back on the hinge so as to align with the source. FIG. 68 shows the source 746 inserted fully into the holder 732 with the holder moved back forwardly, with its motion being caused either by the operator or by a spring in the hinge. The holder may then be held in place by the magnetic latch or by a spring, or by other means. FIGS. 69 and 70 illustrate additional views of this insertion process. FIG. 71 illustrates some sample dimensions for one embodiment of the holder 732.

Figure 72:
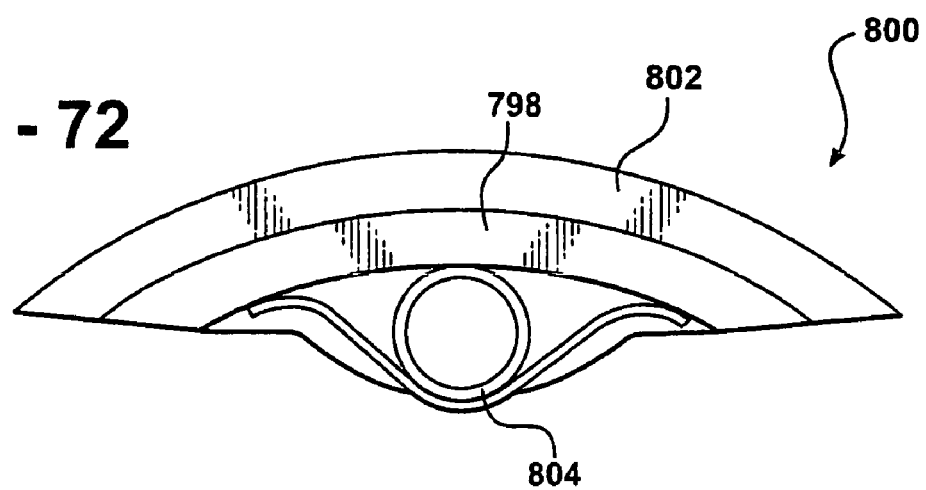
FIG. 72 is a top view of a calibration source.
Figure 73:
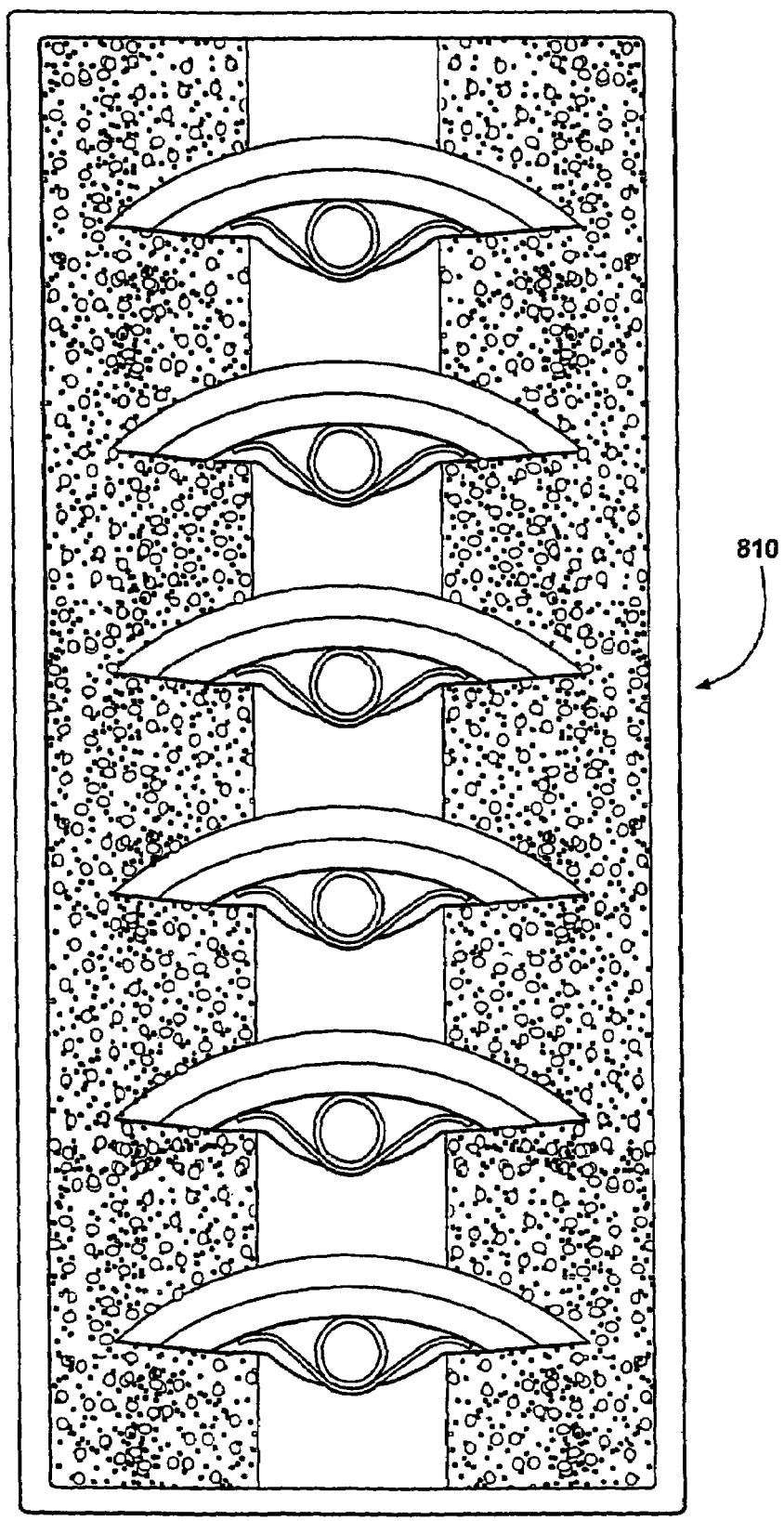
FIG. 73 is a top view of a calibration source storage container with a plurality of calibration sources disposed therein.

FIG. 72 illustrates an alternative embodiment of a calibration source which may be used with a holder similar to that shown in the previous figures. The calibration source is shaped similar to the source of FIG. 48 and has an arcute piece of lead or tungsten 798. The calibration source 800 has the piece of lead 798 wrapped in plastic 802 to protect the lead and to stiffen it. A tube 804 of radioactive material is affixed to the concave side of the lead and plastic assembly. A particular advantage to the calibration devices for use with the present invention is that they are much smaller, lighter, and easier to handle than the previous calibration devices. FIG. 73 illustrates a calibration holding box 810 with six calibration sources positioned inside of it. Each source may nest such that they fit compactly into the box 810. The total weight of the box and calibration sources may be as little as 6 or 10 pounds, making it easy for a technician to handle without unnecessary exposure.

XX. Curved Crystal Detectors

Figure 74:
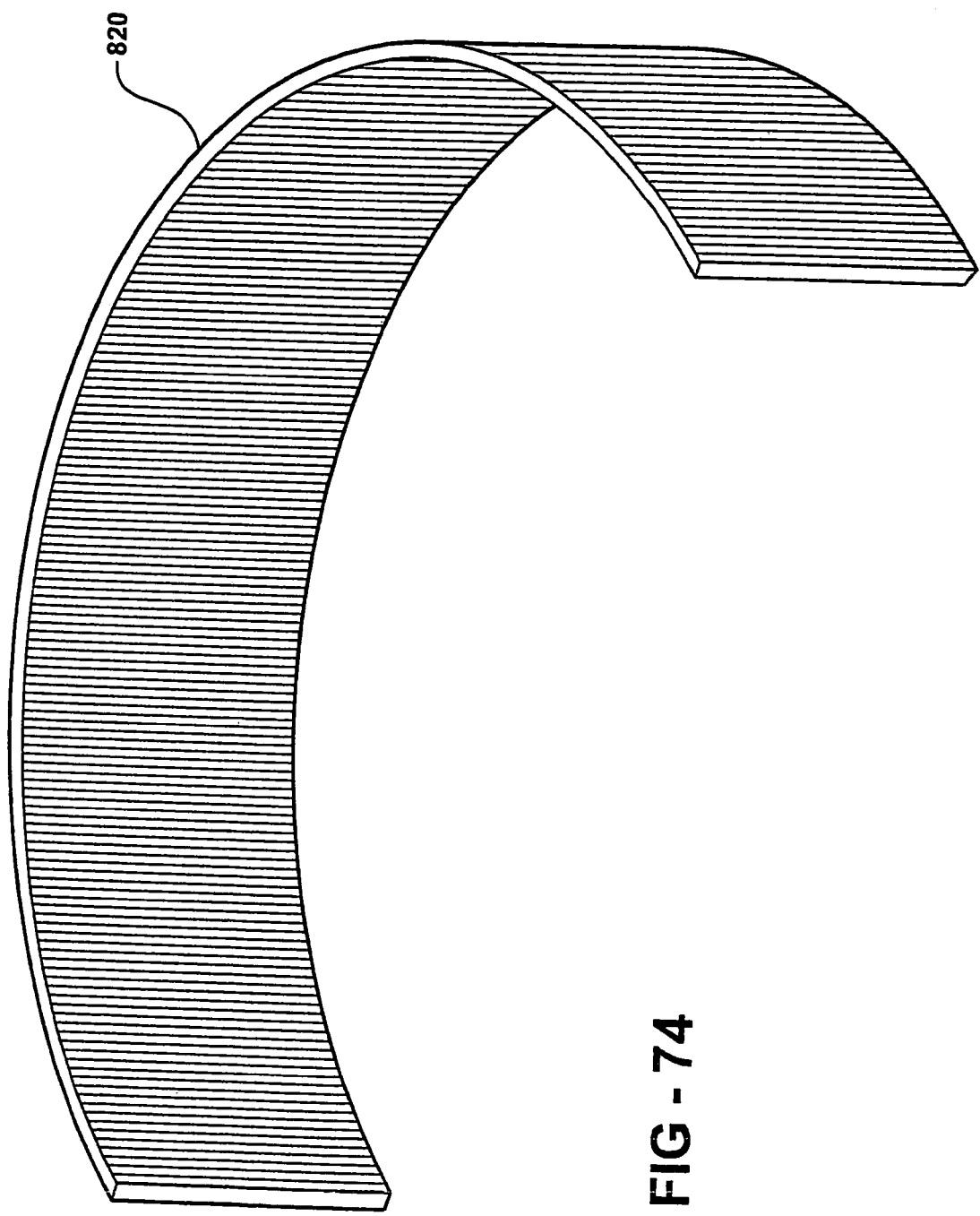
FIG. 74 is a perspective view of a curved crystal used in some embodiments of the present invention.
Figure 75:
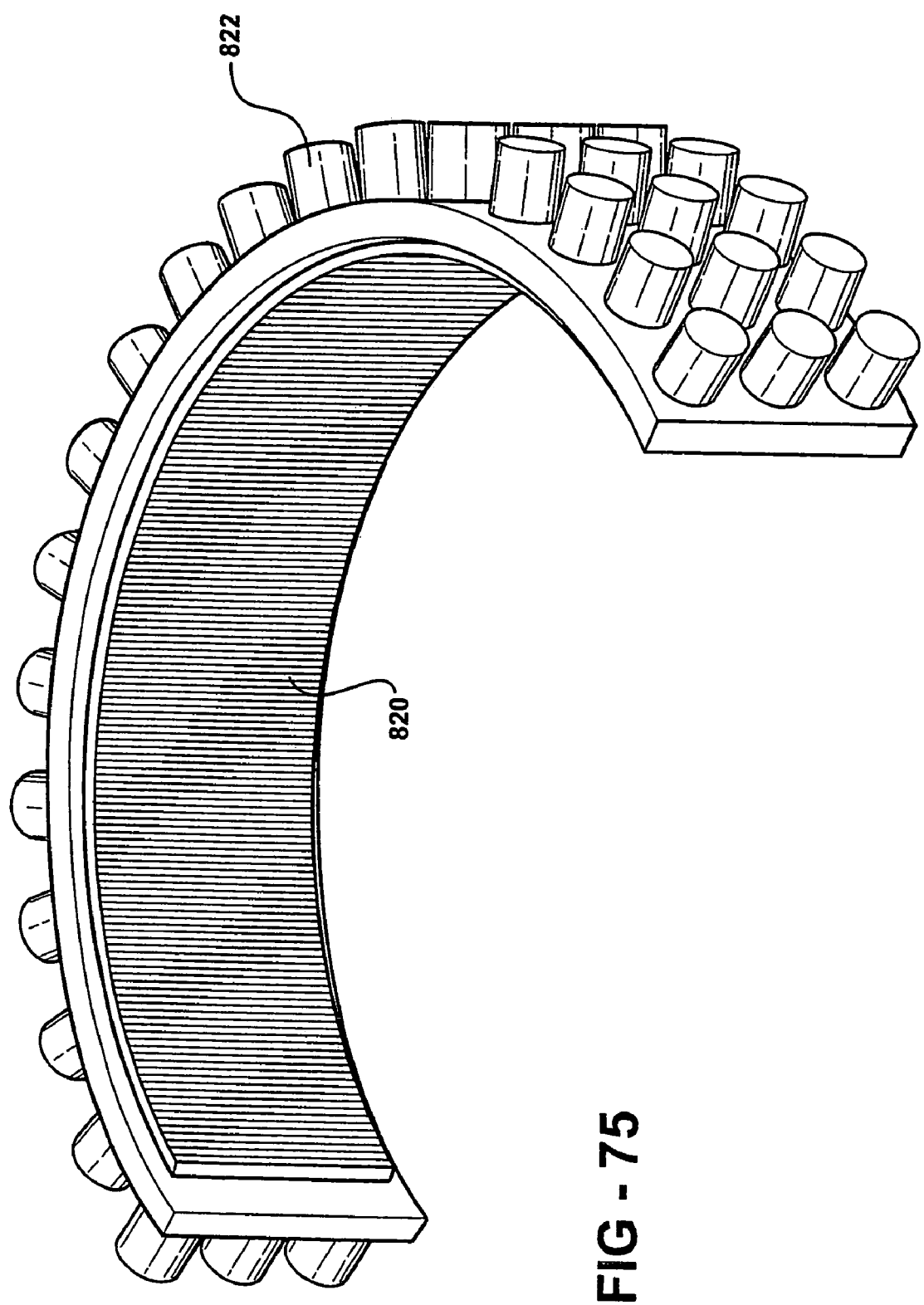
FIG. 75 is a perspective view of the crystal of FIG. 74 backed by a plurality of photo tubes.

As discussed previously, the present invention may be made with either solid state detectors, such as CZT, or with scintillation material backed by photo tubes. In earlier embodiments, individual pieces of scintillation material were assembled side-by-side. According to a preferred alternative, a single large curved crystal of scintillation material may be provided, such as shown in FIG. 74 at 820. This single curved piece of crystal may be scored along its face, with the score lines being cut partially through the crystal so as to divide it into different photon receiving regions. FIG. 75 illustrates the crystal 820 backed by a plurality of photo tubes 822.

Other variations on the disclosed preferred embodiments will be clear to those of skill in the art. It is the following claims, including all equivalents, that define the scope of the present invention.

I claim:

1. A single photon emission computed tomography system for producing multiple tomographic images of the type representing a three-dimensional distribution of a photon-emitting radioisotope, the system comprising:
    a base including a patient support for supporting a human patient such that a portion of the patient's torso is located in a field of view, a longitudinal axis being defined through the field of view;
    a detector assembly adjacent the field of view, the detector assembly including a photon-responsive detector operable to detect if a photon strikes the detector, the detector assembly operable to scan for photons emitted from the portion of the patient's torso located in the field of view; and
    a collimating assembly including a plurality of collimating vanes formed of photon-attenuating material, the vanes being spaced apart so as to define a plurality of gaps, the gaps each having a height of at least 3 mm, the plurality of vanes being disposed between the detector and the field of view such that photons traveling from the field of view to the detector may pass through one of the gaps.

2. The system according to claim 1, wherein the gaps each have a height of at least 4 mm.

3. The system according to claim 1, wherein each of the vanes has a front to back depth that is greater than 10 times the height of each of the gaps.

4. The system according to claim 3, wherein the depth of each of the vanes is greater than 20 times the height of each of the gaps.

5. The system according to claim 3, wherein the depth of each of the vanes is greater than 30 times the height of each of the gaps.

6. The system according to claim 3, wherein the depth of each of the vanes is greater than or equal to 33 times the height of each of the gaps.

7. The system according to claim 1, wherein each of the vanes has a thickness greater than or equal to 1 mm.

8. The system according to claim 1, wherein each of the vanes has a front to back depth that is greater than or equal to 100 mm.

9. The system according to claim 8, wherein the depth of each of the vanes is greater than or equal to 150 mm.

10. The system according to claim 1, wherein the longitudinal axis is generally vertical, such that the patient's torso extends generally vertically with the patient's head substantially higher than the patient's hips.

11. The system according to claim 10, wherein the base comprises a chair-like structure having a generally horizontal bottom portion for supporting the patient's hips and a generally vertical back portion for supporting the patient's back.

12. The system according to claim 11, wherein the detector assembly comprises a generally arcuate housing at least partially surrounding the field of view.

13. The system according to claim 12, wherein the arcuate housing is interconnected with the back portion of the base such that the housing partially surrounds the patient's torso when the patient is seated on the bottom portion, the housing extending generally arcuately between a pair of ends that are spaced apart so as to define an entry opening to the field of view.

14. The system according to claim 1, wherein a radiolucent material is disposed in the gaps between the vanes.

15. The system according to claim 1, wherein the collimating vanes are generally perpendicular to the longitudinal axis.

16. The system according to claim 1, wherein the collimating vanes are angled with respect to the longitudinal axis.

17. A single photon emission computed tomography system for producing multiple tomographic images of the type representing a three-dimensional distribution of a photon-emitting radioisotope, the system comprising:
    a base including a patient support for supporting a human patient such that a portion of the patient's torso is located in a field of view, a longitudinal axis being defined through the field of view;
    a detector assembly adjacent the field of view, the detector assembly including a photon-responsive detector operable to detect if a photon strikes the detector, the detector assembly operable to scan for photons emitted from the portion of the patient's torso located in the field of view;
    a photon-blocking member disposed between the field of view and the detector, the blocking member having an aperture slot defined therethrough for passage of photons aligned with the aperture slot, a line of response being defined from the detector through the aperture;
    a collimating assembly including a plurality of collimating vanes formed of photon-attenuating material, the vanes being spaced apart so as to define a plurality of gaps, the gaps each having a height of at least 3 mm, the plurality of vanes being disposed between the detector and the field of view such that photons traveling from the field of view to the detector may pass through one of the gaps; and
    a displacement actuator operable to move one of the detector and the photon-blocking member relative to the other of the detector and the photon-blocking member such that the aperture is displaced relative to the detector and the line of response is swept across at least a portion of the field of view.

18. The system according to claim 17, wherein the gaps each have a height of at least 4 mm.

19. The system according to claim 17, wherein each of the vanes has a front to back depth that is greater than 10 times the height of each of the gaps.

20. The system according to claim 19, wherein the depth of each of the vanes is greater than 20 times the height of each of the gaps.

21. The system according to claim 19, wherein the depth of each of the vanes is greater than 10 times the height of each of the gaps.

22. The system according to claim 19, wherein the depth of each of the vanes is greater than or equal to 33 times the height of each of the gaps.

23. The system according to claim 17, wherein each of the vanes has a thickness greater than or equal to 1 mm.

24. The system according to claim 17, wherein each of the vanes has a front to back depth that is greater than or equal to 100 mm.

25. The system according to claim 24, wherein the depth of each of the vanes is greater than or equal to 150 mm.

26. The system according to claim 17, wherein the longitudinal axis is generally vertical, such that the patient's torso extends generally vertically with the patient's head substantially higher than the patient's hips.

27. The system according to claim 26, wherein the base comprises a chair-like structure having a generally horizontal bottom portion for supporting the patient's hips and a generally vertical back portion for supporting the patient's back.

28. The system according to claim 27, wherein the detector assembly comprises a generally arcuate housing at least partially surrounding the field of view.

29. The system according to claim 28, wherein the arcuate housing is interconnected with the back portion of the base such that the housing partially surrounds the patient's torso when the patient is seated on the bottom portion, the housing extending generally arcuately between a pair of ends that are spaced apart so as to define an entry opening to the field of view.

30. The system according to claim 17, wherein a radiolucent material is disposed in the gaps between the vanes.

31. The system according to claim 17, wherein the collimating vanes are generally perpendicular to the longitudinal axis.

32. The system according to claim 17, wherein the collimating vanes are angled with respect to the longitudinal axis.

33. The system according to claim 17, wherein the aperture slot is generally parallel to the longitudinal axis.

34. The system according to claim 17, wherein the aperture slot is generally perpendicular to at least some of said vanes.

35. The system according to claim 17, wherein said collimating vanes are disposed between said photon-blocking member and said detector.

* * * * *

UNITED STATES PATENT AND TRADEMARK OFFICE
CERTIFICATE OF CORRECTION

| | | |
|---|---|---|
| PATENT NO. | : 7,071,473 B2 | Page 1 of 1 |
| APPLICATION NO. | : 11/250647 | |
| DATED | : July 4, 2006 | |
| INVENTOR(S) | : Jack E. Juni | |

It is certified that error appears in the above-identified patent and that said Letters Patent is hereby corrected as shown below:

Column 1, line 11, replace "pan" with --part--.

Signed and Sealed this

Thirteenth Day of March, 2007

JON W. DUDAS
*Director of the United States Patent and Trademark Office*